(12) United States Patent
Tanaka et al.

(10) Patent No.: US 8,347,881 B2
(45) Date of Patent: Jan. 8, 2013

(54) PNEUMOSTOMA MANAGEMENT DEVICE WITH INTEGRATED PATENCY SENSOR AND METHOD

(75) Inventors: Don Tanaka, Saratoga, CA (US); Joshua P. Wiesman, Boston, MA (US); David C. Plough, Portola Valley, CA (US)

(73) Assignee: Portaero, Inc., Cupertino, CA (US)

( * ) Notice: Subject to any disclaimer, the term of this patent is extended or adjusted under 35 U.S.C. 154(b) by 498 days.

(21) Appl. No.: 12/684,699

(22) Filed: Jan. 8, 2010

(65) Prior Publication Data

US 2010/0170507 A1    Jul. 8, 2010

Related U.S. Application Data

(60) Provisional application No. 61/143,298, filed on Jan. 8, 2009, provisional application No. 61/151,581, filed on Feb. 11, 2009.

(51) Int. Cl.
*A61B 7/00* (2006.01)
(52) U.S. Cl. ............... 128/200.24; 604/174; 604/93.01; 606/185; 128/207.29
(58) Field of Classification Search ............... 606/108, 606/185, 167; 604/174, 93.01; 128/200.24, 128/207.14, 207.29
See application file for complete search history.

(56) References Cited

U.S. PATENT DOCUMENTS

| | | |
|---|---|---|
| 733,152 A | 7/1903 | Chisholm |
| 953,922 A | 4/1910 | Rogers |
| 2,206,687 A | 7/1940 | Bloomheart |
| 2,867,213 A | 1/1959 | Thomas, Jr. |
| 2,873,742 A | 2/1959 | Shelden |
| 2,991,787 A | 7/1961 | Shelden et al. |
| 3,253,594 A | 5/1966 | Matthews et al. |
| 3,384,087 A | 5/1968 | Brummelkamp |
| 3,463,159 A | 8/1969 | Heimlich |
| 3,511,243 A | 5/1970 | Toy |
| 3,556,103 A | 1/1971 | Calhoun et al. |
| 3,638,649 A | 2/1972 | Ersek |

(Continued)

FOREIGN PATENT DOCUMENTS

EP       0260543 A1    3/1988

(Continued)

OTHER PUBLICATIONS

Rendina et al., "Feasibility and safety of the airway bypass procedure for patients with emphysema", The Journal of Thoracic and Cardiovascular Surgery 2003; 125: 1294-1299.

(Continued)

*Primary Examiner* — Laura Bouchelle
(74) *Attorney, Agent, or Firm* — Fliesler Meyer LLP

(57) ABSTRACT

A flexible pneumostoma management device maintains the patency of a pneumostoma while controlling the flow of material through the pneumostoma. The pneumostoma management device includes a pneumostoma vent having a tube which enters the pneumostoma to allow gases to escape the lung, a flange and a filter/valve to control flow of materials through the tube. The flange is a thin flexible patch comprises of multiple thin layers of materials and which conforms and attaches to the chest of the patient. The flange includes a filter, a protective outer layer and an inner hydrocolloid layer. The flange secures the tube in position in the pneumostoma. An indicator responsive to gases exiting the pneumostoma is integrated into the device and provides and external indicia of the patency and efficacy of the pneumostoma.

20 Claims, 25 Drawing Sheets

U.S. PATENT DOCUMENTS

| | | |
|---|---|---|
| 3,682,166 A | 8/1972 | Jacobs |
| 3,688,773 A | 9/1972 | Weiss |
| 3,707,146 A | 12/1972 | Cook et al. |
| 3,766,920 A | 10/1973 | Greene |
| 3,777,757 A | 12/1973 | Gray et al. |
| 3,788,326 A | 1/1974 | Jacobs |
| 3,817,250 A | 6/1974 | Weiss et al. |
| 3,908,704 A | 9/1975 | Clement et al. |
| 3,916,903 A | 11/1975 | Pozzi |
| 4,153,058 A | 5/1979 | Nehme |
| 4,291,694 A | 9/1981 | Chai |
| 4,439,189 A | 3/1984 | Sargeant et al. |
| 4,465,062 A | 8/1984 | Versaggi et al. |
| 4,502,482 A | 3/1985 | DeLuccia et al. |
| 4,583,977 A | 4/1986 | Shishov et al. |
| 4,664,660 A | 5/1987 | Goldberg et al. |
| 4,691,701 A * | 9/1987 | Williams ............... 128/207.14 |
| 4,799,494 A | 1/1989 | Wang |
| 4,813,929 A | 3/1989 | Semrad |
| 4,826,495 A | 5/1989 | Petersen |
| 4,828,553 A | 5/1989 | Nielsen |
| 4,869,717 A | 9/1989 | Adair |
| 4,872,869 A | 10/1989 | Johns |
| 4,889,534 A | 12/1989 | Mohiuddin et al. |
| 4,931,045 A | 6/1990 | Steer |
| 4,944,724 A | 7/1990 | Goldberg et al. |
| 4,959,054 A | 9/1990 | Heimke et al. |
| 4,976,688 A | 12/1990 | Rosenblum |
| 5,004,456 A | 4/1991 | Botterbusch et al. |
| 5,060,645 A | 10/1991 | Russell |
| 5,078,689 A | 1/1992 | Keller |
| 5,137,509 A | 8/1992 | Freitas |
| 5,139,485 A | 8/1992 | Smith et al. |
| 5,218,957 A | 6/1993 | Strickland |
| 5,230,332 A | 7/1993 | Strickland |
| 5,230,350 A | 7/1993 | Fentress |
| 5,261,708 A | 11/1993 | Steer |
| 5,263,939 A | 11/1993 | Wortrich |
| 5,312,331 A | 5/1994 | Knoepfler |
| 5,315,992 A | 5/1994 | Dalton |
| 5,336,206 A | 8/1994 | Shichman |
| 5,354,283 A | 10/1994 | Bark et al. |
| 5,356,386 A | 10/1994 | Goldberg et al. |
| 5,366,478 A | 11/1994 | Brinkerhoff et al. |
| 5,370,625 A | 12/1994 | Shichman |
| 5,376,376 A | 12/1994 | Li |
| 5,389,077 A | 2/1995 | Melinyshyn et al. |
| 5,401,262 A | 3/1995 | Karwoski et al. |
| 5,403,264 A | 4/1995 | Wohlers et al. |
| 5,431,633 A * | 7/1995 | Fury ........................... 604/122 |
| 5,478,333 A | 12/1995 | Asherman, Jr. |
| 5,484,401 A | 1/1996 | Rodriguez et al. |
| 5,496,297 A | 3/1996 | Olsen |
| 5,501,677 A | 3/1996 | Jensen |
| 5,501,678 A | 3/1996 | Olsen |
| 5,588,424 A | 12/1996 | Insler et al. |
| 5,616,131 A | 4/1997 | Sauer et al. |
| 5,660,175 A | 8/1997 | Dayal |
| 5,662,629 A | 9/1997 | Steer et al. |
| 5,728,066 A | 3/1998 | Daneshvar |
| 5,730,735 A | 3/1998 | Holmberg et al. |
| 5,738,661 A | 4/1998 | Larice |
| 5,807,341 A | 9/1998 | Heim |
| 5,830,200 A | 11/1998 | Steer et al. |
| 5,843,053 A | 12/1998 | Steer |
| 5,846,836 A * | 12/1998 | Mallow ........................ 436/169 |
| 5,897,531 A | 4/1999 | Amirana |
| 5,931,821 A | 8/1999 | Weilbacher et al. |
| 5,954,636 A | 9/1999 | Schwartz et al. |
| 5,971,962 A | 10/1999 | Kojima et al. |
| 5,972,026 A | 10/1999 | Laufer et al. |
| 6,056,744 A | 5/2000 | Edwards |
| 6,059,816 A | 5/2000 | Moenning |
| 6,083,255 A | 7/2000 | Laufer et al. |
| 6,174,323 B1 | 1/2001 | Biggs et al. |
| 6,197,010 B1 | 3/2001 | Leise, Jr. et al. |
| 6,200,333 B1 | 3/2001 | Laufer |
| 6,258,100 B1 | 7/2001 | Alferness et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,293,930 B1 | 9/2001 | Brunsgaard et al. |
| 6,293,951 B1 | 9/2001 | Alferness et al. |
| 6,299,633 B1 | 10/2001 | Laufer |
| 6,322,536 B1 | 11/2001 | Rosengart et al. |
| 6,328,689 B1 | 12/2001 | Gonzalez et al. |
| 6,330,882 B1 | 12/2001 | French |
| 6,334,441 B1 | 1/2002 | Zowtiak et al. |
| 6,358,269 B1 | 3/2002 | Aye |
| 6,398,775 B1 | 6/2002 | Perkins et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,432,100 B1 | 8/2002 | Affeld |
| 6,443,156 B1 | 9/2002 | Niklason et al. |
| 6,468,292 B1 | 10/2002 | Mollenauer et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,514,290 B1 | 2/2003 | Loomas |
| 6,517,519 B1 | 2/2003 | Rosen et al. |
| 6,520,183 B2 | 2/2003 | Amar |
| 6,527,761 B1 | 3/2003 | Soltesz et al. |
| 6,550,475 B1 | 4/2003 | Oldfield |
| 6,569,121 B1 | 5/2003 | Purow et al. |
| 6,569,166 B2 | 5/2003 | Gonzalez |
| 6,585,639 B1 | 7/2003 | Kotmel et al. |
| 6,589,161 B2 | 7/2003 | Corcoran |
| 6,592,594 B2 | 7/2003 | Rimbaugh et al. |
| 6,599,311 B1 | 7/2003 | Biggs et al. |
| 6,609,521 B1 | 8/2003 | Belani et al. |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,360 B1 | 10/2003 | Flodin |
| 6,634,363 B1 | 10/2003 | Danek et al. |
| 6,638,253 B2 | 10/2003 | Breznock |
| 6,653,525 B2 | 11/2003 | Ingenito et al. |
| 6,659,961 B2 | 12/2003 | Robinson |
| 6,679,264 B1 | 1/2004 | Deem et al. |
| 6,682,506 B1 | 1/2004 | Navarro |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,712,812 B2 | 3/2004 | Roschak et al. |
| 6,736,797 B1 | 5/2004 | Larsen et al. |
| 6,749,606 B2 | 6/2004 | Keast et al. |
| 6,770,063 B2 | 8/2004 | Goldberg et al. |
| 6,770,070 B2 | 8/2004 | Balbierz |
| 6,790,172 B2 | 9/2004 | Alferness et al. |
| 6,827,086 B2 | 12/2004 | Shuman |
| 6,837,906 B2 | 1/2005 | Ginn |
| 6,840,243 B2 | 1/2005 | Deem et al. |
| 6,843,767 B2 | 1/2005 | Corcoran et al. |
| 6,846,292 B2 | 1/2005 | Bakry |
| 6,849,061 B2 | 2/2005 | Wagner |
| 6,852,108 B2 | 2/2005 | Barry et al. |
| 6,860,847 B2 | 3/2005 | Alferness et al. |
| 6,878,141 B1 | 4/2005 | Perkins et al. |
| 6,886,558 B2 | 5/2005 | Tanaka |
| 6,901,927 B2 | 6/2005 | Deem et al. |
| 6,904,909 B2 | 6/2005 | Andreas et al. |
| 6,905,484 B2 * | 6/2005 | Buckman et al. ............. 604/174 |
| 6,905,518 B2 | 6/2005 | Ginn |
| 6,916,310 B2 | 7/2005 | Sommerich |
| 6,929,637 B2 | 8/2005 | Gonzalez et al. |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,014,628 B2 | 3/2006 | Bousquet |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,086,398 B2 | 8/2006 | Tanaka |

| | | | | | |
|---|---|---|---|---|---|
| 7,100,616 B2 | 9/2006 | Springmeyer | 2004/0144387 A1 | 7/2004 | Amar |
| 7,135,010 B2 | 11/2006 | Buckman et al. | 2004/0158228 A1 | 8/2004 | Perkins et al. |
| 7,141,046 B2 | 11/2006 | Perkins et al. | 2004/0167636 A1 | 8/2004 | Dillard et al. |
| 7,165,548 B2 | 1/2007 | Deem et al. | 2004/0173218 A1 | 9/2004 | Yamada et al. |
| 7,172,581 B2 | 2/2007 | Ciok et al. | 2004/0199128 A1 | 10/2004 | Morris et al. |
| 7,175,644 B2 | 2/2007 | Cooper et al. | 2004/0200484 A1 | 10/2004 | Springmeyer |
| 7,182,772 B2 | 2/2007 | Alferness et al. | 2004/0206349 A1 | 10/2004 | Alferness et al. |
| 7,186,259 B2 | 3/2007 | Perkins et al. | 2004/0210248 A1 | 10/2004 | Gordon et al. |
| 7,192,420 B2 | 3/2007 | Whiteford | 2004/0211412 A1 | 10/2004 | Alferness et al. |
| 7,195,016 B2 | 3/2007 | Loyd et al. | 2004/0211434 A1 | 10/2004 | Loomas et al. |
| 7,195,017 B2 | 3/2007 | Tanaka | 2004/0220446 A1 | 11/2004 | Corcoran et al. |
| 7,207,946 B2 | 4/2007 | Sirokman | 2004/0220556 A1 | 11/2004 | Cooper et al. |
| 7,232,414 B2 | 6/2007 | Gonzalez | 2004/0225254 A1 | 11/2004 | Tanaka et al. |
| 7,244,245 B2 | 7/2007 | Purow et al. | 2004/0231674 A1 | 11/2004 | Tanaka |
| 7,252,086 B2 | 8/2007 | Tanaka | 2004/0237966 A1 | 12/2004 | Tanaka |
| 7,377,278 B2 | 5/2008 | Tanaka | 2004/0243140 A1 | 12/2004 | Alferness et al. |
| 7,398,782 B2 | 7/2008 | Tanaka | 2004/0244802 A1 | 12/2004 | Tanaka |
| 7,406,963 B2 | 8/2008 | Chang et al. | 2004/0244803 A1 | 12/2004 | Tanaka |
| 7,426,929 B2 | 9/2008 | Tanaka | 2005/0005936 A1 | 1/2005 | Wondka |
| 7,533,667 B2 | 5/2009 | Tanaka | 2005/0015106 A1 | 1/2005 | Perkins et al. |
| 2001/0025132 A1 | 9/2001 | Alferness et al. | 2005/0022809 A1 | 2/2005 | Wondka |
| 2001/0041906 A1 | 11/2001 | Gonzalez | 2005/0025816 A1 | 2/2005 | Tanaka |
| 2001/0041932 A1 | 11/2001 | Scholz et al. | 2005/0033310 A1 | 2/2005 | Alferness et al. |
| 2002/0042564 A1 | 4/2002 | Cooper et al. | 2005/0033344 A1 | 2/2005 | Dillard et al. |
| 2002/0062120 A1 | 5/2002 | Perkins et al. | 2005/0043745 A1 | 2/2005 | Alferness et al. |
| 2002/0077593 A1 | 6/2002 | Perkins et al. | 2005/0043751 A1 | 2/2005 | Phan et al. |
| 2002/0087153 A1 | 7/2002 | Roschak et al. | 2005/0043752 A1 | 2/2005 | Phan et al. |
| 2002/0111619 A1 | 8/2002 | Keast et al. | 2005/0049615 A1 | 3/2005 | Cooper et al. |
| 2002/0111620 A1 | 8/2002 | Cooper et al. | 2005/0056292 A1 | 3/2005 | Cooper |
| 2002/0112729 A1 | 8/2002 | DeVore et al. | 2005/0060041 A1 | 3/2005 | Phan et al. |
| 2002/0120177 A1 | 8/2002 | Borst et al. | 2005/0060042 A1 | 3/2005 | Phan et al. |
| 2002/0165618 A1 | 11/2002 | Ingenito et al. | 2005/0060044 A1 | 3/2005 | Roschak et al. |
| 2002/0188171 A1 | 12/2002 | Alferness et al. | 2005/0061322 A1 | 3/2005 | Freitag |
| 2003/0013935 A1 | 1/2003 | Alferness et al. | 2005/0066976 A1 | 3/2005 | Wondka |
| 2003/0018344 A1 | 1/2003 | Kaji et al. | 2005/0085801 A1 | 4/2005 | Cooper et al. |
| 2003/0050648 A1 | 3/2003 | Alferness et al. | 2005/0096529 A1 | 5/2005 | Cooper et al. |
| 2003/0051733 A1 | 3/2003 | Kotmel et al. | 2005/0103340 A1 | 5/2005 | Wondka |
| 2003/0055331 A1 | 3/2003 | Kotmel et al. | 2005/0107783 A1 | 5/2005 | Tom et al. |
| 2003/0065339 A1 | 4/2003 | Snyder et al. | 2005/0131276 A1 | 6/2005 | Alferness et al. |
| 2003/0069488 A1 | 4/2003 | Alferness et al. | 2005/0137518 A1 | 6/2005 | Biggs et al. |
| 2003/0078469 A1 | 4/2003 | Corcoran | 2005/0137611 A1 | 6/2005 | Escudero et al. |
| 2003/0083542 A1 | 5/2003 | Alferness et al. | 2005/0137712 A1 | 6/2005 | Biggs et al. |
| 2003/0083671 A1 | 5/2003 | Rimbaugh et al. | 2005/0137715 A1 | 6/2005 | Phan et al. |
| 2003/0127090 A1 | 7/2003 | Gifford et al. | 2005/0145253 A1 | 7/2005 | Wilson et al. |
| 2003/0130593 A1 | 7/2003 | Gonzalez | 2005/0161040 A1 | 7/2005 | Tanaka |
| 2003/0149446 A1 | 8/2003 | Shuman | 2005/0166925 A1 | 8/2005 | Wilson et al. |
| 2003/0154988 A1 | 8/2003 | DeVore et al. | 2005/0171396 A1 | 8/2005 | Pankratov et al. |
| 2003/0158515 A1 | 8/2003 | Gonzalez et al. | 2005/0177144 A1 | 8/2005 | Phan et al. |
| 2003/0163024 A1 | 8/2003 | Corcoran | 2005/0178385 A1 | 8/2005 | Dellaca' et al. |
| 2003/0181356 A1 | 9/2003 | Ingenito | 2005/0178389 A1 | 8/2005 | Shaw et al. |
| 2003/0181922 A1 | 9/2003 | Alferness | 2005/0192526 A1 | 9/2005 | Biggs et al. |
| 2003/0183235 A1 | 10/2003 | Rimbaugh et al. | 2005/0203483 A1 | 9/2005 | Perkins et al. |
| 2003/0186904 A1 | 10/2003 | Ruben et al. | 2005/0205097 A1 | 9/2005 | Kyle |
| 2003/0195385 A1 | 10/2003 | DeVore | 2005/0244401 A1 | 11/2005 | Ingenito |
| 2003/0195511 A1 | 10/2003 | Barry | 2005/0281797 A1 | 12/2005 | Gong et al. |
| 2003/0212337 A1 | 11/2003 | Sirokman | 2005/0281801 A1 | 12/2005 | Gong et al. |
| 2003/0212412 A1 | 11/2003 | Dillard et al. | 2005/0281802 A1 | 12/2005 | Gong et al. |
| 2003/0216730 A1 | 11/2003 | Barry et al. | 2005/0282748 A1 | 12/2005 | Gong et al. |
| 2003/0216769 A1 | 11/2003 | Dillard et al. | 2005/0288549 A1 | 12/2005 | Mathis |
| 2003/0228344 A1 | 12/2003 | Fields et al. | 2005/0288550 A1 | 12/2005 | Mathis |
| 2003/0233099 A1 | 12/2003 | Danaek et al. | 2005/0288684 A1 | 12/2005 | Aronson et al. |
| 2004/0010209 A1 | 1/2004 | Sirokman | 2005/0288702 A1 | 12/2005 | McGurk et al. |
| 2004/0010289 A1 | 1/2004 | Biggs et al. | 2006/0004400 A1 | 1/2006 | McGurk et al. |
| 2004/0016435 A1 | 1/2004 | Deem et al. | 2006/0009748 A1 | 1/2006 | Mathis |
| 2004/0024356 A1 | 2/2004 | Tanaka | 2006/0025815 A1 | 2/2006 | McGurk et al. |
| 2004/0031494 A1 | 2/2004 | Danek et al. | 2006/0047291 A1 | 3/2006 | Barry |
| 2004/0040555 A1 | 3/2004 | Tanaka | 2006/0076023 A1 | 4/2006 | Rapacki et al. |
| 2004/0047855 A1 | 3/2004 | Ingenito | 2006/0079838 A1 | 4/2006 | Walker et al. |
| 2004/0055606 A1 | 3/2004 | Hendricksen et al. | 2006/0095002 A1 | 5/2006 | Soltesz et al. |
| 2004/0059263 A1 | 3/2004 | DeVore et al. | 2006/0107961 A1 | 5/2006 | Tanaka |
| 2004/0073155 A1 | 4/2004 | Laufer et al. | 2006/0116749 A1 | 6/2006 | Willink et al. |
| 2004/0073191 A1 | 4/2004 | Soltesz et al. | 2006/0118125 A1 | 6/2006 | Tanaka |
| 2004/0073201 A1 | 4/2004 | Cooper et al. | 2006/0118126 A1 | 6/2006 | Tanaka |
| 2004/0073241 A1 | 4/2004 | Barry et al. | 2006/0124126 A1 | 6/2006 | Tanaka |
| 2004/0078026 A1 | 4/2004 | Wagner | 2006/0130830 A1 | 6/2006 | Barry |
| 2004/0078054 A1 | 4/2004 | Biggs et al. | 2006/0135947 A1 | 6/2006 | Soltesz et al. |
| 2004/0087831 A1 | 5/2004 | Michels et al. | 2006/0135984 A1 | 6/2006 | Kramer et al. |
| 2004/0097983 A1 | 5/2004 | Snyder et al. | 2006/0142672 A1 | 6/2006 | Keast et al. |
| 2004/0143282 A1 | 7/2004 | Dillard et al. | 2006/0161233 A1 | 7/2006 | Barry et al. |

| | | | |
|---|---|---|---|
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1 | 3/2007 | Tanaka | |
| 2007/0055175 A1 | 3/2007 | Caro | |
| 2007/0088300 A1 | 4/2007 | Cline et al. | |
| 2007/0123922 A1 | 5/2007 | Cooper et al. | |
| 2007/0128174 A1 | 6/2007 | Kleinsek et al. | |
| 2007/0142742 A1 | 6/2007 | Aljuri et al. | |
| 2007/0163598 A1 | 7/2007 | Chang et al. | |
| 2007/0185531 A1 | 8/2007 | Rimbaugh et al. | |
| 2007/0186932 A1 | 8/2007 | Wondka et al. | |
| 2007/0186933 A1 | 8/2007 | Domingo et al. | |
| 2007/0299424 A1 | 12/2007 | Cumming et al. | |
| 2008/0281151 A1 | 11/2008 | Chang et al. | |
| 2008/0281295 A1 | 11/2008 | Chang et al. | |
| 2008/0281433 A1 | 11/2008 | Chang et al. | |
| 2008/0283065 A1 | 11/2008 | Chang et al. | |
| 2008/0287878 A1 | 11/2008 | Tanaka | |
| 2008/0287973 A1 | 11/2008 | Aster et al. | |
| 2008/0295829 A1 | 12/2008 | Evens | |
| 2009/0205641 A1 | 8/2009 | Tanaka | |
| 2009/0205643 A1 | 8/2009 | Tanaka et al. | |
| 2009/0205644 A1 | 8/2009 | Tanaka et al. | |
| 2009/0205645 A1 | 8/2009 | Tanaka et al. | |
| 2009/0205646 A1 | 8/2009 | Tanaka et al. | |
| 2009/0205647 A1 | 8/2009 | Plough et al. | |
| 2009/0205648 A1 | 8/2009 | Tanaka et al. | |
| 2009/0205649 A1 | 8/2009 | Tanaka et al. | |
| 2009/0205650 A1 | 8/2009 | Tanaka et al. | |
| 2009/0205651 A1 | 8/2009 | Tanaka et al. | |
| 2009/0205658 A1 | 8/2009 | Tanaka et al. | |
| 2009/0205665 A1 | 8/2009 | Tanaka et al. | |
| 2009/0209856 A1 | 8/2009 | Tanaka et al. | |
| 2009/0209906 A1 | 8/2009 | Tanaka et al. | |
| 2009/0209909 A1 | 8/2009 | Tanaka et al. | |
| 2009/0209917 A1 | 8/2009 | Tanaka et al. | |
| 2009/0209924 A1 | 8/2009 | Tanaka | |
| 2009/0209936 A1 | 8/2009 | Tanaka et al. | |
| 2009/0209970 A1 | 8/2009 | Tanaka et al. | |
| 2009/0209971 A1 | 8/2009 | Tanaka et al. | |
| 2011/0232646 A1* | 9/2011 | Ho et al. | 128/206.24 |

FOREIGN PATENT DOCUMENTS

| | | |
|---|---|---|
| EP | 1358904 | 5/2003 |
| EP | 1658867 | 5/2006 |
| EP | 1815821 | 8/2007 |
| EP | 2242527 | 10/2010 |
| JP | 62-2028747 U | 6/1986 |
| JP | 2000197706 | 7/2000 |
| RU | 2192185 | 10/2002 |
| WO | WO 96/39960 | 12/1996 |
| WO | WO 99/66975 | 12/1999 |
| WO | WO 00/76577 A1 | 12/2000 |
| WO | WO 01/45568 A1 | 6/2001 |
| WO | WO2005070480 | 8/2005 |

OTHER PUBLICATIONS

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&lng=e...> May 2, 2007.

Shah, Pallav, "Surgical and Non-surgical Volume Reduction for COPD", Presented at the Clinical Consensus on COPD, Mar. 2-3, 2007, Novotel London West, 56 pages; see p. 55 of 56.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woodring et al., "Pneumothorax ex vacuo", Chest 1996, 110: 1102-1124.

Woolcock et al., "Mechanical factors influencing collateral ventilation in human, dog, and pig lungs", Journal of Applied Physiology 1971, 30: 99-115.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.

International Search Report for PCT/US2009/034322 dated Oct. 5, 2009; 14 pages.

International Search Report for PCT/US2009/034406 dated Dec. 2, 2009; 16 pages.

Aljuri et al., "Validation and pilot clinical study of a new bronchoscopic method to measure collateral ventilation before endobronchial lung volume reduction", J Appl Physio 106: 774-783, 2009.

Al-Salem et al., "Computed tomography-guided percutaneous needle aspiration of lung abscesses in neonates and children", Pediatr Surg Int (1997) 12: 417-419, copyright Springer-Verlag 1997.

Ball, JR et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.

Brenner et al., "Innovative Approaches to Lung Volume Reduction for Emphysema", Chest 2004; 126: 238-248.

Brutinel et al., "A two-year experience with the neodymium-YAG laser in endobronchial obstruction", Chest 1987; 91: 159-165.

Celli et al. "Standards for the diagnosis and treatment of patients with COPD: a summary of the ATS/ERS position paper", European Respiratory Journal 2004; 23; 932-946.

Cetti et al., "Collateral ventilation", Thorax 2006; 61: 371-373.

Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System.

Choong et al., "Feasibility and safety of airway bypass stent placement and influence of topical mitomycin C on stent patency", The Journal of Thoracic and Cardiovascular Surgery 2005; 129: 632-638.

Choong et al., "Transpleural ventilation of explanted human lungs", Thorax 2007; 62: 623-630; originally published online Apr. 5, 2007.

Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.

Dumon, J. F., "A Dedicated Tracheobronchial Stent", Chest 1990; 97: 328-332.

Eloesser, "An Operation for Tuberculous Empyema", Chest 1935; 1: 8-23.

Fein, Alan M, "Lung Volume Reduction Surgery: Answering the Crucial Questions", Chest 1998; 113: 277-282.

Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.

Fessler, Henry E., "Collateral Ventilation, the Bane of Bronchoscopic Volume Reduction", Am J Respir Crit Care Med 2005; 171: 423-425.

Frawley et al., "Airway Pressure Release Ventilation: Theory and Practice", AACN Clinical Issues 2001; vol. 12, No. 2: 234-246.

Freitag et al., "Theoretical and experimental basis for the development of a dynamic airway stent", European Respiratory Journal 1994; 7: 2038-2045.

Ghaye et al., "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.

Goldstraw et al., "The Surgical Treatment of Emphysema: The Brompton Approach", Chest Surgery Clinics of North America Nov. 1995; vol. 5, No. 4: 777-797.

Habashi, Nader M., "Other approaches to open-lung ventilation: Airway pressure release ventilation", Crit Care Med 2005, vol. 33, No. 3 (Suppl): S228-S240.

Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.

Heimlich, Henry J., "Respiratory Rehabilitation with Transtracheal Oxygen System", Ann Otol Rhinol Laryngol Nov./Dec. 1982; 91: 643-647.

Hogg et al., "Chronic obstructive pulmonary disease c2: Pathology and biochemistry of emphysema", Thorax 2002; 57: 830-834.

Hogg et al., "The Resistance of Collateral Channels in Excised Human Lungs", Journal of Clinical Investigation 1969; 48: 421-431.

Joannette, Albert, "Drainage of Tuberculous Cavities by Aspiration (Monaldi Method)", The Canadian Medical Association Journal Jan. 1941; 46-48.

Korpela et al., "Bioabsorbable Self-reinforced Poly-L-Lactide, Metallic, and Silicone Stents in the Management of Experimental Tracheal Stenosis", Chest 1999; 115: 490-495.

Lausberg et al., "Bronchial Fenestration Improves Expiratory Flow in Emphysematous Human Lungs", Annals of Thoracic Surgery 2003; 75: 393-398.

Lorenzo et al., "Lung Abscesses in Children: Diagnostic and Therapeutic Needle Aspiration", Radiology Oct. 1985; 157: 79-80.

MacArthur et al., "Intracavity suction and drainage in the treatment of emphysematous bullae", Thorax 1977; 32: 668-672.

Macklem, Peter T., "Collateral Ventilation", The New England Journal of Medicine Jan. 5, 1978; 298(1): 49-50.

Matson et al., "Evaluation of Various Surgical Procedures in the Treatment of Pulmonary Tuberculosis", Chest 1946; 12: 40-47.

McCoy, Robert, "Oxygen-Conserving Techniques and Devices", Respiratory Care Jan. 2000, vol. 45, No. 1: 95-104.

Meyers et al., "Chronic obstructive pulmonary disease 10: Bullectomy, lung volume reduction surgery, and transplantation for patients with chronic obstructive pulmonary disease", Thorax 2003; 58: 634-638.

Mineo et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

Extended European Search Report dated Jun. 22, 2011 for PCT/US2009034374, 7 pages.

Extended European Search Report dated Jun. 15, 2011 for PCT/US2009034322, 7 pages.

Extended European Search Report dated Sep. 16, 2011 for PCT/US2009034380, 8 pages.

* cited by examiner

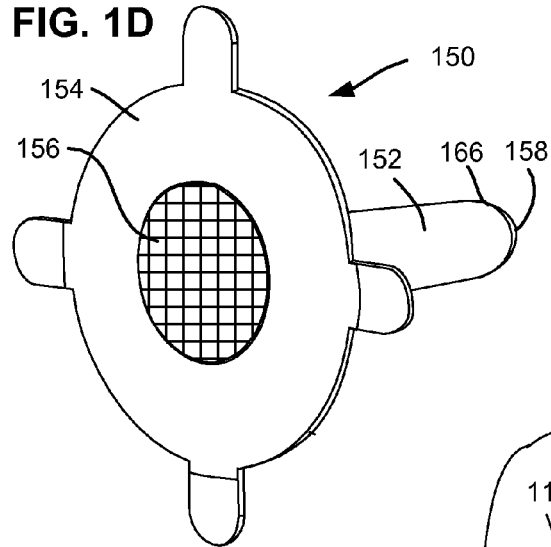
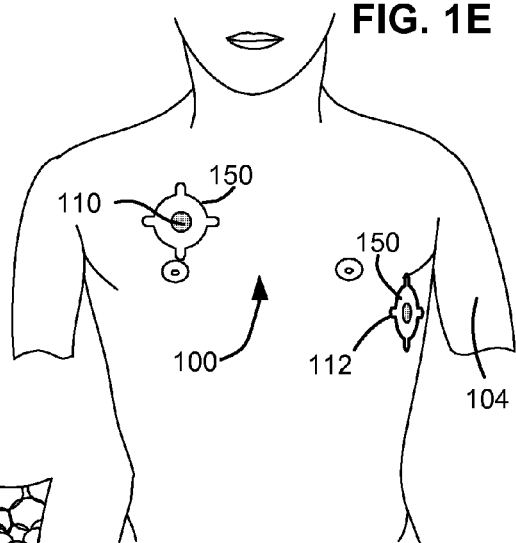
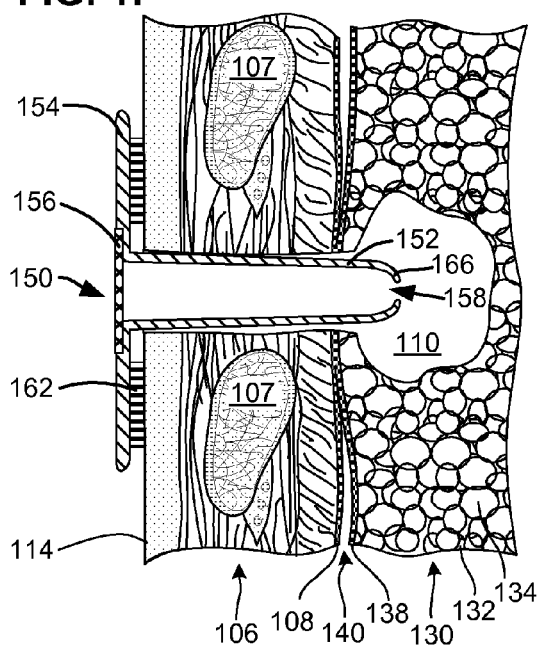

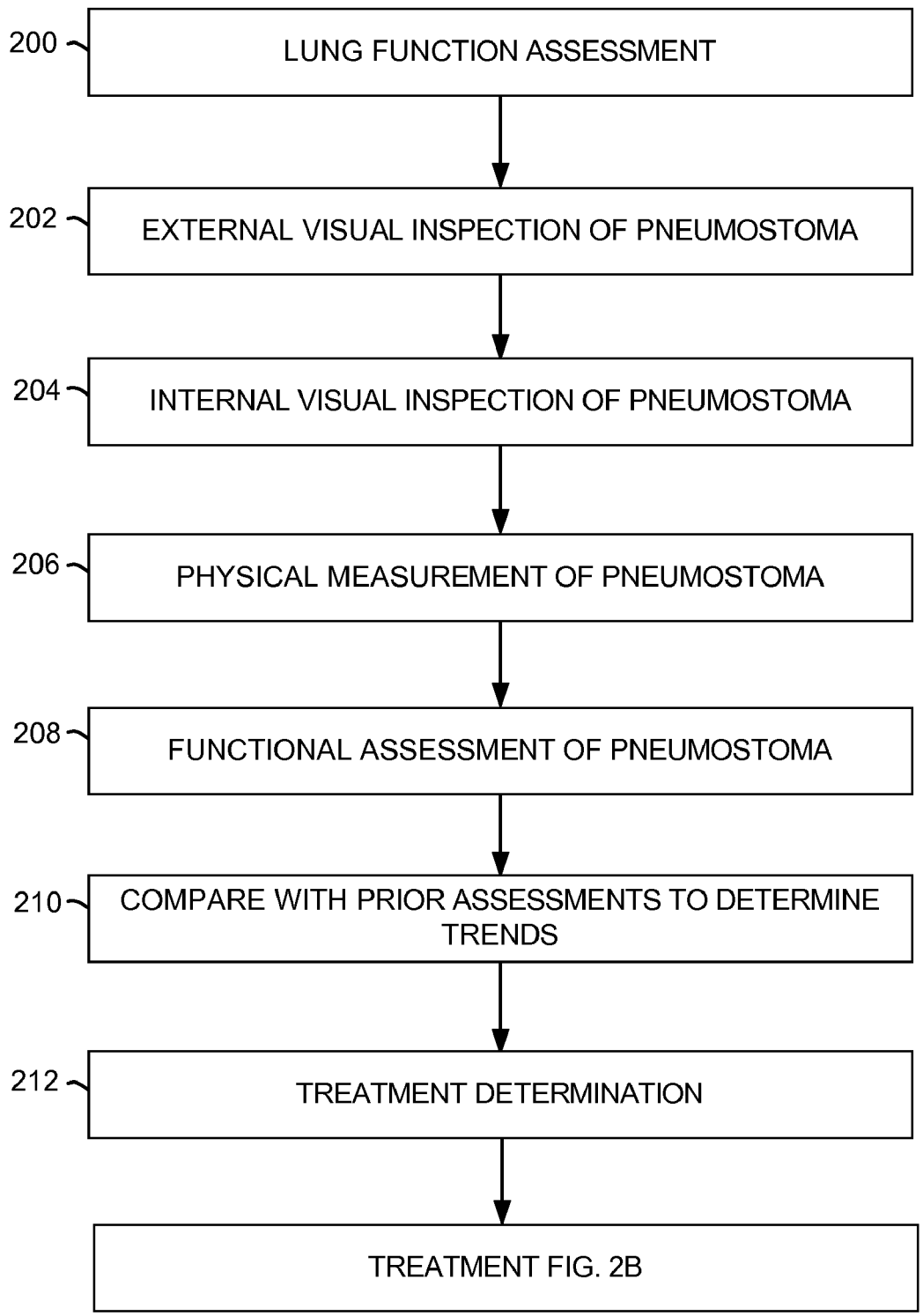

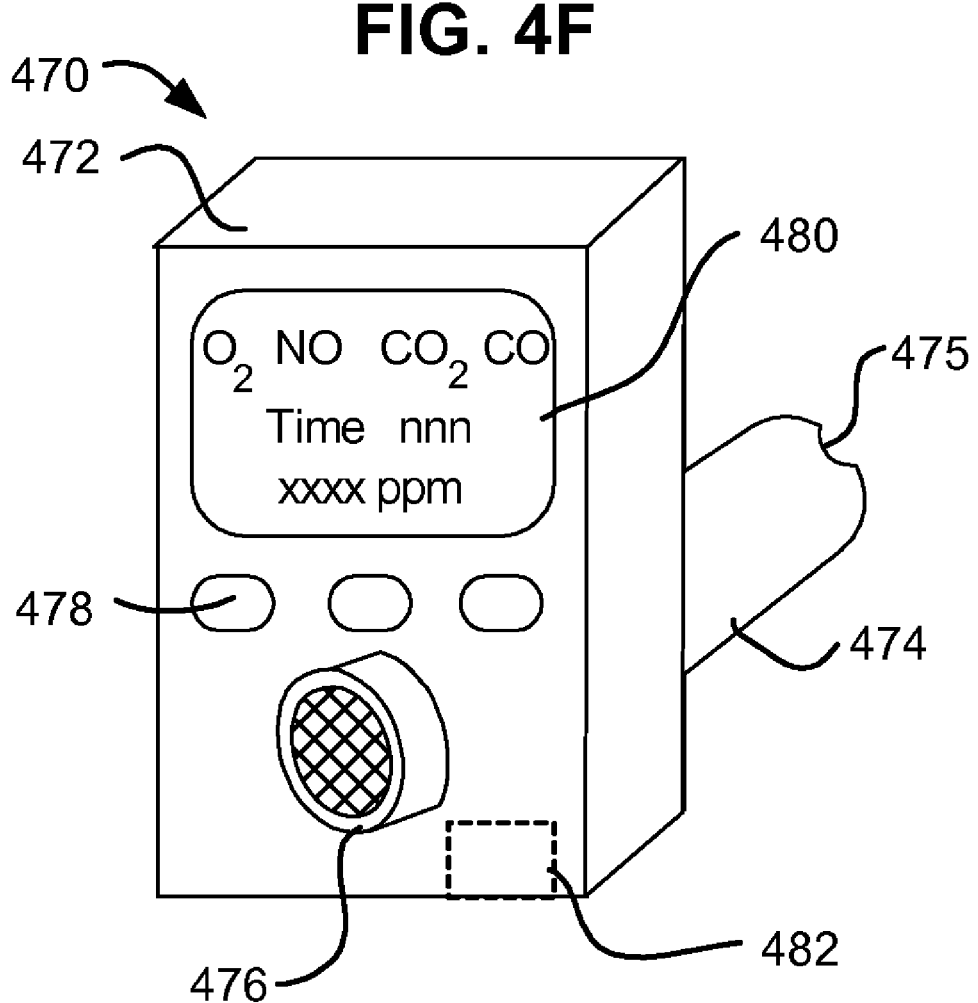

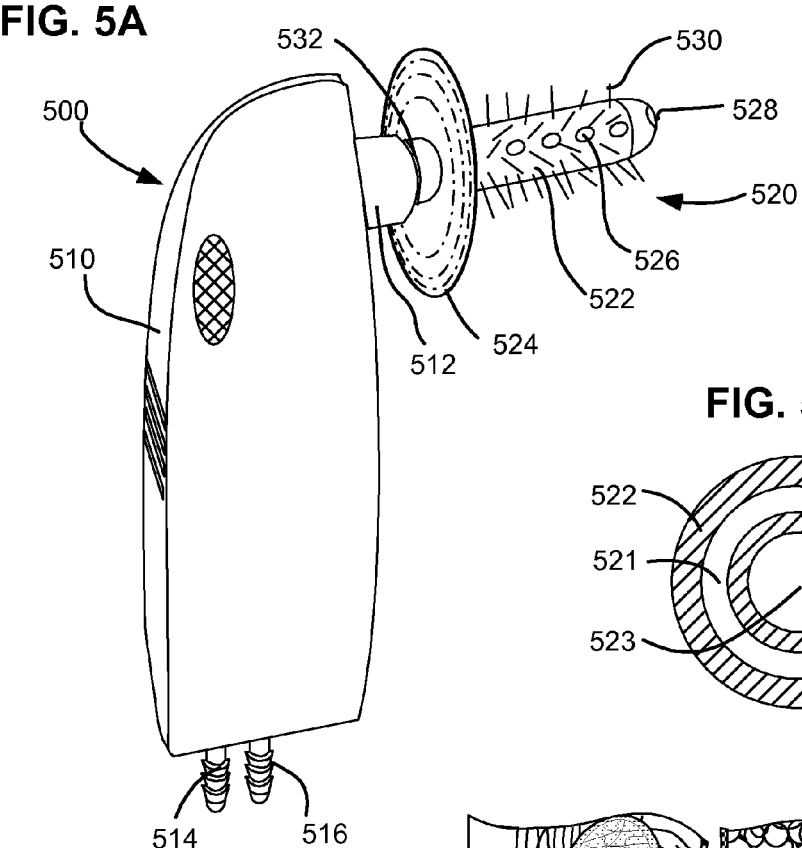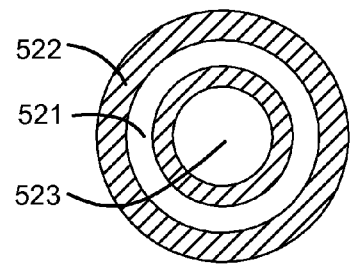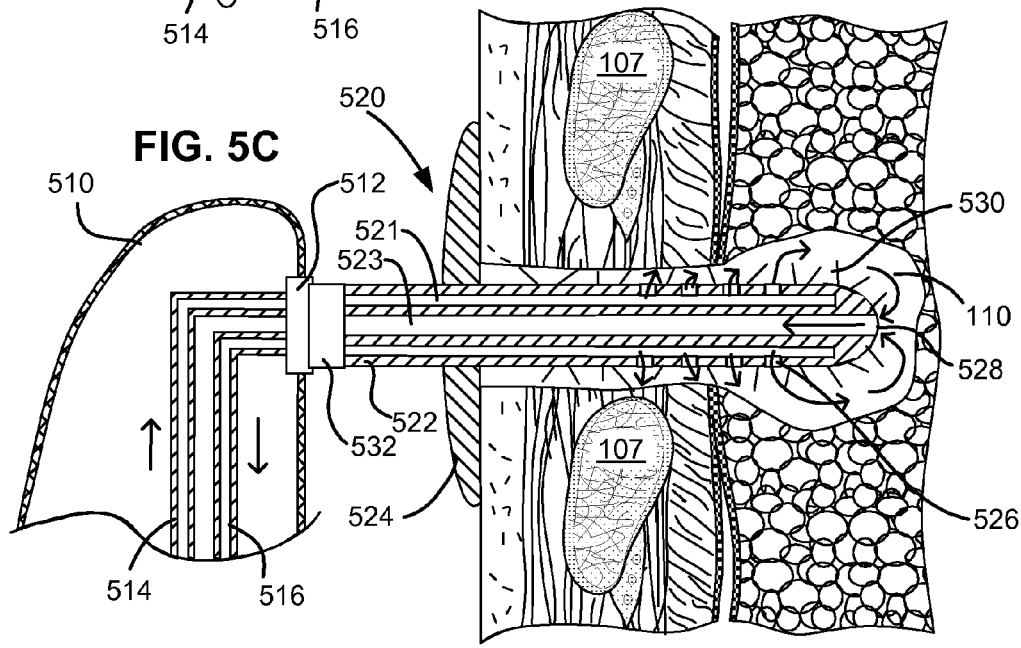

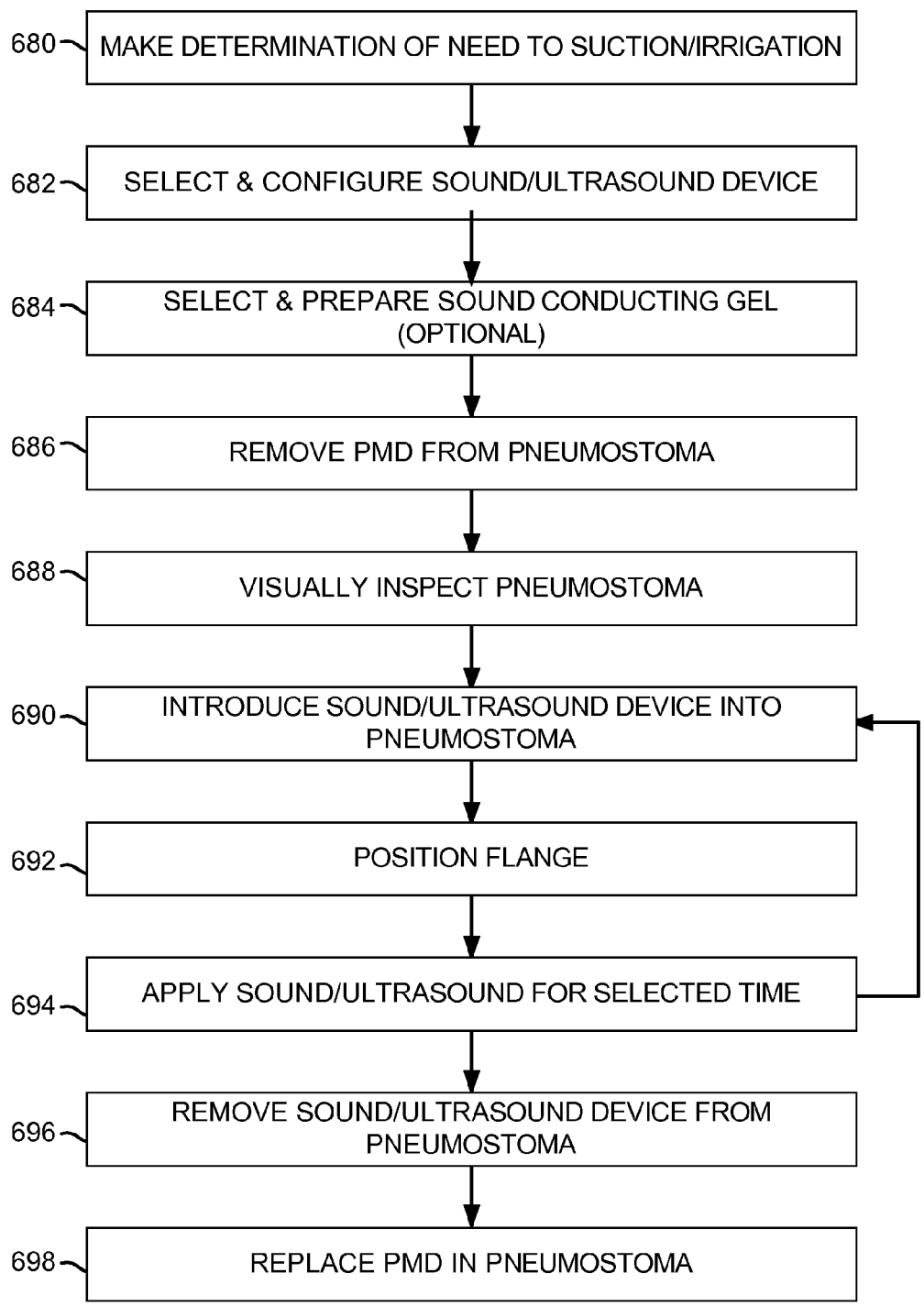

FIG. 7C
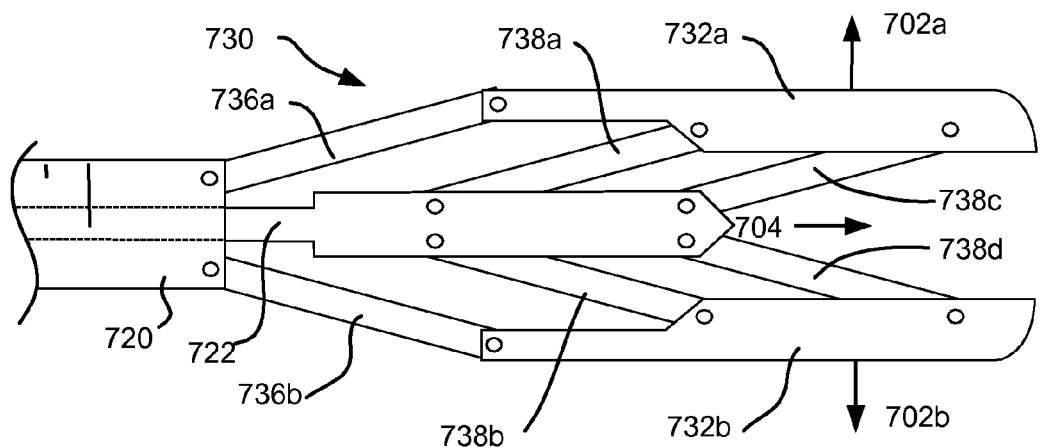
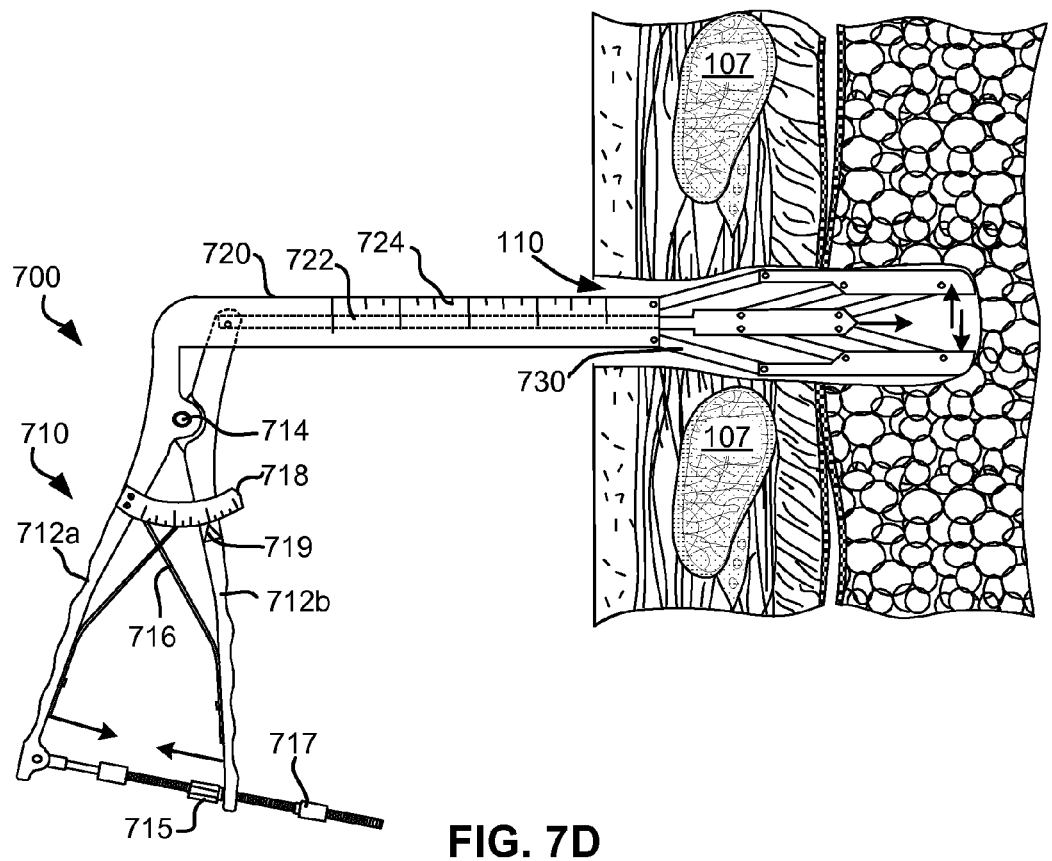
FIG. 7D

FIG. 9C
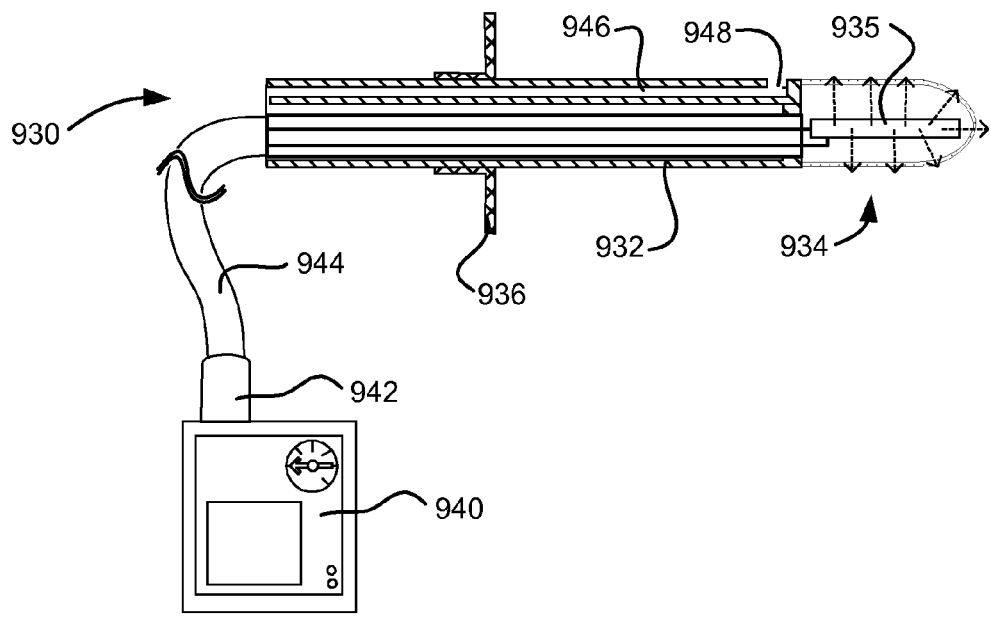
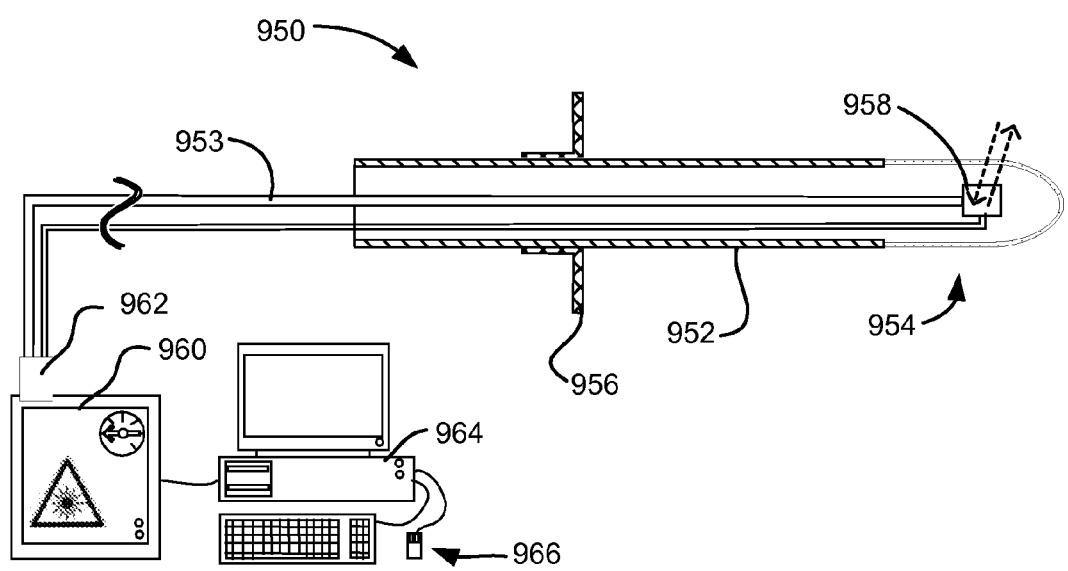
FIG. 9D

PNEUMOSTOMA MANAGEMENT DEVICE WITH INTEGRATED PATENCY SENSOR AND METHOD

CLAIM TO PRIORITY

This application claims priority to all of the following applications including:

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,446, filed Feb. 18, 2009, entitled "PERCUTANEOUS SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,453, filed Feb. 18, 2009, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,460, filed Feb. 13, 2009, entitled "PNEUMOSTOMA MANAGEMENT SYSTEM HAVING A COSTMETIC AND/OR PROTECTIVE COVER"

U.S. patent application Ser. No. 12/388,455 filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, entitled "ASPIRATOR FOR PNEUMOSTOMA MANAGEMENT";

U.S. patent application Ser. No. 12/388,462, filed Feb. 18, 2009, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, entitled "MULTI-LAYER PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE"; and U.S. patent application Ser. No. 12/388,470, filed Feb. 18, 2009, entitled "SELF-SEALING DEVICE AND METHOD FOR DELIVERY OF A THERAPEUTIC AGENT THROUGH A PNEUMOSTOMA".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), and hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments for ameliorating the symptoms. The goal of current treatments is to help people live with the disease more comfortably and to prevent the progression of the disease. The current options include: self-care (e.g., quitting smoking), therapeutic agents (such as bronchodilators which do not address emphysema physiology), long-term oxygen therapy, and surgery (such as lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure and thus have no viable surgical options.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are unproven. None of the surgical approaches to treatment of COPD has been widely adopted. Therefore, a large unmet need remains for a medical procedure that can sufficiently alleviate the debilitating effects of COPD and emphysema.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by pleurodesis between the visceral and parietal membranes surrounding the passageway as it enters the lung. The pleurodesis creates an adhesion between the pleural membrane surrounding the passageway which prevents air from entering the pleural cavity and causing a pneumothorax (deflation of the lung due to air pressure in the pleural cavity). Pleurodesis results from a fibrotic healing response between the pleural membranes and may be localized to the vicinity of the passageway. The artificial passageway through the chest wall also becomes epithelialized. The result is a relatively stable artificial aperture through the chest wall which communicates with the parenchymal tissue of the lung.

The artificial aperture into the lung through the chest is referred to herein as a pneumostoma. The pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort, reduces expiratory pressures, reduces dyspnea, and allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide. Reducing the amount of carbon dioxide retained in the lung reduces hypercapnia which also reduces dyspnea. The pneumostoma thereby achieves the advantages of lung volume reduction surgery without surgically removing or sealing off a portion of the lung or transplanting a lung.

The present invention provides methods and devices for assessing, and treating the health and functionality of a pneumostoma. Utilizing the methods and devices of the present invention a physician can enhance the health, patency and/or effectiveness of a pneumostoma thereby enhancing the remediation of COPD. Other objects, features and advantages of the invention are apparent from drawings and detailed description to follow.

BRIEF DESCRIPTION OF THE DRAWINGS

The above and further features, advantages and benefits of the present invention are apparent upon consideration of the present description taken in conjunction with the accompanying drawings.

FIG. 1D shows a perspective view of a pneumostoma management device.

FIG. 1E shows the chest of a patient showing the pneumostoma management device positioned at alternative pneumostoma locations.

FIG. 1F shows a detailed sectional view of a pneumostoma management device positioned inside a pneumostoma.

FIG. 2A is a flow chart illustrating general steps for follow-up care and assessment of a patient having a pneumostoma according to an embodiment of the invention.

FIG. 4F shows a perspective view of a home gas analysis unit according to an embodiment of the present invention.

FIGS. 5A-5C show views of a device for cleaning and treating the pneumostoma according to an embodiment of the invention.

FIG. 6C is a flow chart illustrating steps for treatment of a pneumostoma with sound and/or ultrasound according to an embodiment of the invention.

FIGS. 7A-7D show views of a mechanical instrument for dilating the pneumostoma or a portion of the pneumostoma according to an embodiment of the present invention.

FIG. 9C shows a view of an alternate electromagnetic treatment device for treating tissues of the pneumostoma according to an embodiment of the present invention.

FIG. 9D shows a view of an alternate electromagnetic treatment device for treating tissues of the pneumostoma according to an embodiment of the present invention.

DETAILED DESCRIPTION OF THE INVENTION

Figure 1A:
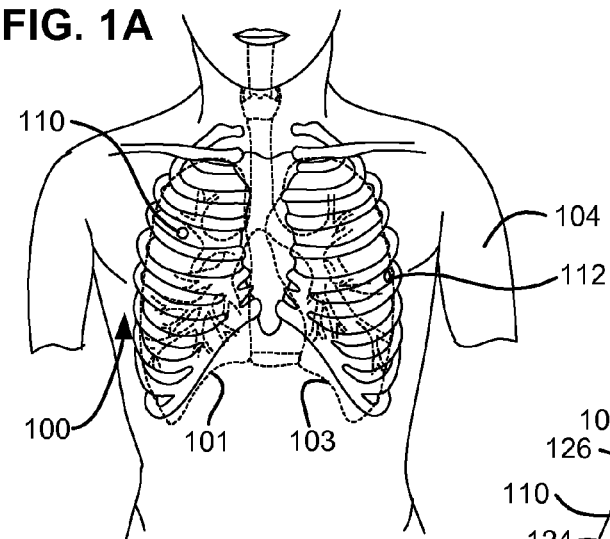
FIG. 1A shows the chest of a patient indicating alternative locations for a pneumostoma that may be managed using the devices and methods of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators are used to refer to like parts or elements throughout. In addition, the first digit of a reference number identifies the drawing in which the reference number first appears.

Pneumostoma Formation and Anatomy

FIG. 1A shows the chest of a patient identifying alternative locations for creating a pneumostoma that may be managed using the system of the present invention. A first pneumostoma 110 is shown on the front of the chest 100 over the right lung 101 (shown in dashed lines). The pneumostoma is preferably positioned over the third intercostal space on the midclavicular line. Thus the pneumostoma 110 is located on the front of the chest between the third and fourth ribs. Although the pneumostoma 110 is preferably located between two ribs, in alternative procedures a pneumostoma can also be prepared using a minithoracotomy with a rib resection.

In FIG. 1A a second pneumostoma 112 is illustrated in a lateral position entering the left lung 103 (shown in dashed lines). The pneumostoma 112 is preferably positioned over the fourth or fifth intercostal space under the left arm 104. In general, one pneumostoma per lung is created; however, more or less than one pneumostoma per lung may be created depending upon the needs of the patient. In most humans, the lobes of the lung are not completely separate and air may pass between the lobes. The upper lobe is the preferred location for a pneumostoma as the upper lobe tends to move less during breathing. However depending upon the patient, it may be desirable to position a pneumostoma in any one of the lobes of the lung including the lower lobes.

A pneumostoma is surgically created by forming an artificial channel through the chest wall and joining that channel with an opening through the visceral membrane of the lung into parenchymal tissue of the lung to form an anastomosis. The anastomosis is joined and sealed by sealing the channel from the pleural cavity using adhesives, mechanical sealing and/or pleurodesis.

Figure 1B:
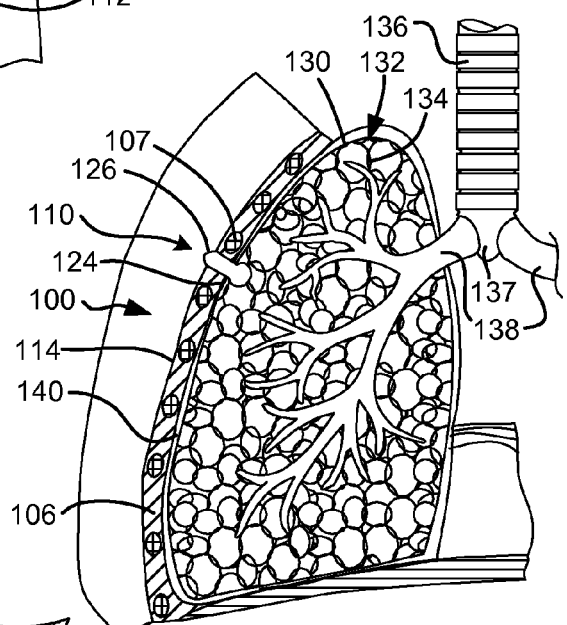
FIG. 1B shows a sectional view of the chest illustrating the relationship between the pneumostoma, lung and natural airways.

FIG. 1B shows a sectional view of chest 100 illustrating the position of the pneumostoma 110. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 138. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100.

Figure 1C:
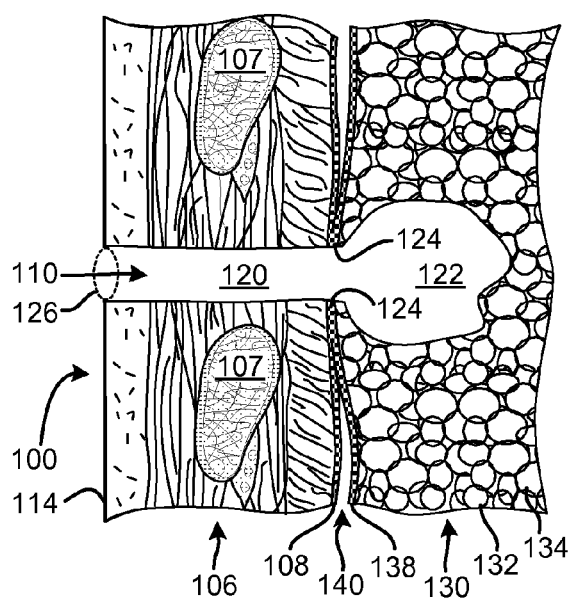
FIG. 1C shows a detailed sectional view of a pneumostoma.

FIG. 1C shows a detailed sectional view of the pneumostoma 110. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. The cavity 122 will typically conform to the shape of the device inserted into the pneumostoma 110. An adhesion or pleurodesis 124 surrounds the channel 120 where it enters the lung 130. The thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. In pleurodesis 124 the pleural membranes are fused and/or adhered to one another eliminating the space between the pleural membranes in that region.

An important feature of the pneumostoma is the seal or adhesion 124 surrounding the channel 120 where it enters the lung 130 which may be formed by pleurodesis. Pleurodesis creates a fusion or adhesion 124 of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the adhesion 124 is preferably localized to the region surrounding the channel 120. The adhesion 124 surrounding the channel 120 prevents air from entering the pleural cavity 140. If air is permitted to enter pleural cavity 140, a pneumothorax will result and the lung may collapse.

Adhesion 124 can be created between the visceral pleura of the lung and the inner wall of the thoracic cavity using chemical methods including introducing into the pleural space irritants such as antibiotics (e.g. Doxycycline or Quinacrine), antibiotics (e.g. iodopovidone or silver nitrate), anticancer therapeutic agents (e.g. Bleomycin, Mitoxantrone or Cisplatin), cytokines (e.g. interferon alpha-2β and Transforming growth factor-β); pyrogens (e.g. *Corynebacterium parvum*, *Staphylococcus aureus* superantigen or OK432); connective tissue proteins (e.g. fibrin or collagen) and minerals (e.g. talc slurry). Pleurodesis can also be performed using surgical methods including pleurectomy. For example, the pleural space may be mechanically abraded during thoracoscopy or thoracotomy. This procedure is called dry abrasion pleurodesis. A pleurodesis may also be formed using radiotherapy methods, including radioactive gold or external radiation. These methods cause an inflammatory response and or fibrosis, healing, and fusion of the pleural membranes. Alternatively, a seal can be created in an acute manner between the pleural membranes using biocompatible glues, meshes or mechanical means such as clamps, staples, clips and/or sutures. The adhesive or mechanical seal may develop cause pleurodesis over time. A range of biocompatible glues are available that may be used on the lung, including light-activatable glues, fibrin glues, cyanoacrylates and two part polymerizing glues.

When formed, pneumostoma 110 provides an extra pathway for exhaled air to exit the lung 130 reducing residual volume and intra-thoracic pressure without the air passing through the major natural airways such as the bronchi 138 and trachea 136. Collateral ventilation is particularly prevalent in an emphysemous lung because of the deterioration of lung tissue caused by COPD. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110 thus makes use of collateral ventilation to collect air in cavity 122 and vent the air outside the body via channel 120 reducing residual volume and intra-thoracic pressure and bypassing the natural airways which have been impaired by COPD and emphysema. Cavity 122 will typically conform/adapt to the size and shape of the device inserted into the pneumostoma.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Pneumostoma 110 thus achieves many of the advantages sought by lung volume reduction surgery without surgically removing a portion of the lung or sealing off a portion of the lung.

Methods and instruments for forming the channel, opening, anastomosis and pleurodesis are disclosed in applicant's pending and issued patents and applications including those related cases incorporated by reference above.

Pneumostoma Management Device

As described above, a pneumostoma may be created to treat the symptoms of chronic obstructive pulmonary disease. A patient is typically provided with a pneumostoma management system to protect the pneumostoma and keeps the pneumostoma open on a day-to-day basis. In general terms a pneumostoma management device ("PMD") comprises a tube which is inserted into the pneumostoma and an external component which is secured to the skin of the patient to keep the tube in place. Gases escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube. FIGS. 1D, 1E and 1F show an example of pneumostoma management device ("PMD") 150. FIG. 1D shows a perspective view of PMD 150. FIG. 1E shows a view of the chest of a patient showing PMD 150 positioned in pneumostomas. FIG. 1F shows a sectional view of PMD 150 positioned within pneumostoma 110.

Referring to FIG. 1D, PMD 150 includes a vent tube 152, a flange 154 and a filter 156. Filter 156 prevents liquid and solid discharge from leaking out of the PMD and such discharge is trapped inside the pneumostoma or vent tube until the PMD is removed and replaced. Filter 156 also prevents the entry of contaminants into the pneumostoma. Filter 156 is preferably a hydrophobic filter to prevent leakage of fluids into or out of the pneumostoma. Flange 154 has an adhesive coating 162 (not shown) on the distal side. The adhesive coating 162 temporarily secures flange 154 to the skin 114 of the patient. Flange 154 also prevents over insertion of vent tube 152 by providing a mechanical stop to further insertion.

As shown in FIGS. 1E and 1F, during use, the vent tube 152 of PMD 150 is pushed into the pneumostoma 110. The vent tube is configured to fit into a pneumostoma to keep the pneumostoma open. Gases from the lung enter an opening 158 in the distal end of vent tube 152. Vent tube 152 is sized so as to pass through the thoracic wall into a portion of the pneumostoma 110 within the lung 130 as shown in FIG. 1F. However, vent tube 152 but is not so long that it causes damage to the parenchymal tissue 132 of the lung 130. Vent tube 152 is preferably rounded over to provide an atraumatic tip 166 at the distal end. A patient is provided with a PMD having a vent tube 152 of the appropriate length for their pneumostoma. When the patient exhales, the pressure inside the chest is above atmospheric pressure and gases are consequently pushed through the central lumen of vent tube 152 and out through filter 156. Additional details and variations of pneumostoma management devices are described in applicant's pending and issued patents and applications including those related cases incorporated by reference above.

Pneumostoma Follow-Up Care

The patient is typically responsible for day-to-day management of the pneumostoma including replacement of the PMD and whatever daily cleaning and skin care may be required. In preferred embodiments, the PMD is a disposable unit which is changed on a daily basis or as needed. While changing the PMD, the patient and/or caregiver can clean the skin surrounding the pneumostoma and observe the condition of the pneumostoma.

A patient with a pneumostoma is also under the care of a physician and undergoes periodic checkups to monitor the condition of their lungs and of the pneumostoma. Moreover, the patient is advised to visit the physician if certain conditions are observed. The patient therefore visits the physician for regular follow-up visits and as indicated by observed conditions. The patient will also preferably be enrolled in a pulmonary rehabilitation program which will include: medical evaluation and management including monitoring patient compliance with pneumostoma care procedures; setting short term and long-term exercise goals; therapy programs (including smoking cessation if necessary); evaluation; and exercise. The rehabilitation program can also monitor the pneumostoma and refer the patient for assessment and treatment of the pneumostoma where indicated.

The present invention provides a number of methods and devices for pneumostoma assessment and treatment. Such assessment and treatment is typically carried by a medical professional, for example a physician, nurse, respiratory therapist and/or medical assistant (this patent will use the term physician to include other medical care providers). FIG. 2A shows general assessment steps that may be performed when a patient visits a physician. The physician will typically assess the lung function of the patient (step 200). The physician will also assess each pneumostoma of the patient. The assessment of the pneumostoma may include one or more of an external visual inspection of the pneumostoma (step 202), an internal visual inspection of the pneumostoma (step 204); physical measurement of the pneumostoma (step 206), and a functional assessment of the pneumostoma (step 208). The results of the assessments may be compared with standard results and with prior assessments of the patient (step 210) to determine trends and variations in the lung/pneumostoma function. Based on the assessment of the lung function and pneumostoma, the physician determines whether any follow-up assessments and/or treatments are required (step 212).

The assessment of lung function (step 200) is performed as is typically done for COPD and emphysema patients. Such assessment may utilize one or more of: patient questionnaire/self reporting, spirometry (pre-/post-bronchodilator), pulmonary function test (lung volumes), diffusion capacity (DLLO), and arterial blood gas measurement.

In the external visual inspection (step 202) the physician examines the opening to the pneumostoma and the skin of the chest surrounding the pneumostoma. The physician observes any irritation, inflammation or infection and remediates where necessary. In the internal visual inspection (step 204) the physician examines the inside of the pneumostoma. The physician may use a pneumostoma inspection instrument. The pneumostoma inspection instrument includes a short inspection tube that may be pushed into the pneumostoma and that provides illumination and magnification for observation of the interior of the pneumostoma. The observation may be achieved using a direct optical train or a video device which displays images on a video display. The pneumostoma inspection instrument is typically provided with a range of inspection tubes of different diameters and lengths. The physician chooses the inspection tube appropriate to the dimensions of the pneumostoma of the patient and is careful not to damage tissue of the pneumostoma during insertion. During the internal visual inspection the physician observes any irritation, inflammation or infection and remediates where necessary. The physician also makes a qualitative assessment of tissues surrounding the pneumostoma to determine encroachment to the pneumostoma. The physician may also use the pneumostoma inspection instrument to measure the diameter and length of the pneumostoma and the shape and/or profile of the pneumostoma. (step 206). These may be used to determine the size of any pneumostoma management device prescribed to the patient and the size of any instruments to be used during treatment of the pneumostoma. This step also allows the physician to monitor any tissue encroachment into the pneumostoma as indicated by change in dimensions of the pneumostoma over time.

In the functional assessment of the pneumostoma (step 208) the physician examines the ability of gas to pass through the pneumostoma. The ability of gas to pass through the pneumostoma may be measured in a number of ways. First, gas flow through the pneumostoma can be measured passively by placing a device over the pneumostoma which measures airflow out of and/or into the pneumostoma during regular breathing of the patient. Alternatively, gas may be provided to the pneumostoma at a slight positive pressure from outside the chest of the patient and the rate of flow of gas into the lung through the pneumostoma may be measured. Alternatively, as discussed below, diagnostic gases may be introduced through the pneumostoma to assess the patency and functionality of the pneumostoma. The diagnostic gases may be used for imaging the lungs and/or measuring collateral ventilation and gas exchange. The physician may compare the results of the visual, functional and/or structural assessment with prior assessment results and standard assessment results to determine changes and or trends in the results (step 210).

Based upon the results of the visual, functional and/or structural assessment of the pneumostoma and any trends in such results, the physician may decide to treat the pneumostoma and/or surrounding tissues to maintain or enhance the pneumostoma (step 212). The physician will select from the available treatment modalities a treatment suitable to maintain and/or enhance the function of the pneumostoma in light of the assessment results. (see step 220 of FIG. 2B). One or more treatment modalities may be used.

Figure 2B:
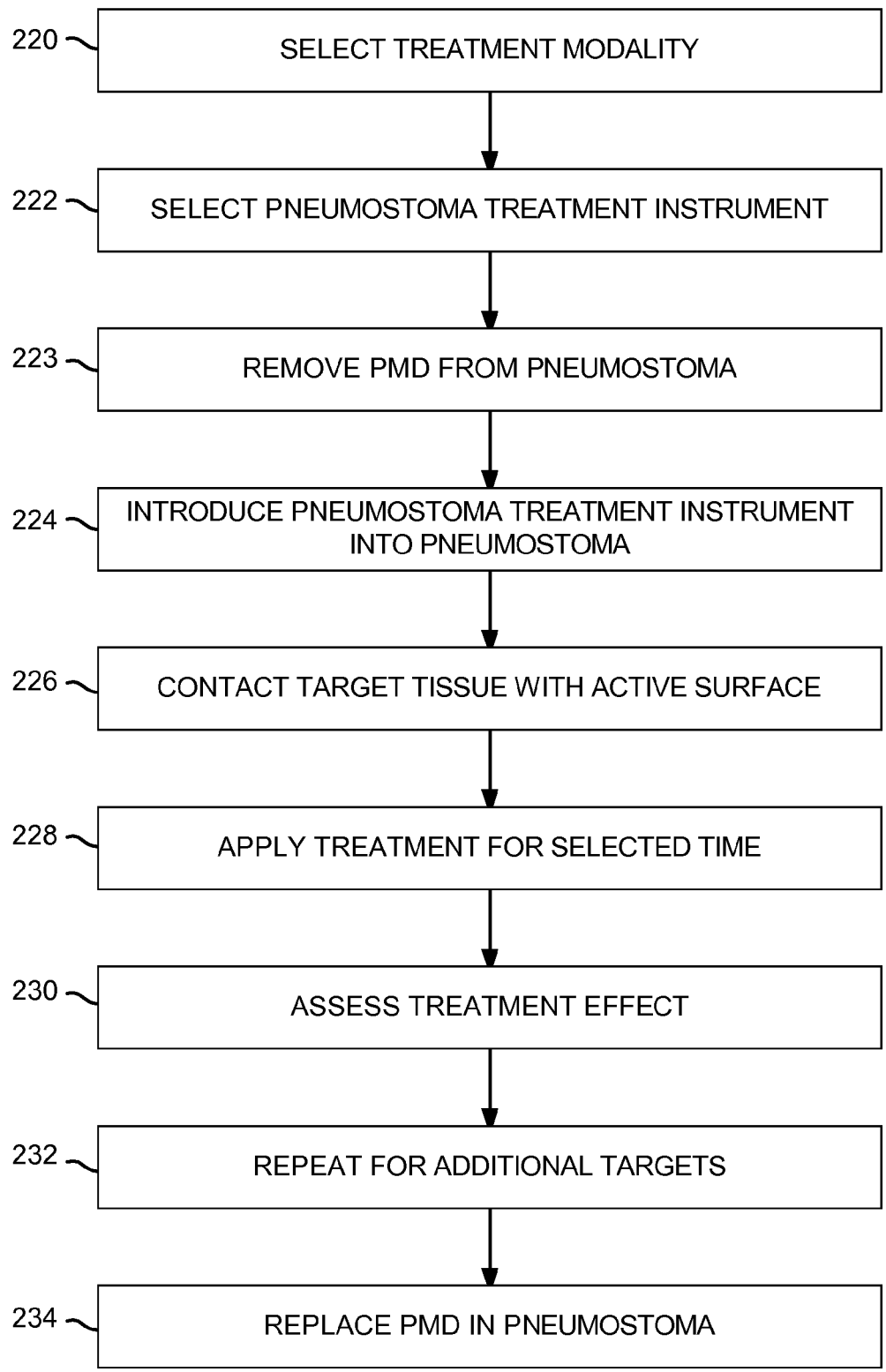
FIG. 2B is a flow chart illustrating general steps for follow-up care and treatment of a patient having a pneumostoma according to an embodiment of the invention.

FIG. 2B illustrates a general method for treatment of a pneumostoma. First, based on the assessment results, the physician selects a treatment modality to maintain or enhance the health and/or functionality of the pneumostoma (step 220). For example, suction may be used to aspirate discharge or other materials from the pneumostoma. Irrigation/lavage may be used to introduce a liquid into the pneumostoma in order to treat the tissue or aid in the removal of material from the pneumostoma. Irrigation/lavage may be used in conjunction with suction/aspiration to remove the liquid. Suction and/or irrigation may also be used in conjunction with a mechanical cleaning mechanism such as soft bristles, mechanical agitation, sonic/ultrasonic agitation or the like. The pneumostoma may be mechanically expanded using a balloon dilator, mechanical dilator or other tools. The pneumostoma may additionally be treated with heat, cold, light, electromagnetic radiation, electrocautery, sound/ultrasound, and the like.

The physician next selects a pneumostoma treatment instrument suitable to apply the treatment modality to the pneumostoma (step 222). The selected instrument is preferably sized such that it can be introduced into the pneumostoma and placed at a desired depth in the pneumostoma. As pneumostomas may vary in size, the instrument may have a configurable size, or may have a range of different adapters. Thus selection of the instrument will include selecting an instrument appropriate for the treatment modality and selecting/configuring the instrument for the pneumostoma of a particular patient.

The selected/configured instrument is introduced into the pneumostoma (step 224). In most cases, the pneumostoma management device will need to be removed (step 223) prior to inserting the treatment device. In some cases, the treatment modality requires contact of a target tissue with a treatment surface of the device (step 226). In other cases, the instrument treats the entire pneumostoma. The treatment is applied for a selected time (step 228). The effect of the treatment may then be assessed (step 230). In some cases the effect of the treatment is assessed with the pneumostoma treatment instrument. In other cases the pneumostoma treatment instrument may be removed and replaced with a pneumostoma inspection instrument to permit the assessment. The treatment may then be repeated if and as necessary for the pneumostoma or additional targets within the pneumostoma (step 232) until the desired effects have been achieved. After the treatment is over a new pneumostoma management device should be promptly and correctly positioned in the pneumostoma either by the physician, or by the patient under the observation of the physician (step 234). Particular instruments suitable for assessing and treating pneumostomas in accordance with the general method steps of FIGS. 2A and 2B are described below.

Pneumostoma Assessment Instruments and Methods

To observe the interior of the pneumostoma the physician uses a pneumostoma inspection instrument placed within the pneumostoma. One type of pneumostoma inspection instrument includes a light source for illuminating the interior of the pneumostoma and a visualization system for visualizing (and typically magnifying) the interior of the pneumostoma. The visualization system may be a direct optical system comprising one or more optical components for providing a magnified image at an object lens mounted to the instrument. Alternatively, the visualization system may include means for obtaining a video image of the pneumostoma tissues and means for displaying the image, for example a video sensor and a video display. Such a pneumostoma inspection instrument, using a light source and visualization system, is referred to generally herein as a pneumoscope.

A pneumoscope may include a short inspection tube or speculum that may be pushed into the pneumostoma. The speculum holds open the pneumostoma during the inspection. The speculum may in some cases be a detachable metal speculum which may be sterilized between uses. Preferably, however, the speculum is disposable or covered with a disposable sleeve during use. The speculum may be provided in a range of different diameters and lengths as appropriate for a particular pneumostoma or patient. The physician chooses the speculum appropriate to the dimensions of the pneumostoma of the patient. The speculum may be provided with visible exterior markings so that the physician may gauge the depth of insertion of the speculum. The speculum may be provided with a flange which prevents over-insertion of the speculum however the depth of insertion is typically under the control of the physician who should use care not to damage tissue of the pneumostoma during insertion. The physician may use the speculum to gauge the diameter, length and profile of the pneumostoma.

Figure 3A:
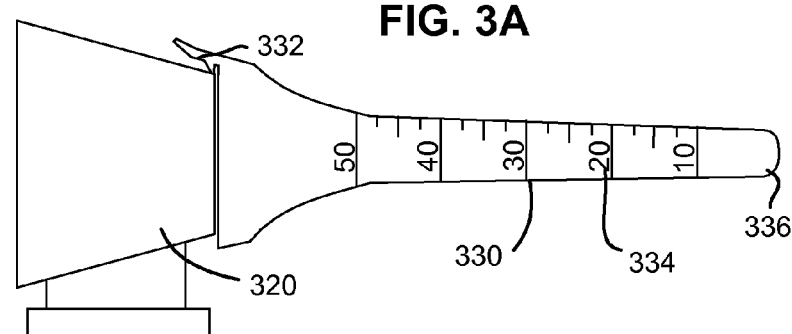
FIG. 3A shows an exterior view of an instrument for internal inspection of a pneumostoma according to an embodiment of the invention.
Figure 3B:
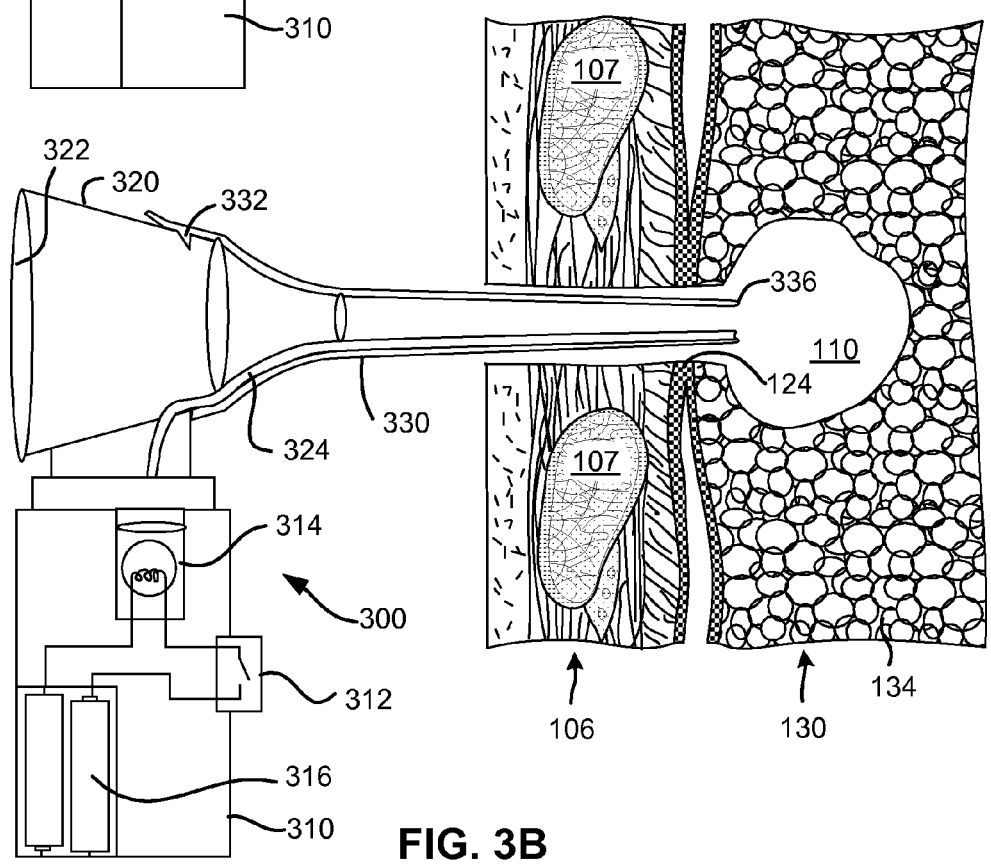
FIG. 3B shows a sectional view of the instrument for internal inspection of a pneumostoma of FIG. 3A positioned within a pneumostoma.

FIGS. 3A and 3B show an example of a pneumoscope according to one embodiment of the present invention. FIG. 3A shows an external view of a pneumoscope 300. FIG. 3B shows a sectional view of the pneumoscope positioned within a pneumostoma. As shown in FIG. 3A, pneumoscope 300 comprises a handle 310 and a head 320. A button 312 may be provided on handle 310 by which a physician may activate the light source and/or any image capturing system. A disposable speculum 330 is attached to head 320. Speculum 330 comprises a catch 332 at the proximal end for temporarily mounting speculum 330 to head 320 of pneumoscope 300. Speculum 330 is long enough to reach the end of a pneumostoma. As shown in FIG. 3A, speculum 330 bears external markings 334 indicating how far the distal tip 336 has travelled into the pneumostoma. External markings 334 may also be used to measure the depth of a pneumostoma. Pneumoscope 300 is preferably wireless and portable for ease of use.

As shown in FIG. 3B, handle 310 includes a light source 314 and power supply 316. In use, the distal tip 336 of speculum 330 is inserted into the pneumostoma 110. The physician actuates light source 314 to illuminate the interior of the pneumostoma 110. Light is directed from light source 314 to the pneumostoma 110 using an optical train 324 including e.g. fiber optics and/or lenses. The optical train 324 preferably provides uniform illumination of the field of view. In the embodiment of FIG. 3A, the head 320 comprises optics for viewing and magnifying the interior of the pneumostoma 110. The interior of the pneumostoma 110 may be observed by the physician through objective lens 322 within head 320. As shown in FIG. 3B, speculum 330 may be open at the distal tip 336. In alternative embodiments, distal tip 336 may be closed so long as a transparent window is provided through which the physician may observe the interior of the pneumostoma.

Figure 3C:
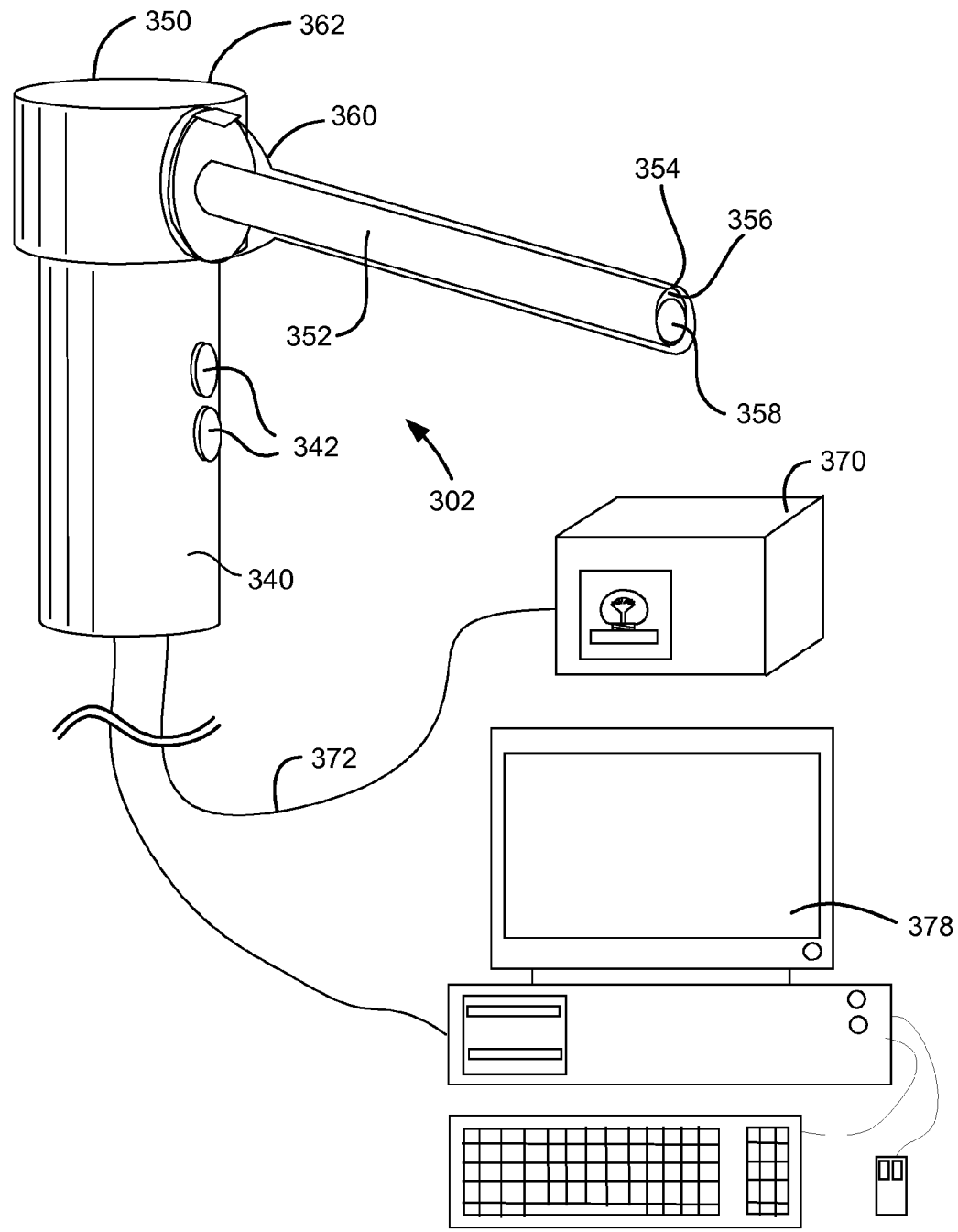
FIG. 3C shows an exterior view of an alternative instrument for internal inspection of a pneumostoma according to an embodiment of the invention.

FIG. 3C shows an alternative embodiment of a pneumoscope 302 comprising a handle 340 and a head 350. One or more buttons 342 may be provided on handle 340 by which a physician may activate the light source 370 and/or any image capturing system. A disposable cover 360 is attached to head 350. Cover 360 comprises a catch 362 at the proximal end for temporarily mounting cover 360 to head 350 of pneumoscope 302. Cover 360 protects an extension 352 of head 350. Extension 352 and cover 360 are long enough to reach the end of a pneumostoma. Cover 360 may be provided with external markings (not shown) indicating how far the distal tip 354 has travelled into a pneumostoma. Pneumoscope 302 is attached to a remote light source 370 and remote display system 378. Remote display system 378 may include an image capturing system to record video images of the pneumostoma.

Light source 370 provides light which is transmitted by a fiber optic cable 372 to the distal tip 354 of extension 352. A window 356 emits light to illuminate the field of view. A window 358 at the distal tip 354 admits light which is focused on an image sensor (not shown) which may be e.g. a CCD or CMOS sensor. The image sensor captures video image data which is transmitted to the display 378. The surgeon may observe video images of the interior of the pneumostoma on display 378 and/or may record images of the pneumostoma for later analysis. In alternative embodiments, one or both of the light source and display may be built into the head 350 and/or handle 340. Pneumoscope 302 may be inserted into a pneumostoma in the same manner as described with respect to pneumoscope 300 and illustrated in FIG. 3B.

Figure 3D:
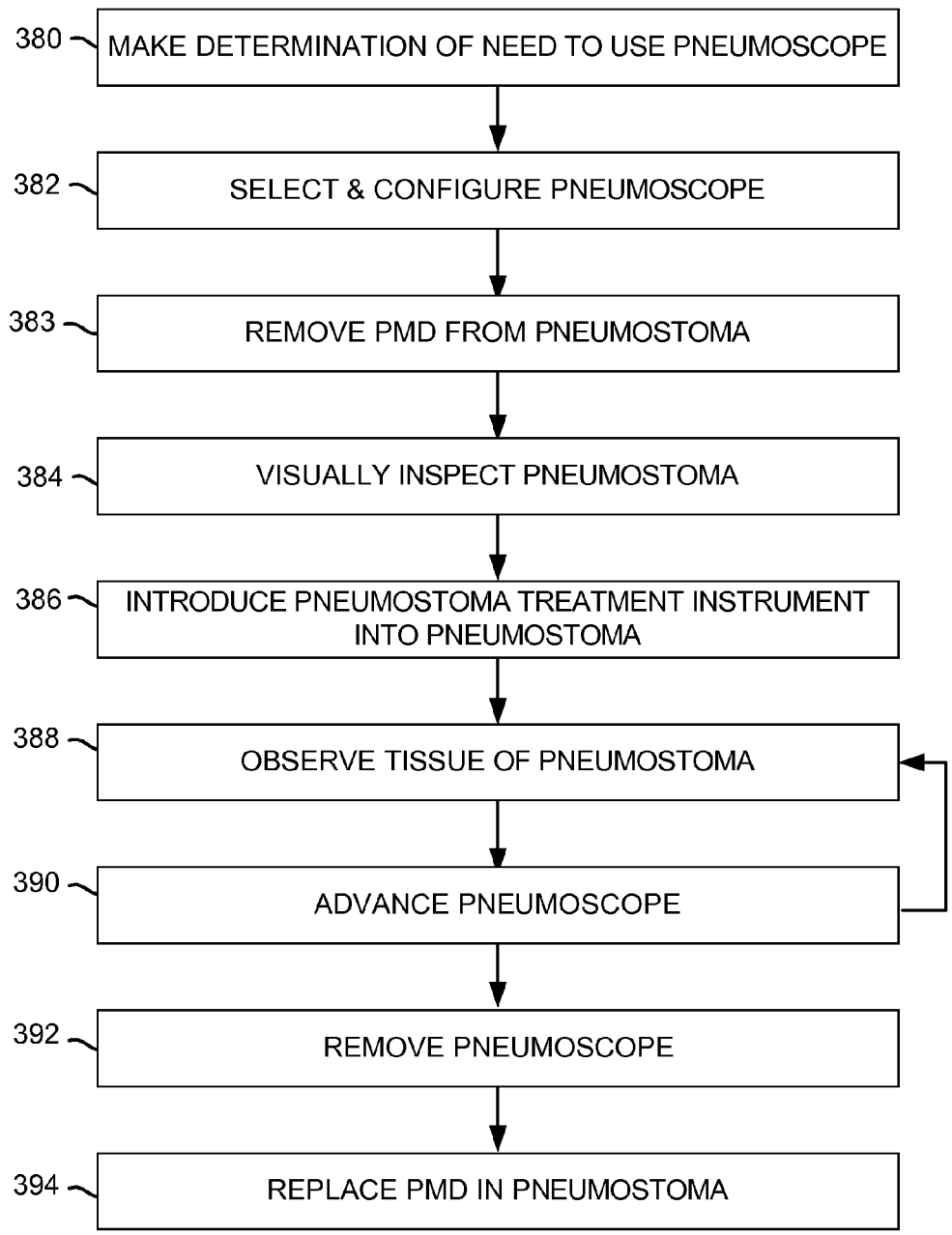
FIG. 3D is a flow chart illustrating steps for examination of a pneumostoma with a pneumoscope according to an embodiment of the invention.

FIG. 3D illustrates a general method for examining a pneumostoma with a pneumoscope. First, based on, for example, information from the patient or observation of the pneumostoma, the physician makes a determination to observe the pneumostoma using a pneumoscope (step 380). The physician next selects and/or configures a pneumoscope suitable to observe the pneumostoma of a particular patient (step 382). The selected instrument is preferably sized such that it can be introduced into the pneumostoma and placed at a desired depth in the pneumostoma. As pneumostomas may vary in size, the pneumoscope may have a configurable size, or may have a range of different sized speculums 330 and/or covers 360. Thus selection of the pneumoscope includes selecting/configuring the pneumoscope for the pneumostoma of a particular patient.

After the pneumoscope is ready, the pneumostoma management device will be removed from the pneumostoma (step 383). The pneumostoma should then be externally inspected (step 384) to determine whether there are any contraindications to use of a pneumoscope, for example any obstruction of the pneumostoma which must first be removed. If the external inspection reveals no contraindications, the pneumoscope is introduced into the pneumostoma (step 386). The physician should observe tissue of the pneumostoma through the visualization system of the pneumoscope (388) and note and/or record the appearance of the tissue. The physician then advances the pneumoscope into the pneumostoma (step 390) and repeats the observation (step 388) until reaching the end of the pneumostoma. When the inspection is completed the pneumoscope is removed (step 392). A PMD should be inserted into the pneumostoma promptly after removal of the pneumoscope either by the physician, or by the patient under the observation of the physician (step 394). In some cases, inspection with the pneumoscope is made in conjunction with treatment of the pneumostoma. In such a case, the pneumoscope may be used before, after and or during the treatment to observe effects of the treatment upon the tissue of the pneumostoma.

The pneumoscope allows the physician to visually inspect and examine the tissues of the pneumostoma. The physician may observe the pneumostoma and examine the tissue in the region of the chest wall, pleurodesis, and/or within the parenchymal tissue of the lung. In the event that inflamed, injured or unusual tissues are observed, it may be desirable to further assess the tissue. Further assessment of the tissue may be made, for example, by swabbing the tissue and culturing any microorganisms on the swab. Alternatively, a biopsy of tissue of the pneumostoma may be made by scraping tissue from the walls of the pneumostoma and examining cells under the microscope. In some embodiments, the pneumoscope may be provided with an auxiliary lumen through which a tool may be introduced into the pneumostoma in order to scrape or swab tissue under visualization.

Pneumostoma Assessment using Gas

Measurement of gases entering or leaving the pneumostoma may be useful for assessing the functionality of the pneumostoma. The ability of gas to pass through the pneumostoma may be measured in a number of ways. First, gas flow through the pneumostoma can be measured passively by placing a device over the pneumostoma which measures airflow out of and/or into the pneumostoma during regular breathing of the patient. Essentially, gases exiting the pneumostoma are collected by a system which records the volume of gas.

Additionally, the gas may be analyzed to determine composition of the gases exiting the pneumostoma. In particular it may be useful to analyze the proportion of oxygen, carbon dioxide and carbon monoxide in the gases exiting the pneumostoma as compared to in air exhaled through the natural airways or in the ambient atmosphere. Levels of carbon dioxide in gases exiting the pneumostoma are a useful indicator that the pneumostoma is still functioning to allow gases to exit the lung. It may also be useful to measure the presence of nitric oxide in the gases exiting the pneumostoma because nitric oxide may be indicative of inflammation of the tissues of the lung.

Gases exiting the pneumostoma may be measured and/or analyzed with a pneumostoma management device in place. However it is preferable to avoid any confounding effects due to the PMD, for example obstruction of the pneumostoma by the PMD, the filter of the PMD or accumulated discharge in the PMD. Therefore gas measurement/analysis is preferably performed using a gas analysis device inserted into the pneumostoma which is designed to collect gases and interface with the gas measurement/analysis equipment. See, e.g. FIGS. 4D and 4E. Gas analysis and measurement may be performed in a number of modes depending upon the results desired. Different systems may be used for analysis of pneumostoma function, lung function or lung imaging as required.

Systems for supplying gases, to a patient and analyzing gases received from a patient are already in use for supplying gases to be inhaled through the natural airways and analyzing gases exhaled through the natural airways. For example a system for analyzing expiratory gases is described in U.S. Pat. No. 6,506,608 titled "Method And Apparatus For Respiratory Gas Analysis Employing Enhanced Measurement Of Expired Gas Mass" to Mault. A system for supplying and analyzing diagnostic gases is described in U.S. Pat. No. 5,022,406 title "Module For Determining Diffusing Capacity Of The Lungs For Carbon Monoxide And Method" to Tomlinson et al. A review of DLCO spirometry can be found in Macintyre et al., "Standardisation Of The Single-Breath Determination Of Carbon Monoxide Uptake In The Lung," Eur. Respir. J. 26 (4): 720-35 (2005) and reference cited therein. A system for supplying and imaging hyperpolarized noble gases in the lungs is described in U.S. Patent Publication 2005/0174114 title "Method And System For Rapid Magnetic Resonance Imaging Of Gases With Reduced Diffusion-Induced Signal Loss" to Mugler III et al. A review of diffusion imaging of the lung can be found in Mayo et al., "Hyperpolarized Helium 3 Diffusion Imaging Of The Lung," Radiology 222:8-11 (2202) and reference cited therein. The above articles, patents and applications are incorporated herein by reference. These and other such systems may be adapted as described herein to supply and analyze gases utilizing the pneumostoma and thereby provide information regarding lung function, pneumostoma function and collateral ventilation not previously available.

Figure 4A:
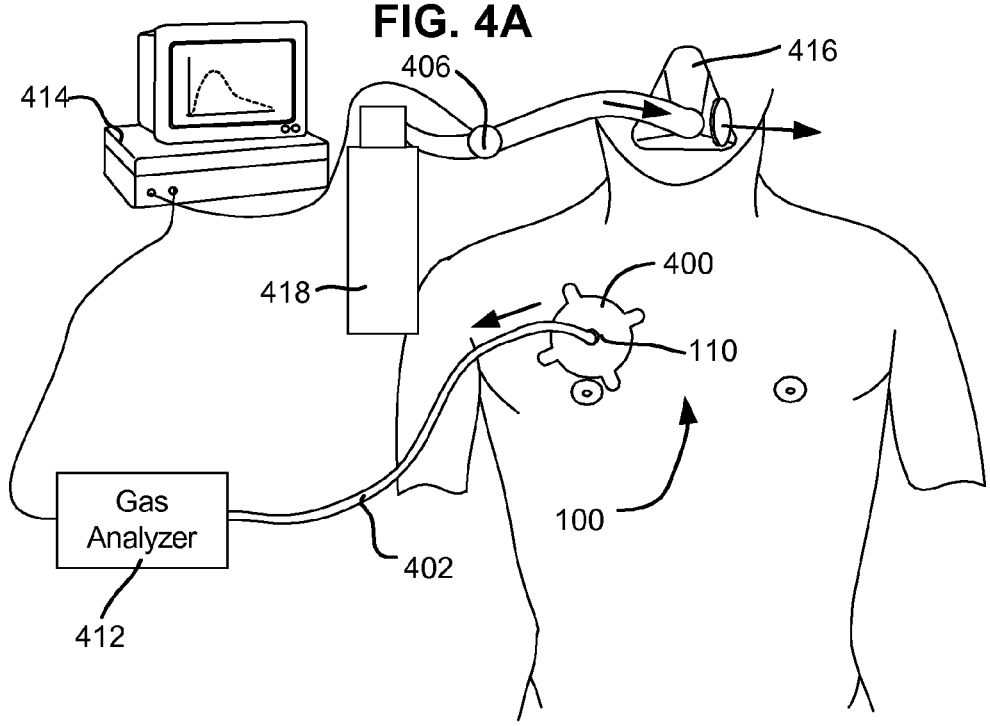
FIG. 4A shows a view of a spirometry system for assessing the functionality of a pneumostoma according to an embodiment of the present invention.

FIG. 4A shows a system for measuring/analyzing gases leaving the pneumostoma. Gas analysis equipment may be connected to a PMD and/or pneumostoma using one of the several techniques and mechanisms described herein. As shown in FIG. 4A, a gas analysis device 400 is inserted into the pneumostoma 110 of a patient. Gas analysis device 400 is connected by tube 402 to gas analyzer 412. The gases exhaled from the pneumostoma 110 may then be measured and/or analyzed during normal breathing or during an exercise test. The volume of gas exhaled may be measured by gas analyzer 412 to provide information regarding the patency/functionality of the pneumostoma. Furthermore, the presence, absence and/or amount of certain gases in the gases leaving the pneumostoma (if any) may be used to help determine the patency and/or efficacy of the pneumostoma. For example, if little or no carbon dioxide is sensed in the gas of the pneumostoma it might be concluded that the pneumostoma is not patent i.e. that there is no open pathway for gases to leave the lung via the pneumostoma.

The exhaled gas may be also be analyzed by gas analyzer 412 to determine oxygen and carbon dioxide concentrations. In some cases, the concentrations are compared to oxygen and carbon dioxide concentrations in the gases exhaled through the natural airways or in the ambient atmosphere. Such evaluation may be useful in determining the effectiveness of a pneumostoma and the location and/or desirability of additional pneumostomas. The output of gas analyzer 412 may be provided to a computer system 414 to display the results of the gas analysis. Computer system 414 preferably records the results of the gas measurement and analysis and allows the physician to compare the results of the gas measurement/analysis with prior results for the same patient.

Optionally, a mask 416 may be provided. Mask 416 may be used to measure the volume of gas inhaled and exhaled by the patient through the natural airways. The volume of gas inhaled and exhaled through the natural airways may be compared to the volume of gas exiting the pneumostoma. Optionally, a diagnostic gas 418 is introduced through the natural airways and the expiration of gases from the pneumostoma is measured. Computer system 414 controls valve 406 to supply the diagnostic gas 418 to the mask 416. The diagnostic gas may, for example, be a gas mixture such as DLCO gas used in diffusion spirometry (which nominally consists of 10% helium, 3000 ppm carbon monoxide and the balance air). As shown in FIG. 4A, optional mask 416 may be used to provide a diagnostic gas mixture 418 via the natural airways. The concentration of gases exiting the pneumostoma 110 may be compared to the concentration of gases in the diagnostic gas supply 418. The time-course of exhalation of diagnostic gases through the pneumostoma may be analyzed by gas analyzer 412 to evaluate the function of the pneumostoma and the prevalence of collateral ventilation pathways connecting the pneumostoma to the remainder of the lung. Such evaluation may be useful in determining the effectiveness of a pneumostoma and the location and/or desirability of additional pneumostomas.

Alternatively, gases may be provided through the pneumostoma from outside the chest of the patient. Gas supply equipment may be connected to a PMD and/or pneumostoma using one of the several techniques and mechanisms described herein. The gas is preferably supplied at a controlled pressure slightly above the ambient air pressure so as not to cause injury to the pneumostoma. In a simple case, the rate of flow of gas into the lung through the pneumostoma may be measured. The rate of gas flow at a particular pressure may be used to assess the patency of the pneumostoma. Alternatively, diagnostic gases may be introduced through the pneumostoma for assessing collateral ventilation and gas exchange. Diagnostic gases may be helpful in measuring functional attributes of the pneumostoma and the lung. In particular, introduction of diagnostic gases through the pneumostoma may be useful for assessing gas diffusion between the pneumostoma and the lung.

In one example, a diagnostic gas is introduced through the pneumostoma and the gas is measured as it is exhaled through the natural airways. The diagnostic gas may, for example, be a gas mixture such as DLCO gas used in diffusion spirometry (which nominally consists of 10% helium, 3000 ppm carbon monoxide and the balance air). Gases exhaled through the natural airways are analyzed to determine gas concentrations. The time course of exhalation of the diagnostic gas is indicative of factors such as pneumostoma functionality and collateral ventilation. The time course of exhalation of gas through the natural airways compared to introduction into the pneumostoma may be analyzed to evaluate the function of the pneumostoma and the prevalence of collateral ventilation pathways connecting the pneumostoma to the remainder of the lung. Such evaluation may be useful in determining the effectiveness of a pneumostoma and the location and/or desirability of additional pneumostomas. A supply of the diagnostic gas may be connected to a PMD and/or pneumostoma using one of the several techniques and mechanisms described herein.

Figure 4B:
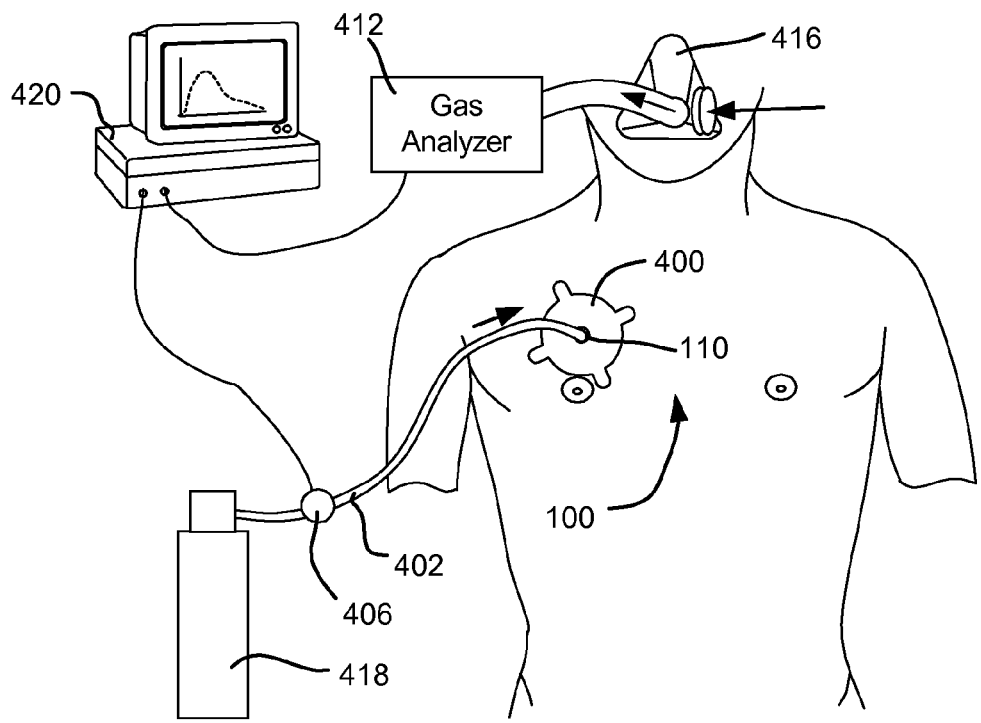
FIG. 4B shows a view of a gas analysis system for assessing the functionality of a pneumostoma according to an embodiment of the present invention.

FIG. 4B shows a schematic view of a lung assessment system using introduction of diagnostic gas 418 through a pneumostoma 110. As shown in FIG. 4B a gas analysis device 400 is inserted into the pneumostoma 110 of a patient. Gas analysis device 400 is connected by tube 402 to a pressure-regulated source of diagnostic gas 418. A solenoid-controlled valve 406 in tube 402 controls the flow of diagnostic gas into pneumostoma 110. The patient is provided with a mask 416 which allows the patient to inhale ambient air but that collects the exhaled air and passes it to gas analyzer 412. During exhalation, a portion of the exhaled gases is collected in a sample collection system and then analyzed using discrete gas sensors and/or a gas chromatograph. The gas analyzer 412 and the solenoid-controlled valve 406 are connected to a computer system 420 which may be a general purpose computer. Computer system 420 controls solenoid-controlled valve 406 and receives data from gas analyzer 412. Computer system 420 analyzes the gas concentrations in the gas exhaled by the patient and factors the relative values with inspired gas volume and other parameters to calculate factors related to collateral ventilation and pneumostoma function. The output of gas analyzer 412 may be provided to computer system 420 to display the results of the gas analysis. Computer system 420 preferably records the results of the gas measurement and analysis and allows the physician to compare the results of the gas measurement/analysis with prior results for the same patient.

Introduction of diagnostic gases through a pneumostoma may also be used to enhance imaging the lung with a CT scan or NMR scan. For example polarized Helium-3 may be utilized to enhance nuclear magnetic resonance/magnetic resonance imaging of the lung (analogous to the way contrast agents enhance X-ray imaging). For example, polarized helium-3 may be produced with lasers and the magnetized pressurized gas may be stored for several days. When introduced into the lung, the polarized helium-3 can be imaged with an MRI-like scanner which produces breath-by-breath images of lung ventilation, in real-time. Polarized helium-3 may thus, be used to visualize airways in static or dynamic fashion. Alternative gases which may be used as visualization agents include gaseous radionuclide xenon or technetium DTPA in an aerosol form.

Introducing a controlled amount of a visualizable gas, e.g. polarized Helium-3, through the pneumostoma and imaging the diffusion of the gas into the lung over time may be utilized for quantitative evaluation of the function of the pneumostoma and the prevalence of collateral ventilation pathways connecting the pneumostoma to the parenchymal tissue of the lung. Measuring the time-course variations in diffusion of Helium-3 into the lung allows analysis of diffusion coefficients for areas of the lung. Such evaluation may be useful in determining the effectiveness of a pneumostoma and the location and/or desirability of additional pneumostomas. A source of polarized Helium-3 may be connected to a PMD and/or pneumostoma using one of the several techniques and mechanisms described herein.

Figure 4C:
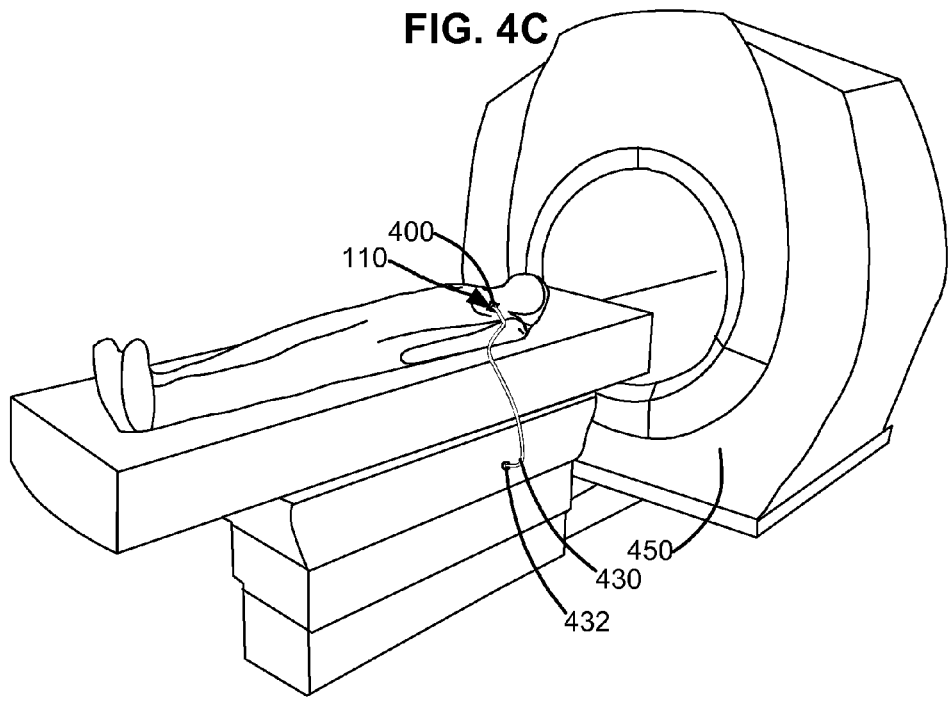
FIG. 4C shows a view of lung imaging system for imaging gas diffusion from a pneumostoma according to an embodiment of the present invention.

FIG. 4C shows a schematic view of a lung assessment system using a diagnostic gas in conjunction with an imaging scanner 450. Scanner 450 may be an MRI, NMR, CT or X-Ray so long as the particular diagnostic gas used may be successfully imaged with the system. As shown in FIG. 4B, gas analysis device 400 is inserted into the pneumostoma 110 of a patient. Gas analysis device 400 is connected by tube 430 to a pressure-regulated source of a visualizable gas (e.g. polarized Helium-3). A solenoid-controlled valve 432 in tube 430 controls the flow of diagnostic gas into pneumostoma 110. The scanner 450 and the solenoid-controlled valve 432 are connected to a computer system 420 (not shown) which may be a general purpose computer. The computer system 420 (not shown) controls solenoid-controlled valve 432 and receives data from scanner 450. The computer system 420 coordinates the introduction of diagnostic gas into the patient with the patient's breathing and also with the operations of scanner 450 in order to accurately image dispersion of the diagnostic gas from the pneumostoma 110 to other parts of the lung. Computer system 420 analyzes the time course distribution of the diagnostic gas from the pneumostoma into the lung tissues to calculate factors related to collateral ventilation and pneumostoma function, e.g. diffusion coefficients.

Figure 4D:
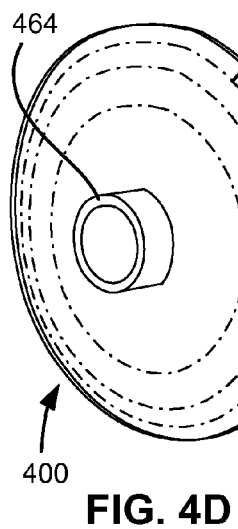
FIGS. 4D and 4E show views of a diagnostic device for delivering diagnostic gas to a pneumostoma or sampling gas from a pneumostoma according to embodiments of the present invention.
Figure 4E:
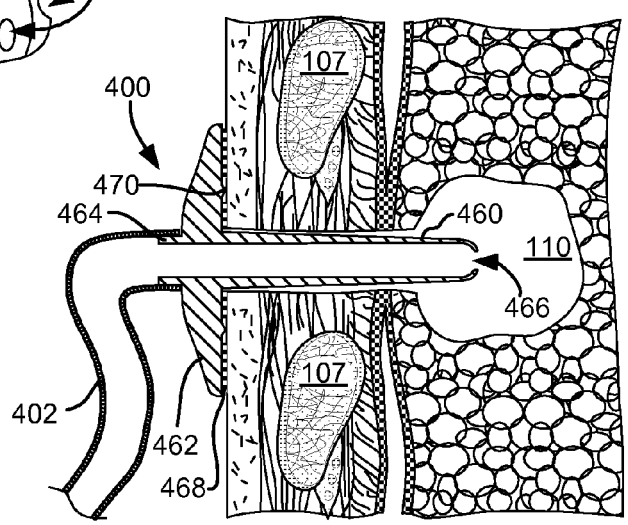

FIGS. 4D and 4E show views of the gas analysis device 400 of FIGS. 4A-4C. FIG. 4D shows a perspective view of the gas analysis device 400 while FIG. 4E shows a sectional view of gas analysis device 400 positioned within a pneumostoma. In general terms, gas analysis device 400 is a device which can be secured into a pneumostoma for sampling gases exiting the pneumostoma and/or providing gases into the pneumostoma. Gas analysis device 400 can form part of a system which utilizes such gas sampling or gas provision for assessment of pneumostoma function and/or lung function. As used in FIGS. 4A and 4C, gas analysis device 400 is used to introduce diagnostic gas into the pneumostoma. As used in FIG. 4B, gas analysis device 400 is used to collect gases exhaled from the lung for analysis by gas analyzer 412.

Referring to FIG. 4D, gas analysis device 400 includes a hollow tube 460 for insertion into the pneumostoma. Hollow tube 460 is surrounded by a flange 462 which secures tube 460 in position in the pneumostoma. Hollow tube 460 connects to a coupling 464 on the proximal side of flange 462. Coupling 464 is configured so that tube 402 (shown in FIG. 4E) may be readily connected and disconnected. Hollow tube 460 has one or more holes 466 at the distal end through which gas may pass into or out of a pneumostoma. Hollow tube 460 and flange 462 also provide a temporary seal which inhibits leakage of gas from around hollow tube 460.

FIG. 4E shows a sectional view of gas analysis device 400 of FIGS. 4A-4D in position in a pneumostoma 110. It is preferable to minimize leakage of gases into or out of the pneumostoma. Flange 462 is thus provided with an adhesive coating 468 on the distal surface to provide a temporary seal between the gas analysis device 400 and the skin of the chest of the patient. Surface features may also be provided on the distal surface of flange 462 or on tube 460 to promote sealing between gas analysis device 400 and the pneumostoma. For example, a circular ridge 470 is shown in section on FIG. 4E. Gas analysis device 400 is preferably a disposable component that will be used only with one patient. One or more filters may be interposed between gas analysis device 400 and the gas supply and/or gas analyzer to prevent possible cross-contamination between patients.

FIG. 4F shows a perspective view of a home gas analysis (e.g. capnography) unit for use by a patient to analyze gases in the pneumostoma. Portable gas analyzer 470 comprises a battery powered analyzer unit 472 connected to a tube 474 adapted to be place in a pneumostoma. Gas analyzer unit 472 can include a single gas sensor or multiple gas sensors sensitive to different gases. Suitable gas sensors are commercially available, for example, the miniature optical (NDIR) carbon dioxide sensor available from Europa Environmental Ltd. (Gloucestershire, United Kingdom). Tube 474 may be disposable or reusable. Tube 474 has one or more apertures 474 in the distal end for allowing entry of gases from the pneumostoma. An optional vent 476 is provided 474 is provided on the front surface of the gas analyzer 472 to allow escape of gases. However, where low concentrations of gas are measured it is better to close the vent and allow the concentration of gas to equilibrate with the concentration in the pneumostoma. Gas analyzer unit 472 has controls 478 for mode selection and a display 480 for indicating test duration and gas analysis results. The gas analysis results can be used to determine patency of the pneumostoma, (for example by measuring carbon dioxide) and inflammation (for example by measuring nitric oxide and/or carbon monoxide).

The patient may use the home gas analyzer periodically or as directed by the physician to facilitate assessment and treatment of the pneumostoma. In use, the patient and/or caregiver removes a pneumostoma management device from the pneumostoma and inserts tube 474 of portable gas analyzer 470. The patient/caregiver operates controls 478 to select and begin a gas analysis. The timer counts down sufficient time for gas equilibrium and measurement. The gas analysis results and/or patient instructions are then presented on display on display 480. The gas analyzer provides sufficiently accurate results for the physician to determine when the patient needs to visit the physician for a more through assessment and/or treatment of the pneumostoma. So as not to causes unnecessary visits to the physician, the results provided by the gas analyzer may be limited. For example, the result display might simply be "OK" unless and or until the gas analysis indicates that further diagnosis and/or treatment of the pneumostoma is required—in which cases the analysis reads—"Check With Physician". Gas analyzer 470 includes a memory unit 482 (for example a memory card) which records gas analysis data measured for a patient. The gas analysis data is downloaded and examined by the physician during a patient visit to facilitate diagnosis and treatment.

Pneumostoma Treatment

Based upon the assessment of the pneumostoma, it may be necessary or desirable to treat the pneumostoma in order to preserve and/or enhance the health and/or functionality of the pneumostoma. A principal purpose of the pneumostoma is to permit the escape of gases trapped in the lung thereby reducing the lung volume and ameliorating symptoms of COPD such as dyspnea and anoxia. To serve this purpose gases should be able to enter the pneumostoma from the parenchymal tissue of the lung. High rates of air flow are not required. However, if the pneumostoma becomes completely obstructed then it will no longer permit the escape of gases trapped in the lung. The function of the pneumostoma may be impaired by, among other causes, the encroachment of tissues into the pneumostoma, obstruction with secretions, discharge and/or foreign objects, inflammation and/or infection. For example, encroaching tissues may impair the patency and functionality of the pneumostoma.

The pneumostoma and surrounding tissues may be treated using a number of different treatment modalities to maintain and/or enhance patency, remove obstructions, decrease inflammation and prevent infection. The treatment modalities include: suction, irrigation, lavage, mechanical agitation, ultrasound, infrasound, mechanical dilation, balloon dilatation, cryotherapy, and energy treatment (including e.g. UV, light, LASER, LED, IR, heat, RF and electrocautery). The physician may select from among the several treatment modalities a treatment modality most appropriate for the conditions observed during the pneumostoma assessment.

Pneumostoma Treatment using Suction, Irrigation and Lavage

The treatment modalities available for treating a pneumostoma include suction, irrigation, mechanical agitation and lavage. These treatment modalities are suitable for removing obstructions and discharge from the pneumostoma, cleaning the pneumostoma and treating the tissues of the pneumostoma. Additional methods and devices for applying suction to a pneumostoma are disclosed in applicant's U.S. Provisional Patent Application 61/084,559 titled "Aspirator For Pneumostoma Management" which is incorporated herein by reference. An aspirator may be used without irrigation for the removal of liquid/soft discharge and materials from the pneumostoma.

FIGS. 5A-5C illustrate a device for treating a pneumostoma with suction, irrigation, mechanical irritation and/or lavage. As shown in FIG. 5A, a suction-irrigation device 500 includes a body 510 attached to a suction-irrigation probe 520. Suction-irrigation probe 520 includes a multi-lumen tube 522 and a flange 524. As shown in the sectional view FIG. 5B of suction-irrigation probe 520, multi-lumen tube 522 has an outer lumen 521 and an inner lumen 523. Referring again to FIG. 5A, multi-lumen tube 522 has a number of side apertures 526 for releasing fluid from the outer lumen 521. Multi-lumen tube 522 has a distal aperture 528 in the distal tip for applying suction and removing fluid via the inner lumen 523. Distal aperture 528 may be provided with a cage or mesh covering to prevent damage to tissues and/or obstruction of distal aperture 528. Multi-lumen tube 522 also supports a plurality of soft bristles 530 for mechanically agitating the surface of a pneumostoma. Although bristles are shown, other mechanical features may be used to assist the removal of material which may be adhered to the tissue of the pneumostoma, for example ribs, fingers or surface roughness.

Referring now to FIG. 5C, suction irrigation probe 520 is connected to a body 510 by a coupling 532 which mounts releasably to a mating coupling 512 on body 510. Body 510 is also connected to a pressure-regulated supply of irrigation fluid and a pressure-regulated vacuum supply (not shown). The irrigation supply and vacuum supply are attached or connected to an irrigation conduit 514 and suction conduit 516 within body 510. The couplings 532 and 512 releasably mount the suction-irrigation probe 520 to body 510. The couplings 532 and 512 also put the lumens of multi-lumen tube 522 in fluid communication with the irrigation conduit 514 and suction conduit 516 within body 510. The releasable couplings 532 and 512 also enable the suction-irrigation probe 520 to be removed, and either cleaned and replaced, or disposed of and replaced. Couplings 532, 512 may be, for example, threaded couplings, bayonet couplings, luer locks or other connector suitable for releasable connecting lumens.

FIG. 5C shows a sectional view of suction-irrigation device 500 with suction-irrigation probe 520 inserted into a pneumostoma 110. As shown in FIG. 5C, irrigation fluid exits through side apertures 526 and is collected through distal aperture 528. Bristles 530 contact the tissue of the pneumostoma 110. Suction-irrigation probe 520 may be moved in and out of pneumostoma 110 so that bristles 530 dislodge any material stuck on the side of pneumostoma 110. The irrigation fluid serves to move any dislodged materials into aperture 528. Flange 524 serves to prevent over-insertion of suction-irrigation probe 520 and also to prevent excessive leakage of irrigation fluid from the pneumostoma. In some embodiments, flange 524 may be configured to slide up and down multi-lumen tube 522 such that the depth of the distal end of probe 520 may be adjusted while the flange remains in contact with the chest of the patient. In other embodiments, flange 524 may be fixed or adjustably fixed to multi-lumen tube 522.

Suction-irrigation device 500 may include additional features to facilitate removal of material from the pneumostoma. For example, suction-irrigation device 500 may include a visualization system to permit the physician to guide suction-irrigation probe 520 and visualize the tissues inside pneumostoma 110. See, e.g. FIGS. 3A-3C and accompanying text. Suction-irrigation device 500 may also include an ultrasound generator or another device to agitate bristles 530 and the irrigation fluid to aid in the mechanical removal of materials from the pneumostoma 110. Suction irrigation device 500 may also include a trap for trapping any solid materials dislodged from the pneumostoma. For irrigation, a sterile but inert solution may be used. For example, sterile saline or sterile water may be used. The irrigation fluid will typically be sterile water or saline solution. In some cases, it may be desirable to use a medicated irrigation fluid. For example, an antibacterial or mucolytic solution may be used. In such cases a small concentration of the therapeutic agent is added to the sterile water or saline. Suitable therapeutic agents include anti-inflammatories, antibiotics and anti-stenosis compounds. The irrigation fluid may also include a small concentration of an agent for maintaining the patency of the pneumostoma, for example, Paclitaxel. The cleaning solution should be formulated carefully to avoid injury or irritation to the lung.

Figure 5D:
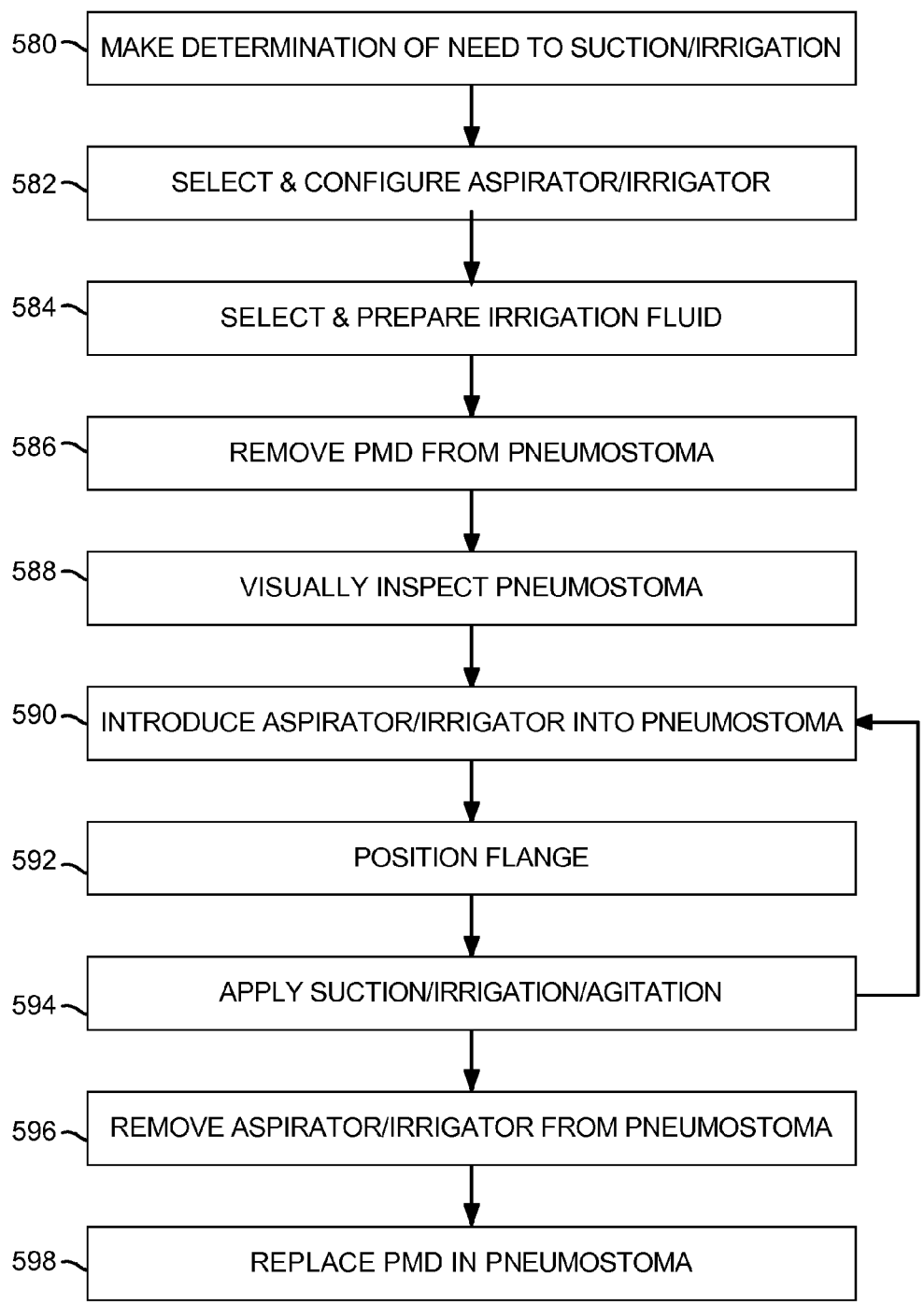
FIG. 5D is a flow chart illustrating steps for treatment of a pneumostoma with suction, irrigation and/or lavage according to an embodiment of the invention.

FIG. 5D illustrates a method for treatment of a pneumostoma. First, based on, for example, information from the patient or observation of the pneumostoma, the physician makes a determination to treat the pneumostoma with one or more of suction, irrigation and/or lavage. (step 580). The physician next selects and/or configures an aspirator/irrigator suitable to treat the pneumostoma of a particular patient. (step 582). The selected instrument is preferably sized such that it can be introduced into the pneumostoma and placed at a desired depth in the pneumostoma. As pneumostomas may vary in size, the aspirator/irrigator may have a configurable size, or may have a range of different sized probes 520. Thus selection of the aspirator/irrigator includes selecting/configuring the aspirator/irrigator for the pneumostoma of a particular patient. If irrigation/lavage is to be performed, the physician should also select and/or prepare the irrigation fluid (step 584).

After the aspirator/irrigator and optional irrigation fluid is ready, the pneumostoma management device will be removed from the pneumostoma (step 586). The pneumostoma should then be externally inspected (step 588) to determine whether there are any contraindications to use of the aspirator/irrigator, for example any obstruction of the pneumostoma which must first be removed. If the visual inspection reveals no contraindications, the aspirator/irrigator is introduced into the pneumostoma (step 590). The physician may then position the flange so as to prevent excess leakage from the pneumostoma (step 592). The physician will the apply suction to remove materials from the pneumostoma (step 594). While suction is applied the physician may also provide irrigation/lavage and or agitation to dislodge materials for removal (step 594.) The physician may advance the aspirator/irrigator incrementally further into the pneumostoma and repeats the treatment (step 594) until reaching the end of the pneumostoma. When the treatment is completed the aspirator/irrigator is removed (step 596). A PMD should be inserted into the pneumostoma promptly after removal of the aspirator/irrigator either by the physician, or by the patient under the observation of the physician (step 598). In some cases, treatment with the aspirator/irrigator is made in conjunction with inspection of the pneumostoma with a pneumoscope. In such case, the pneumoscope may be used before and after treatment to observe effects of the treatment upon the tissue of the pneumostoma and to ensure all deleterious materials have been removed from the pneumostoma.

Pneumostoma Treatment using Sound

The treatment modalities available for treating a pneumostoma include the use of sound waves. Sound waves can be used to agitate the walls of the pneumostoma to dislodge materials. Sound waves of different frequencies may be of use, including infrasound below 20 Hz, acoustic sound waves between 20 Hz and 20 KHz and ultrasound above 20 KHz. These treatment modalities are suitable for removing obstructions and discharge from the pneumostoma, cleaning the pneumostoma and treating the tissues of the pneumostoma to enhance and/or maintain patency of the pneumostoma. The amplitude, frequency and duration of sound waves supplied may be selected to achieve the desired effects. In some cases the amplitude, frequency and duration of the sound waves may be sufficient to kill cells, inhibit proliferation of cells or disrupt cells and connective tissue in order to enhance or maintain the patency of the pneumostoma. In other cases, the sound waves may be selected to dislodge materials e.g. discharge, which may be adhered to the tissues of the pneumostoma. In some embodiments, ultrasound may be used in conjunction with suction/irrigation to remove materials from the pneumostoma.

Figure 6A:
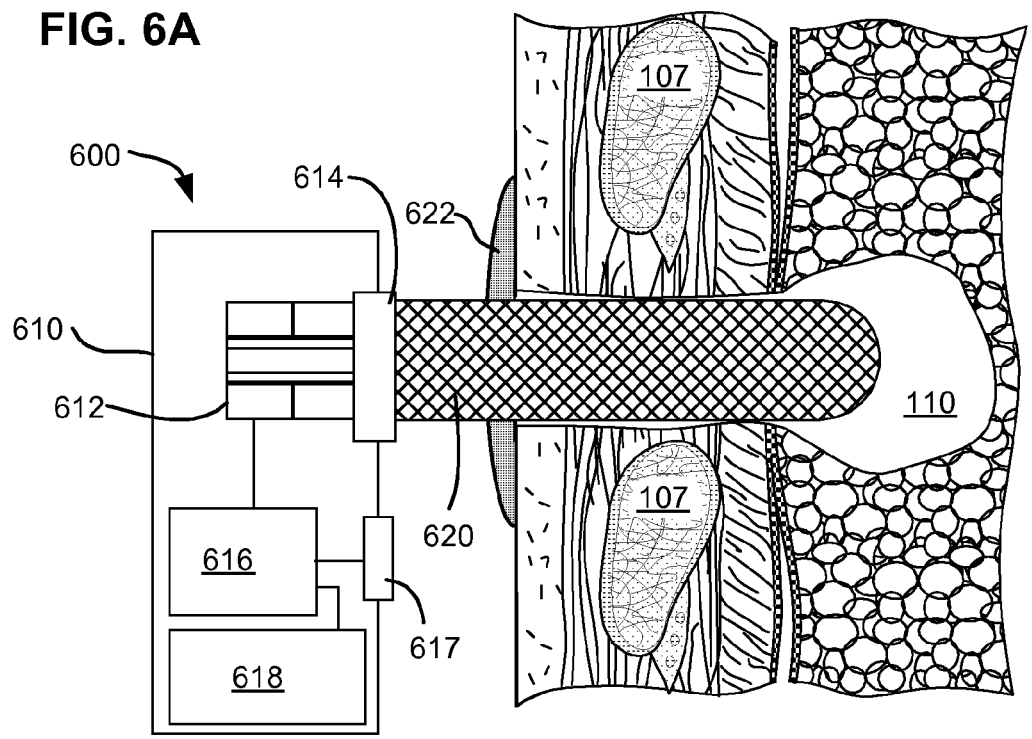
FIG. 6A shows a view of an ultrasound device for cleaning or treating the pneumostoma according to an embodiment of the invention.

FIG. 6A shows a sectional view of an ultrasound device 600 for use in a pneumostoma 110. Ultrasound device 600 includes a body 610 containing an ultrasonic transducer 612 coupled by a coupling 614 to an ultrasound probe 620. Ultrasonic transducer 612 is coupled to ultrasound probe 620 so that, when energized, ultrasonic transducer 612 transmits ultrasound into ultrasound probe 620. Ultrasound device 600 includes within body 610, a switch 617, a controller 616 and power supply 618. The physician operates switch 617 to cause controller 616 to energize ultrasonic transducer 612. In preferred embodiments, controller 616 energizes ultrasonic transducer 612 for a predefined and limited period of time.

Ultrasound probe 620 is sized and configured to enter pneumostoma 110 and conduct ultrasound energy from ultrasonic transducer 612 to the walls of the pneumostoma and any materials adhered thereto. Ultrasound probe 620 may also include a flange 622 which serves as protection against over insertion of probe 620. A biocompatible gel or liquid (not shown) may be used with ultrasound probe 620 to enhance the conduction of ultrasonic waves from ultrasound probe 620 to tissues of the pneumostoma. In such case, flange 622 may also be useful to create a temporary seal to retain the gel or liquid with pneumostoma 110 during the ultrasound treatment. In some embodiments, ultrasound probe 620 may be provided with a channel to provide suction to remove any materials dislodged by the ultrasound. Alternatively, a separate suction/irrigation device may be utilized to remove materials from the pneumostoma after treatment with the ultrasound probe 620.

Figure 6B:
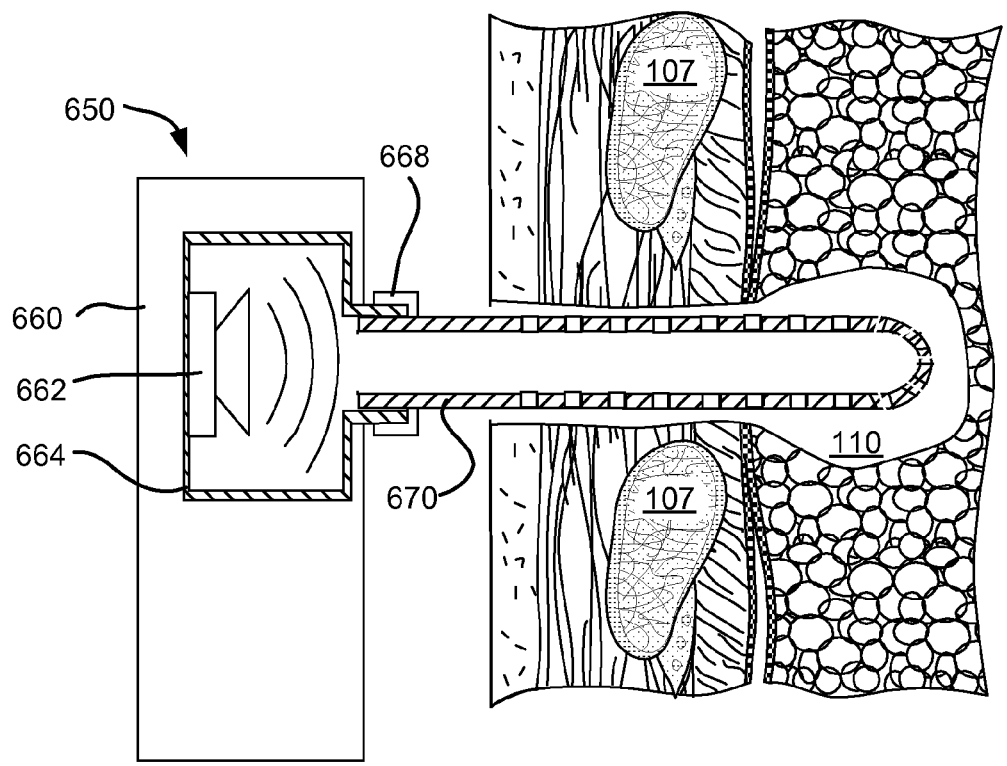
FIG. 6B shows a view of a sound-wave therapy device for cleaning or treating the pneumostoma according to an embodiment of the invention.

FIG. 6B shows a schematic view of alternate sound delivery device 650 for use in a pneumostoma 110. Sound delivery device 650 includes a body 660 containing a speaker 662 which typically comprises a magnetically-driven armature or diaphragm. Speaker 662 generates acoustic and/or infrasound waves in chamber 664. Chamber 664 is in communication via coupling 668 with sound probe 670. As shown in FIG. 6B, sound probe 670 is a hollow tube for holding open the pneumostoma and delivering the sound waves into the pneumostoma. Sound probe 670 may have one or more apertures. A baffle may be provided around sound probe 670 to concentrate pressure waves induced by the speaker with the pneumostoma. Alternatively, sound probe 670 may be a solid probe coupled to the armature of speaker 662 or a suitable transducer. In alternative embodiments, the sound may be generated by a speaker located within the probe which is thus located within the pneumostoma during use. The energy delivered by sound delivery device 650 serves to dislodge materials from the pneumostoma and/or disrupt the connective tissue of the pneumostoma. In some embodiments, sound probe 670 may be provided with a channel to provide suction to remove any materials dislodged by the sound waves. Alternatively, a separate suction/irrigation device may be utilized to remove materials from the pneumostoma after treatment with the sound delivery device 650.

FIG. 6C illustrates a method for treatment of a pneumostoma. First, based on, for example, information from the patient or observation of the pneumostoma, the physician makes a determination to treat the pneumostoma with one or more of acoustic sound, infrasound, and/or ultrasound. (step 680). The physician next selects and/or configures a sound/ultrasound device suitable to treat the pneumostoma of a particular patient. (step 682). The selected instrument is preferably sized such that it can be introduced into the pneumostoma and placed at a desired depth in the pneumostoma. As pneumostomas may vary in size, the sound/ultrasound device may have a configurable size, or may have a range of different sized probes 620 or 670. Thus selection of the sound/ultrasound device includes selecting/configuring the sound/ultrasound device for the pneumostoma of a particular patient. If a sound conducting liquid or gel is to be used, the physician should also select and/or prepare the fluid (step 684).

After the sound/ultrasound device and optional sound-conducting fluid is ready, the pneumostoma management device will be removed from the pneumostoma (step 686). The pneumostoma should then be externally inspected (step 688) to determine whether there are any contraindications to use of the sound/ultrasound device, for example any obstruction of the pneumostoma which must first be removed. If the visual inspection reveals no contraindications, the sound/ultrasound device is introduced into the pneumostoma (step 690). The physician may then position the flange so as to prevent excess leakage from the pneumostoma (step 692). The physician will then energize the sound/ultrasound probe for a selected period of time (step 694). The physician may advance the sound/ultrasound device incrementally further into the pneumostoma and repeat the treatment (step 694) until reaching the end of the pneumostoma. When the treatment is completed the sound/ultrasound device is removed (step 696). A PMD should be inserted into the pneumostoma promptly after removal of the aspirator/irrigator either by the physician, or by the patient under the observation of the physician (step 698).

In some cases, treatment with the sound/ultrasound device is made in conjunction with inspection of the pneumostoma with a pneumoscope. In such case, the pneumoscope may be used before and after treatment to observe effects of the treatment upon the tissue of the pneumostoma and to ensure all deleterious materials have been removed from the pneumostoma. It may also be desirable to clean the pneumostoma with suction/irrigation prior to reinsertion of the PMD in order to remove any materials that may have been dislodged during the treatment.

Pneumostoma Treatment using Mechanical Dilatation

The treatment modalities available for treating a pneumostoma include the use of mechanical dilatation. Overtime, the natural healing response of the body may cause tissues to encroach into the lumen of the pneumostoma. Additionally, the tissues bordering the pneumostoma may thicken over time reducing the permeability of the pneumostoma walls to gases. A dilator may be used to stretch the tissues of the pneumostoma to maintain the patency of the pneumostoma. Dilatation not only increases the size of the lumen of the pneumostoma but also thins the tissues surrounding the pneumostoma. This thinning of the tissues bordering the pneumostoma in the lung may enhance the ability of air to enter the pneumostoma from the parenchymal tissue of the lung thereby enhancing the functionality of the pneumostoma. In embodiments, a dilator comprises an expander which can be inserted into the pneumostoma at a first contracted size and then expanded to a desired expanded size thereby stretching the pneumostoma. In preferred embodiments the dilator comprises an indicator outside the body which indicates the extent to which the expander has been expanded and/or an adjustable limiter which limits expansion of the expander to a safe amount.

Figures 7A, 7B:
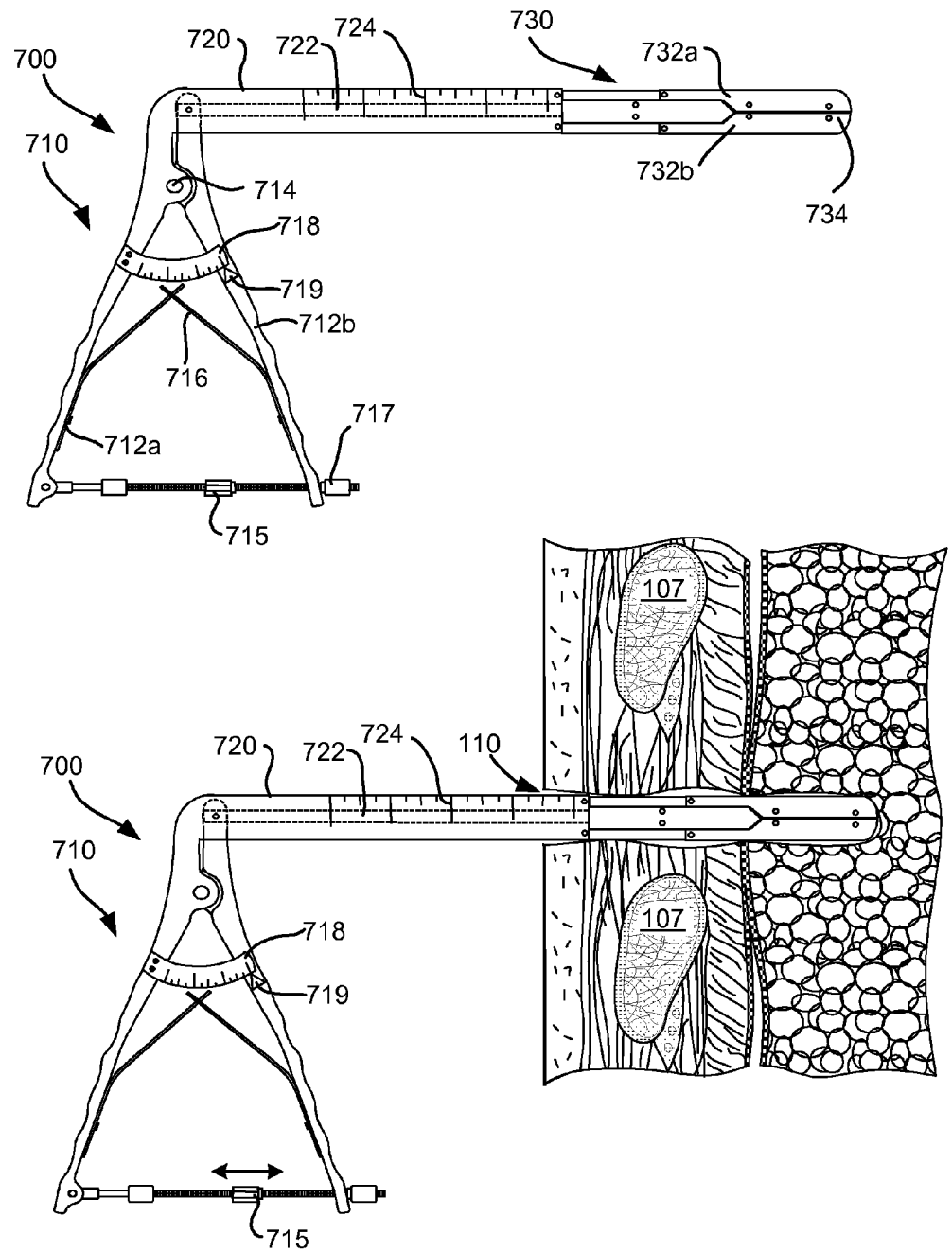

FIGS. 7A-7D show views of one embodiment of mechanical dilator 700. As shown in FIG. 7A, mechanical dilator 700 comprises a handle 710, a shaft 720 and an expander 730. Handle 710 includes two arms 712*a*, 712*b* connected by a pivot 714. A spring mechanism 716 biases arms 712*a*, 712*b* apart. A screw mechanism 717 may be used to lock arms 712*a*, 712*b* closer together at any desired position. A limit mechanism 715 may be used to limit the approach of arm 712*a* towards arm 712*b* in order to prevent over expansion of the expander 730. Handle 710 is connected to shaft 720. Arm 712*a*, is fixedly connected to the exterior of shaft 720, arm 712*b* is pivotally connected to inner shaft 722. Moving arm 712*b* towards arm 712*a* moves inner shaft 722 more distally relative to shaft 720. Handle 710 also includes a gauge 718 marked to indicate the amount of expansion of expander 730. Gauge 718 is fixed to arm 712*a*. An indicator 719 fixed to arm 712*b* moves along gauge 718 as the arms are moved towards each other thereby expanding expander 730. The markings on gauge 718 correspond to the expansion of expander 730.

Shaft 720 is sized so as to fit into the pneumostoma. Shaft 720 may be provided with markings 724 on the exterior surface so the physician may determine the depth to which the distal tip of expander 730 has been inserted in the pneumostoma. Expander 730 includes two blades 732*a*, 732*b*. Blades 732*a*, 732*b* are semicircular in section so that, in the collapsed configuration, blades 732*a*, 732*b* form a cylinder of the same external diameter as shaft 720. Blades 732*a*, 732*b* also form a rounded distal tip 734 in their collapsed configuration to facilitate insertion of expander 730 into the pneumostoma.

FIG. 7B shows mechanical dilator inserted into a pneumostoma 110 (shown in section). As shown in FIG. 7B, the mechanical dilator 700 is inserted into the pneumostoma 110 in the collapsed configuration of FIG. 7A until it is located at the desired depth in the pneumostoma as indicated by the markings 724. In some situations, mechanical dilator 700 may be used to measure the diameter of a pneumostoma. The expander may be inserted into the pneumostoma and the handles compressed until resistance is felt. The indicator 719 will indicate on gauge 718 the degree of expansion of expander 730 at this point of first resistance and thus indicate the internal diameter of the pneumostoma. Limit mechanism 715 may then be positioned to allow only a desired amount of incremental expansion of the pneumostoma compared to the measured initial diameter of the pneumostoma. In alternative embodiments, a fixed or adjustable flange (not shown) may be provided mounted on shaft 720. The flange serves as mechanical stop to limit insertion of the mechanical dilator 700 at a fixed or adjustable depth.

FIG. 7C shows a close-up view of the expander 730 in an expanded configuration. As shown in FIG. 7C, each of blades 732*a* and 732*b* are pivotably connected by linkages 736*a*, 736*b* to the distal end of shaft 720. Each of blades 732*a*, 732*b* is also pivotably connected to the distal end of inner shaft 722 by linkages 738*a*, 738*b*, 738*c*, 738*d*. Linkages 738*a*, 738*b*, 738*c*, 738*d* are designed to fit within a slot in the interior surface of blades 732*a*, 732*b* when the blades are in the collapsed configuration of FIG. 7A. In alternative embodiments, expander 730 may have 3 or more blades, each blade taking up a fractional portion of the circumference of the device and each blade having three linkages connecting the blade to the distal end of inner shaft 722. As inner shaft 722 moves in the direction of arrow 704, blades 732*a*, 732*b* move outwards as shown by arrows 702*a*, 702*b*.

FIG. 7D shows mechanical dilator 700 positioned in a pneumostoma 110. As shown in FIG. 7D, expander 730 is positioned within the pneumostoma at the desired depth. Handle 712*b* has been pushed towards handle 712*a* until it makes contact with limit mechanism 715. Handle 712*b* may optionally be locked into position with screw mechanism 717. Inner shaft 722 has been pushed distally relative to shaft 720. Linkages 738*a*, 738, b, 738*c*, 738*d* have thus forced blades 732*a*, 732*b* away from each other causing the expander 730 to adopt the expanded position shown in FIG. 7C (see FIGS. 7B and 7C for identification of the components of expander 730). Note that indicator 719 has moved along gauge 718 to indicate the amount of expansion of expander 730.

In practice, mechanical dilator 700 is preferably expanded a small amount and then locked in place as the tissues of the pneumostoma relax. Mechanical dilator 700 is then expanded another small amount and then locked in place again as the tissues of the pneumostoma relax. A number of incremental expansion steps may be performed until the desired diameter of the pneumostoma is achieved. The incremental steps can be controlled by incremental movement of limit mechanism 715 and screw mechanism 717. In some cases, it may be desirable to expand the dilator at two or more different depths in the pneumostoma so as to expand two or more different potions of the pneumostoma. Dilator 700 may then be collapsed and withdrawn from the pneumostoma. The pneumostoma will tend to contract after dilatation so it is important to insert a pneumostoma management device into the lumen of the pneumostoma upon removal of the mechanical dilator 700.

Figure 7E:
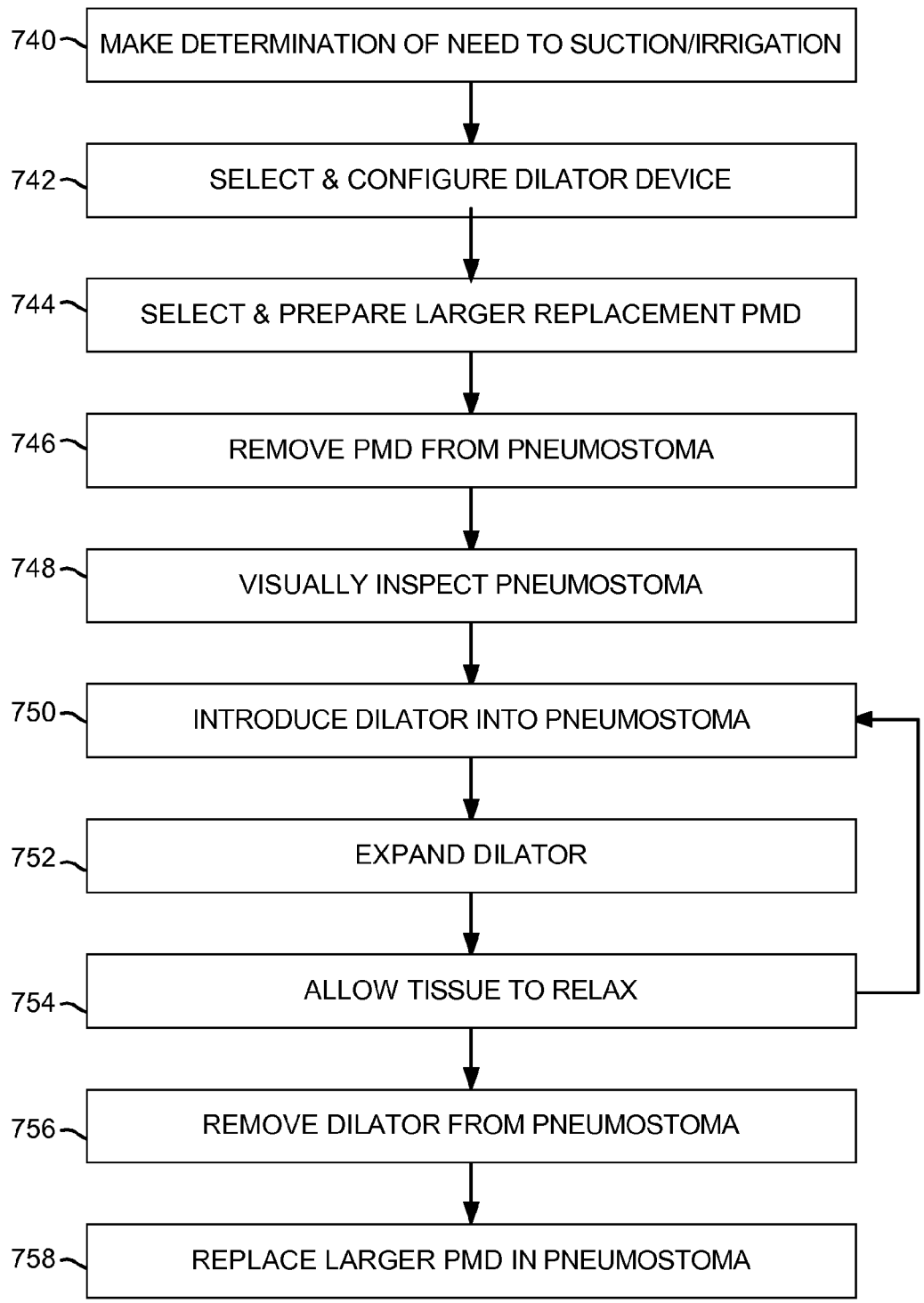
FIG. 7E is a flow chart illustrating steps for treatment of a pneumostoma with a mechanical instrument for dilating the pneumostoma according to an embodiment of the invention.

FIG. 7E illustrates a method for treatment of a pneumostoma with a dilator. First, based on, for example, information from the patient or observation of the pneumostoma, the physician makes a determination to treat the pneumostoma with a dilator. (step 740). The physician next selects and/or configures a dilator suitable to treat the pneumostoma of a particular patient. (step 742). The selected instrument is preferably sized such that it can be introduced into the pneumostoma and placed at a desired depth in the pneumostoma. As pneumostomas may vary in size, the dilator may have a configurable size, or a range of initial sizes. Thus selection of the dilator includes selecting/configuring the dilator for the pneumostoma of a particular patient such that it may be inserted into the pneumostoma to the desired depth prior to dilation. After dilation of the pneumostoma it is preferable to insert a PMD to support the pneumostoma as soon as the dilator is removed. Therefore, it is preferable to select and prepare a larger PMD for the patient to fit the anticipated dilated pneumostoma (step 744).

After the dilator and replacement PMD are, the original (smaller) pneumostoma management device will be removed from the pneumostoma (step 746). The pneumostoma should then be externally inspected (step 748) to determine whether there are any contraindications to use of the dilator, for example any obstruction of the pneumostoma which must first be removed. If the visual inspection reveals no contraindications, the dilator is introduced into the pneumostoma (step 750). The physician may then expand the dilator incrementally (step 752). The physician will then allow the tissue of the pneumostoma to relax (step 754) and repeat the incremental expansion (step 752) until the desired dilation has been achieved. The physician may also repeat the dilation at one or more depths within the pneumostoma depending upon the length of the pneumostoma. When the dilation is complete the dilator is removed (step 756). A new larger PMD should then be promptly inserted into the pneumostoma by the physician, or by the patient under the observation of the physician (step 758).

In some cases, treatment with the sound/ultrasound device is made in conjunction with inspection of the pneumostoma with a pneumoscope. In such case, the pneumoscope may be used before and after treatment to observe effects of the treatment upon the tissue of the pneumostoma and to ensure all deleterious materials have been removed from the pneumostoma. It may also be desirable to clean the pneumostoma with suction/irrigation prior to reinsertion of the PMD in order to remove any materials that may have been dislodged during the treatment.

Figure 7F:
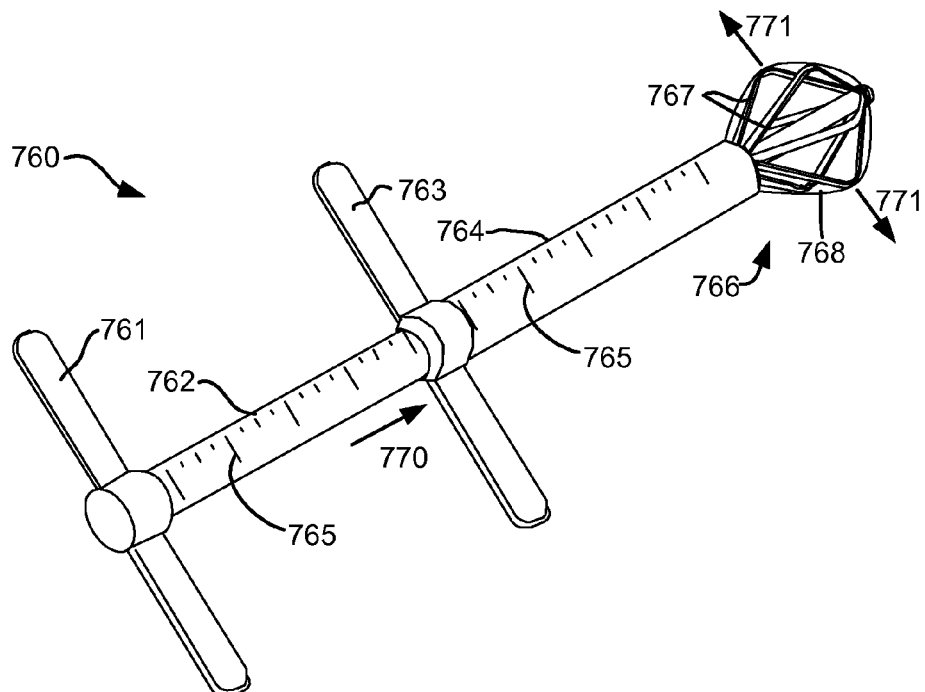
FIG. 7F shows an alternative mechanical instrument for dilating the pneumostoma or a portion of the pneumostoma according to an embodiment of the present invention.
Figure 7G:
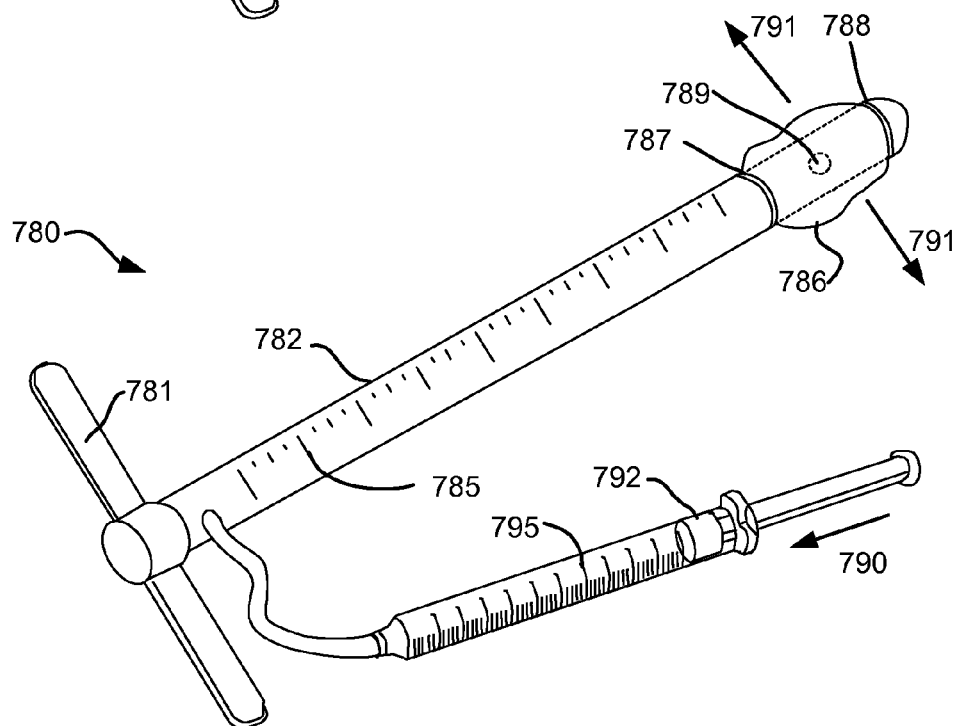
FIG. 7G shows an alternative mechanical instrument for dilating the pneumostoma or a portion of the pneumostoma according to an embodiment of the present invention.

Alternative means may be used to dilate the pneumostoma in alternative embodiments. FIG. 7F shows an alternative mechanical dilator 760 and FIG. 7G shows a balloon dilator 780. Referring to FIG. 7F, mechanical dilator 760 comprises first handle 761 connected to inner shaft 762 which extends to the distal tip of the mechanical dilator 760. A second handle 763 is connected to an outer shaft 764 which rides on inner shaft 762. At the distal end of mechanical dilator 760 is expander 766. Expander 766 includes a plurality of flexible elements 767 covered by a polymer shell 768. The distal end of each flexible element 767 and polymer shell 768 is connected to the distal end of inner shaft 762. The proximal end of each flexible element 767 and polymer shell 768 is connected to the distal end of outer shaft 764. When outer shaft 764 is pushed distally along inner shaft 762 (as shown by arrow 770), flexible elements 767 bend or bow outwards (as shown by arrows 771). Elements 767 push on polymer shell 768 causing it to also bow outwards (in the direction of arrows 771). Thus mechanical dilator 760 transitions from the collapsed configuration to the expanded configuration by pushing handle 763 distally relative to handle 761. Both outer shaft 764 and inner shaft 762 have markings 765 on the exterior surface so the physician may assess the depth of insertion of mechanical dilator 760 and the diameter of expansion of mechanical dilator 760. Mechanical dilator 760 may be used in the same way as dilator 700 of FIGS. 7A-7D, either for dilating the pneumostoma or assessing the diameter of the pneumostoma. Mechanical dilator 760 may additionally be provided with a locking device to hold it in an expanded position and/or a limit device to control expansion of the expander 766.

FIG. 7G shows a balloon dilator 780. Referring to FIG. 7F, mechanical dilator 780 comprises first handle 781 connected to a hollow shaft 782 which extends to the distal tip of the balloon dilator 780. At the distal end of mechanical dilator 780 is balloon 786. Balloon 786 is sealed to the hollow shaft at the proximal end 787 and distal end 788 of balloon 786. An aperture in hollow shaft 782 communicates between the lumen of the hollow shaft 782 and the interior of balloon 786. A syringe 792 is connected to the proximal end of hollow shaft 782. When syringe 792 is compressed (as shown by arrow 790), a liquid such as sterile saline is pushed through hollow shaft 782 into balloon 786 causing balloon 786 to inflate (as shown by arrows 791). Thus balloon dilator 780 transitions from the collapsed configuration to the expanded configuration by compressing syringe 792. Hollow shaft 782 has markings 785 on the exterior surface so the physician may assess the depth of insertion of balloon dilator 780. Syringe 792 has exterior markings 795 so that the physician may assess the volume of balloon 786 and hence the diameter to which it has been expanded. Balloon dilator 780 may be used in the same way as dilator 700 of FIGS. 7A-7D, either for dilating the pneumostoma or assessing the diameter of the pneumostoma.

Balloon 786 may be formed of a relatively inelastic material. In such case, injection of the liquid into the balloon will expand the balloon to a preset size. This ensures that the balloon does not stretch the pneumostoma more than desired. Moreover, the balloon can be expanded at high pressure without risk of over-expansion. However, a number of different balloon dilators may be required having different sizes in order to treat different pneumostomas or to incrementally expand a single pneumostoma. In alternative embodiments, a relatively elastic material may be used to make balloon 786. In such case, the balloon will have a larger diameter for larger amounts of liquid allowing broader application. However, the pressure applied by the balloon to the tissue will be lower than for an inelastic balloon.

Pneumostoma Treatment using Localized Thermotherapy

The treatment modalities available for treating a pneumostoma include the application of heat (thermotherapy) or cold (cryotherapy). Thermotherapy and cryotherapy can be used to affect physical characteristics of tissues and cell proliferation and also to treat infection. For example, the tissues of the pneumostoma tend to encroach into the lumen of the pneumostoma thereby impairing the function of the pneumostoma. One way to reduce tissue encroachment is through the use of thermotherapy or cryotherapy thereby maintaining or enhancing the patency of the pneumostoma. In some embodiments a pneumostoma treatment device may be used to heat the tissue in others the pneumostoma treatment device may be used to cool the tissue to achieve the desired effects.

In one method of thermotherapy, a surface of a pneumostoma treatment device is brought into contact with a target tissue of the pneumostoma. The surface of the pneumostoma treatment device is then heated to raise the temperature of the target tissue (e.g. by electrical heating, laser heating, or by circulating a heated medium). Other methods of thermotherapy include application of focused ultrasound, infrared light, radio or microwave-frequency radiation to the target tissue to induce the desired temperature rise in the target tissue. For example, thermotherapy treatment device may direct energy at the tissue to heat the target tissue. The energy may be supplied as ultrasound, electrical energy, electromagnetic energy (for example IR or laser energy). The treatment is applied for a selected period of time. After the treatment the tissue is reassessed and treated again as necessary. The treatment may be applied to the pneumostoma tissue using a range of treatment devices and modalities as described in more detail below. In preferred embodiments, the temperature and duration of the heat treatment are selected to affect physical characteristics of tissues, reduce cell proliferation and/or treat infection but not to kill tissues of the pneumostoma.

Methods of cryotherapy include placing the target tissues in thermal contact with a cooled device or medium to lower the temperature of the target tissue. Cryotherapy may be used in two modes. The first mode of cryotherapy is cryogenic ablation in which cryotherapy is used to freeze tissue. A device is used to lower the temperature of the target cells to temperatures below freezing for short periods of time. The cells in the frozen tissue die and the tissue is removed. However, it is a disadvantage of tissue ablation that the cell necrosis stimulates the healing response. The healing response causes cell proliferation and generation of more cells in the form of scar tissue. As a result, cryogenic ablation may ultimately lead to greater tissue encroachment rather than less tissue encroachment. Cryogenic ablation may however still be useful for treating regions where tissue is encroaching into the pneumostoma.

A second mode of cryotherapy is cryogenic cooling in which cells are cooled below physiologic temperatures without freezing the cells. A device is used to lower the temperature of the target cells to temperatures between normal physiologic temperatures and a temperature above freezing for short periods of time. Cryogenic cooling has been found to reduce hyperplasia in blood vessels. See e.g. U.S. Pat. No. 6,811,550 entitled "Safety Cryotherapy Catheter" to Holland et al. Cryogenic cooling may also be used to his mode of cryotherapy to treat larger areas of the pneumostoma including up to the entire pneumostoma. In preferred embodiments, the temperature and duration of the cryotherapy are selected to affect physical characteristics of tissues, reduce cell proliferation and/or treat infection but not to kill tissues of the pneumostoma.

Figure 8A:
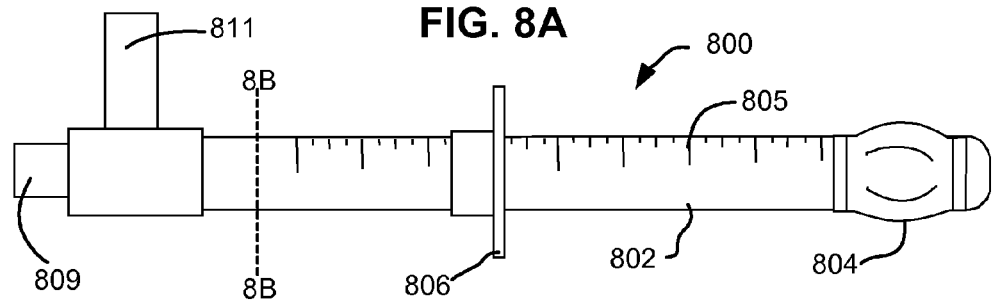
FIGS. 8A-8C show views of a thermotherapy device for treating tissues of a pneumostoma according to an embodiment of the present invention.
Figure 8B:
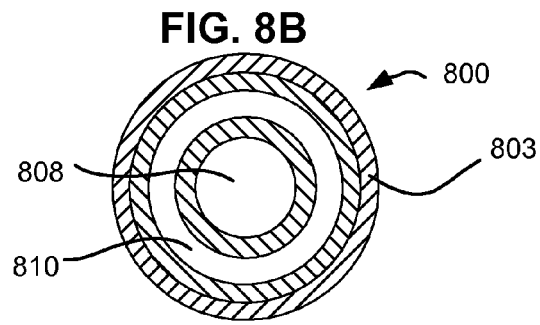
Figure 8C:
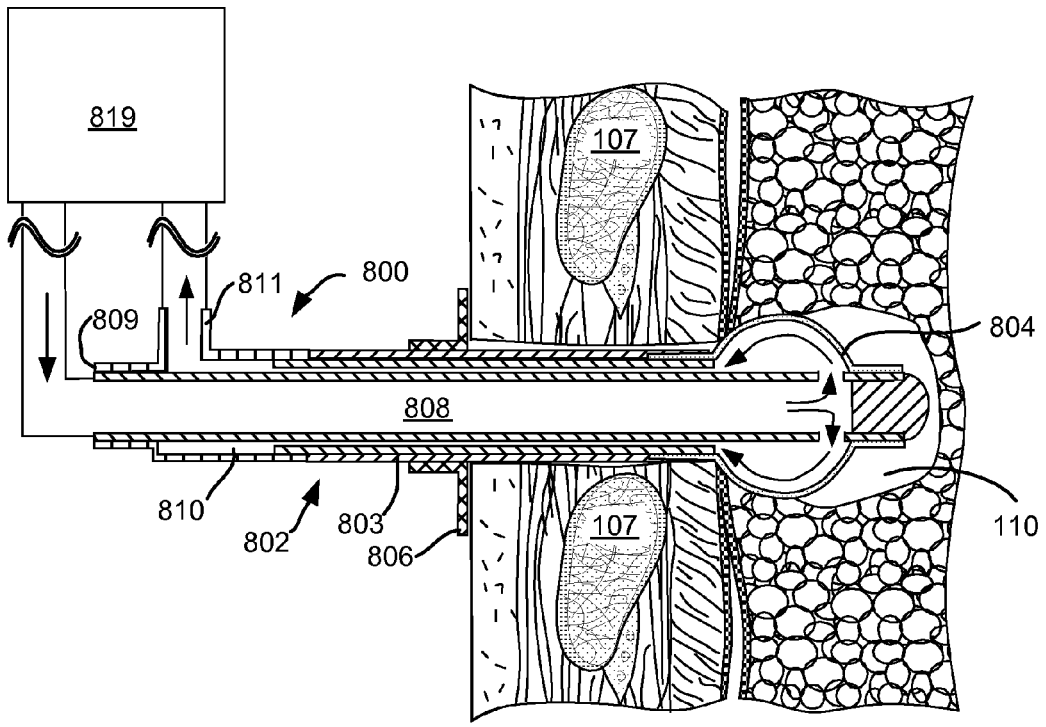

FIGS. 8A-8C show a catheter which may be used for cryotherapy or thermotherapy of a pneumostoma tissues. As shown in FIG. 8A, catheter 800 includes a shaft 802, a balloon 804 and a flange 806. Flange 806 slides on the exterior of shaft 802 and acts as a mechanical stop for insertion of shaft 802 into a pneumostoma. The positioning of flange 806 on shaft 802 allows the physician to control the depth of balloon 804 and thus the location of the treatment area. The shaft 802 is provided with external markings 805 to indicate the distance between the treatment area and flange 806 thereby facilitating application of the treatment to the desired target tissues.

As shown in FIG. 8B, shaft 802 has two lumens in inner lumen 808 and outer lumen 810. In some embodiments shaft 802 may be coated with an insulating layer 803 so that treatment is limited to the region of the balloon 804. The balloon may then be moved to different locations in the pneumostoma to treat different areas. In other embodiments, shaft 802 is not insulated and is also designed to treat the tissues of the pneumostoma in addition to the balloon. In such cases, it is preferable that treatment is performed at a single position (because to do otherwise would treat areas along the shaft 802 multiple times). As shown in FIG. 8C, at the proximal end of shaft 802 are an inlet 809 which communicates with inner lumen 808 and an outlet 811 which communicates with outer lumen 810.

As used for cryotherapy, catheter 800 is introduced in to the pneumostoma 110 to a depth limited by flange 806 as shown in FIG. 8C. Cryotherapy catheter 800 is connected to a cryotherapy coolant system 819 which supplies a temperature-controlled coolant fluid to cryotherapy catheter 800. A coolant fluid is introduced through inlet 809 into inner lumen 808. The coolant passes through inner lumen 808 to the distal end of cryogenic catheter 800. The coolant passes through an aperture out of inner lumen 808 into the balloon 804. The coolant inflates balloon 804 to bring it into contact with the tissue of the pneumostoma 110. The coolant circulates around balloon 804 and cools the surface of balloon 804 to the desired temperature. The coolant then returns through the outer lumen 810 and exits the catheter via the outlet 811. In some embodiments, a temperature sensor may be included in the distal tip of cryotherapy catheter 800 in order to monitor the temperature of the balloon. However, in other embodiments, temperature regulation is performed by regulating the temperature of the coolant supplied by the cryotherapy coolant system.

The coolant fluid is preferably a non-toxic liquid such as saline. However, liquids other than saline may be used and in some cases the coolant fluid may be a temperature-controlled gas. One system for supplying coolant is described in U.S. Pat. No. 6,432,102 entitled "Cryosurgical Fluid Supply" to Joye et al. If thermotherapy of the tissues is desired, a fluid heated to above body-temperature may be used in place of the coolant.

Figure 8D:
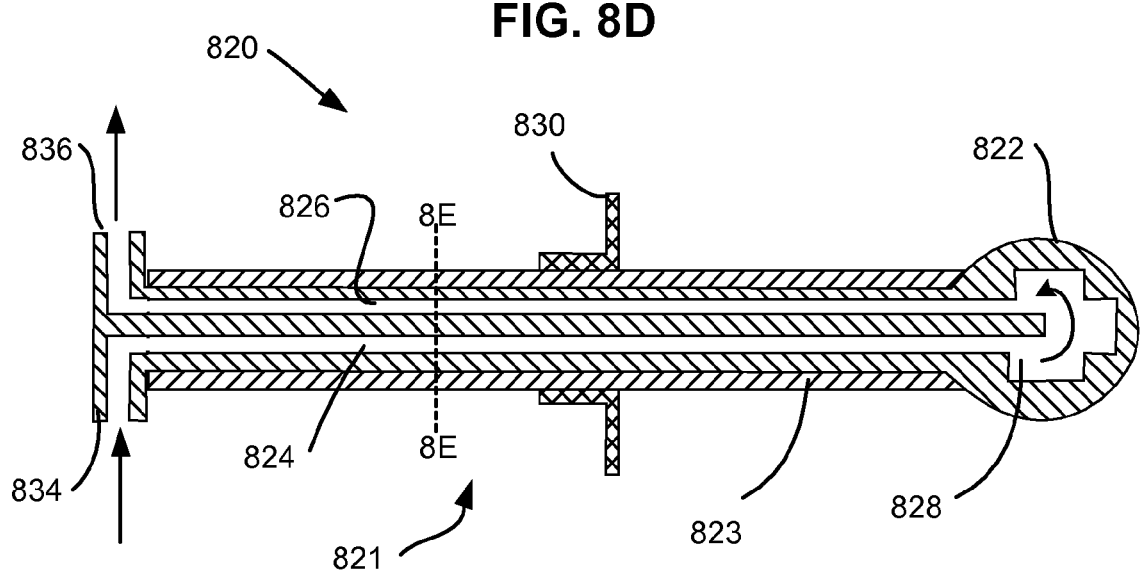
FIGS. 8D-8E show views of an alternate thermotherapy device for treating tissues of a pneumostoma according to an embodiment of the present invention.
Figure 8E:
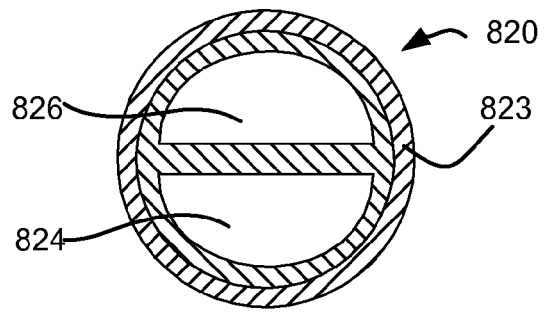

FIG. 8D shows an alternative cryotherapy probe 820. Cryotherapy probe 820 includes a shaft 821 and tip 822. Tip 822 is of fixed size and is preferably made of a heat conductive material. Tip 822 may be made in whole or in part of a biocompatible metal, for example surgical steel. Tip 822 may be made in one piece with shaft 821 or may be made separately and joined to shaft 821. As shown in FIG. 8E, shaft 821 (shown in FIG. 8D) includes two lumens 824, 826 for supplying coolant to tip 822 (in FIG. 8D). Tip 822 has a cavity 828 in which the coolant circulates. At the proximal end of cryotherapy probe 820 is an inlet 834 which communicates with lumen 824 and an outlet 836 which communicates with lumen 826. In some embodiments, shaft 820 may be coated with an insulating layer 823 so that treatment is limited to the region of the tip 822. Shaft 821 may be coated with an insulating material 823 in order that the cryotherapy treatment is localized to the region of tip 822. The tip 822 may then be moved to different locations in the pneumostoma to treat different areas.

The size of tip 822 may differ between different cryotherapy probes 820. A physician may have a range of cryotherapy probes available and choose the cryotherapy probe based upon the anatomy of the pneumostoma and the size and location of the tissues to be treated. Cryotherapy probe 820 may optionally be provided with a flange 830 positionable along shaft 821 in order to limit insertion of tip 822 into the pneumostoma and thereby control the location of tip 822 and the location of the cryotherapy treatment site.

In use, cryotherapy probe 820 is introduced into a pneumostoma to a position indicated by the markings on the exterior of the shaft 821 or position of the flange 830. Tip 822 is brought into thermal contact with the pneumostoma tissues to be treated. Cryotherapy probe 820 is connected to a cryotherapy coolant system 819. A coolant fluid is introduced through inlet 834 into lumen 824. The coolant passes through lumen 824 to the distal end of cryotherapy probe 820. The coolant passes through an aperture out of lumen 824 into the cavity 828. The coolant circulates around cavity 828 and cools the surface of tip 822 to the desired temperature. The coolant then returns through lumen 826 and exits the probe via the outlet 836. In some embodiments a temperature sensor may be included in the tip 822 of cryotherapy probe 820 in order to monitor the temperature of the tip. However, in other embodiments, temperature regulation is performed by regulating the temperature of the coolant supplied by the cryotherapy coolant system. For thermotherapy, a heated fluid may be circulated through the probe in place of the coolant.

Pneumostoma Treatment using Electromagnetic Radiation

The treatment modalities available for treating a pneumostoma include the application of energy in the form of electromagnetic radiation, for example, infrared, ultraviolet, visible light, RF, microwaves. Such energy treatment can be used to affect physical characteristics of tissues and cell proliferation and also to treat infection. For example, the tissues of the pneumostoma tend to encroach into the lumen of the pneumostoma and/or thicken the walls of the pneumostoma thereby impairing the function of the pneumostoma. One way to reduce tissue encroachment and/or thickness is through the application of energy to the tissues, either to kill the cells or to reduce their proliferation thereby maintaining or enhancing the patency of the pneumostoma. In some embodiments a pneumostoma treatment device may be used to direct energy to particular localized regions of the pneumostoma tissue, in other embodiments, the pneumostoma treatment device may apply energy equally in all directions. In other embodiments, the electromagnetic radiation may be selected to kill or damage bacteria to reduce infection while minimizing damage to the cells of the pneumostoma. Some frequencies of visible light, for example, have been shown to kill certain bacteria without causing significant damage to human cells.

Figure 9A:
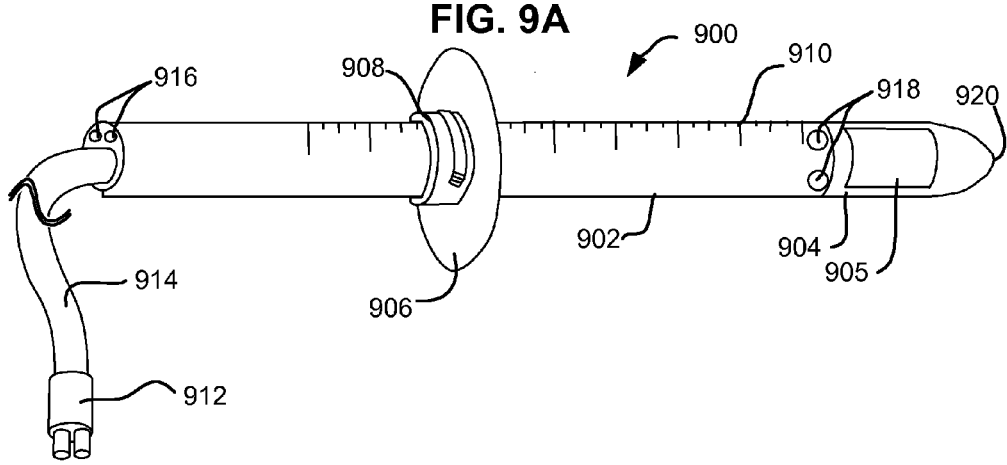
FIGS. 9A-9B show views of an electromagnetic treatment device for treating tissues of the pneumostoma according to an embodiment of the present invention.

FIG. 9A illustrates a pneumostoma treatment device 900 for treatment of pneumostoma tissues with electromagnetic radiation. The device includes a shaft 902 having at its distal end a treatment head 904. The treatment head has a tapered or rounded tip 920 to facilitate introduction into the pneumostoma. The treatment head 904 may generate electromagnetic radiation in situ, or the electromagnetic radiation may be transmitted from an external source to the treatment head 904. The treatment head may in some cases have a window 905 which is either open or covered with a material transparent to the electromagnetic radiation to be transmitted. In other cases the entire treatment head 904 may be enclosed in a material which is transparent to the delivered electromagnetic radiation.

At the proximal end the pneumostoma treatment device 900 has a coupling 912 for connecting the pneumostoma treatment device 900 to a power source which may provide the electromagnetic radiation directly or provide electrical power to create electromagnetic radiation in the treatment head 904. Coupling 912 may be connected to shaft 910 by a flexible cable 914. The proximal end of shaft 902 may also provide access to lumens 916 which communicate with apertures 918 adjacent treatment head 904. Lumens 916 and apertures 918 optionally provide suction, irrigation and/or cooling to the region adjacent treatment head 904 as necessary and/or desirable for a particular treatment modality.

The shaft 902 and treatment head 904 are of suitable diameter for insertion into a pneumostoma. Typically the shaft 902 and treatment head 904 will be less than approximately 10 mm in diameter. In some cases the shaft and treatment head may be approximately 5 mm in diameter. The shaft 902 is flexible enough to allow insertion of the treatment head 904 into a pneumostoma even when the pneumostoma is not entirely straight. The shaft 902 should however be stiff enough that it can provide adequate force to push the treatment head 904 to the correct location in the pneumostoma.

The pneumostoma treatment device carries a flange 906 which can slide on shaft 902. The flange 906 has a locking collar 908 to fix the flange 906 at an adjustable position along the shaft 902, other locking means may be used, for example, a suture, tape glue or mechanical lock. The physician will typically adjust the location of the flange 906 along the shaft 902 so that when the treatment head 904 and shaft 902 are inserted to the desired depth into a pneumostoma, the flange contacts the chest of the patient and prevent further insertion. Correct pre-positioning of the flange 906 on shaft 902 serves to guide treatment depth and protect against over insertion. The shaft 902 may also be provided with external markings 910 so that the physician may determine the correct location for flange 906 and the corresponding depth of treatment head 904.

Figure 9B:
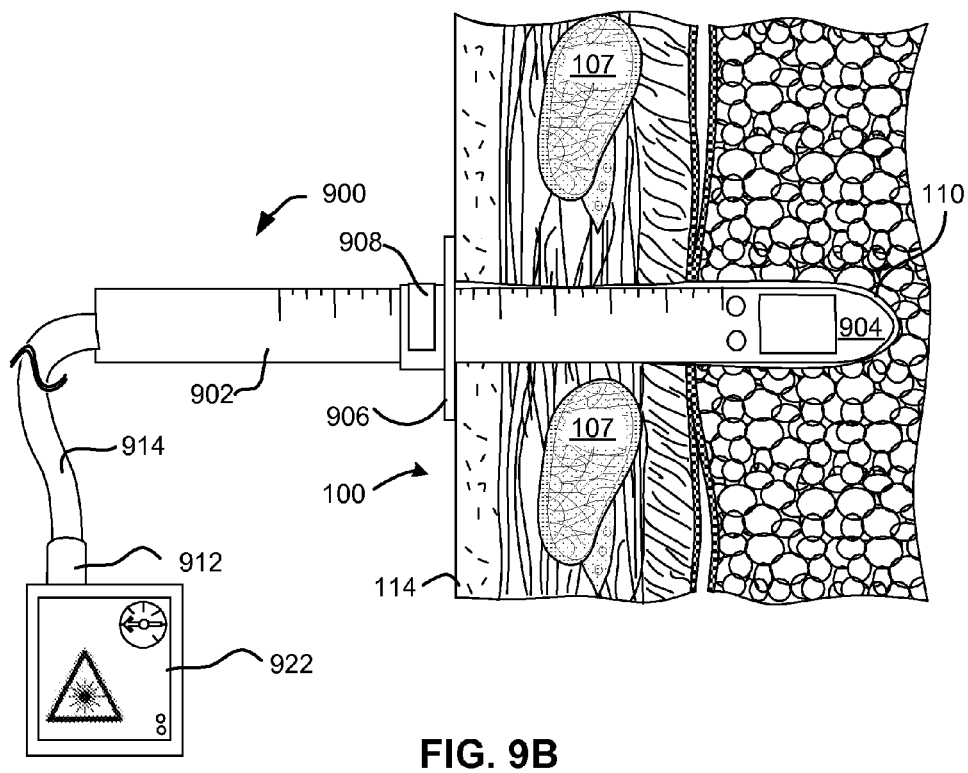

FIG. 9B shows a sectional view of pneumostoma treatment device 900 inserted into a pneumostoma 110. Note that flange 906 is in contact with the skin 114 of the chest 100 of the patient and thus acts as a mechanical stop to prevent further insertion. Flange 906 may additionally be provided with an adhesive (not shown) to temporarily secure the flange 906 to the skin 114 of the chest 100 of the patient thereby securing the treatment head 904 at the desired depth within the pneumostoma 110. Coupling 912 connects controller 922 via cable 914 to the proximal end of shaft 902 and via shaft 902 to treatment head 904. Controller 922 may be used to control the provision of electromagnetic radiation by treatment head 904. Controller may control one or more of: the location, intensity, wavelength and/or duration of the application of the electromagnetic radiation as directed by a physician.

The treatment head 904 may be designed so that it delivers electromagnetic radiation equally in all directions thereby treating uniformly all of the tissues adjacent the treatment head. In alternative embodiments treatment head 904 may be designed such that it applies the electromagnetic radiation in a directional manner—this adds additional complexity in that a mechanism needs to be provided for aligning the electromagnetic radiation with the target tissues. However, the directional solution allows for different tissues within the pneumostoma to be treated differently and also different regions to be treated differently from other regions. Directionality may be provided, for example, using scanning optics to aim a beam of electromagnetic radiation provided by controller 922 through a fiber optic cable.

FIG. 9C shows a sectional view of a pneumostoma treatment device 930 for treatment of pneumostoma tissues with electromagnetic radiation. The device includes a shaft 932 having at its distal end a treatment head 934. The shaft 932 carries a flange 936 which can slide on shaft 932. One or more lumens 946 passes along the length of shaft 932 to one or more aperture 948 adjacent treatment head 934. Lumens 946 and apertures 948 optionally provide suction, irrigation and/or cooling to the region adjacent treatment head 934 as necessary and/or desirable to enhance treatment or protect tissue during treatment. At the proximal end the pneumostoma treatment device 930 has a coupling 942 for connecting the pneumostoma treatment device 930 to a power source 940 which provides electrical power through cable 944 to create electromagnetic radiation in the treatment head 934.

In the embodiment shown in FIG. 9C, the treatment head 934 generates electromagnetic radiation in situ. The treatment head 934 is enclosed in a material which is transparent to the delivered electromagnetic radiation. As shown in FIG. 9C the treatment head 934 radiates electromagnetic radiation in all directions uniformly from source 935 located within head 934. Source 935, generates the desired electromagnetic radiation from electrical power provided by power source 940. The source may be for example, a source of IR, UV visible light, X-rays or other electromagnetic radiation with which it is desired to treat the tissue of the pneumostoma. Particular devices suitable for use as source 935 include for example incandescent light sources, LEDs, fluorescent lamps and miniature X-ray sources. The source may be provided with additional features to ensure uniformity of distribution of the selected electromagnetic radiation including, for example a collimator, diffuser, and or reflector.

FIG. 9D shows a sectional view of a pneumostoma treatment device 950 for treatment of pneumostoma tissues with electromagnetic radiation. The device includes a shaft 952 having at its distal end a treatment head 954. The shaft 952 carries a flange 956 which can slide on shaft 952. Flange 956 may be locked to shaft 952 and secured to the chest of the patient so that head 954 may be secured in a fixed relation to the pneumostoma during operation of pneumostoma treatment device 950. At the proximal end the pneumostoma treatment device 950 has a coupling 962 for connecting the pneumostoma treatment device 950 to a controller 960 which provides light and power through cable 964 to treatment head 954.

In the embodiment shown in FIG. 9D, the treatment head 954 does not generate electromagnetic radiation in situ. Instead, the electromagnetic radiation is generated by controller 960 and transmitted through an optical fiber 953 to treatment head 954. The treatment head 954 is enclosed in a material which is transparent to the delivered electromagnetic radiation. As shown in FIG. 9D, the treatment head 954 includes scanning optics 958 which direct the electromagnetic radiation in a particular direction under the control of controller 960. Controller 960 generates the desired electromagnetic radiation, transmits it to head 954 which directs it to a particular region of tissue of the pneumostoma. Controller 960 is connected to a computer system 964 which provides the physician with an interface 966 to operate controller 960 and control head 954 to treat selected target tissues within a pneumostoma.

Controller 960 may generate one or more selectable frequencies of electromagnetic radiation. Controller 960 may, for example include a tunable laser source cable of generating coherent light over a range of different frequencies. The light frequency and intensity may be selected based upon the effect desired. For example, in some case the light frequency and intensity may be selected to ablate certain target tissues in the pneumostoma. Tissue ablation may be used to generate pores in the wall of the pneumostoma to enhance patency of the pneumostoma and/or restore pathways for gas to exit the pneumostoma.

In some embodiments, the scanning optics may also receive light received back from the tissue, which light may pass back down the fiber optic to controller 960. The received light may be analyzed using tissue spectroscopy and/or tomography techniques to determine properties of the particular tissue from which the light is received. In such way the head 954 can be used to analyze the tissue of the pneumostoma in addition to, or instead of, treating the tissue. Tissue scanning may be used in order to select target tissues for e.g. ablation to enhance the selectivity of treatment and reduce damage to sensitive tissue. For example, tissue scanning may be used to ensure that tissue ablation avoids blood vessels in proximity to the pneumostoma when forming pores to restore or enhance the exit of gas through the pneumostoma.

Because of the proximity of blood vessels to the surface of the pneumostoma, the pneumostoma may also be used as a port for analysis of compounds in the bloodstream. For example analysis of blood gases, and/or glucose concentration. The analysis can be performed by scanning the thin tissues of the pneumostoma and analyzing the light received from the tissues. Information in the received light at different frequencies and in a number of modes (for example scattering, reflectance, absorption and fluorescence) may be used to derive detailed information regarding the tissues of the pneumostoma and blood in vessels immediately adjacent the pneumostoma.

Pneumostoma Management Device with Patency Sensor

Figure 10A:
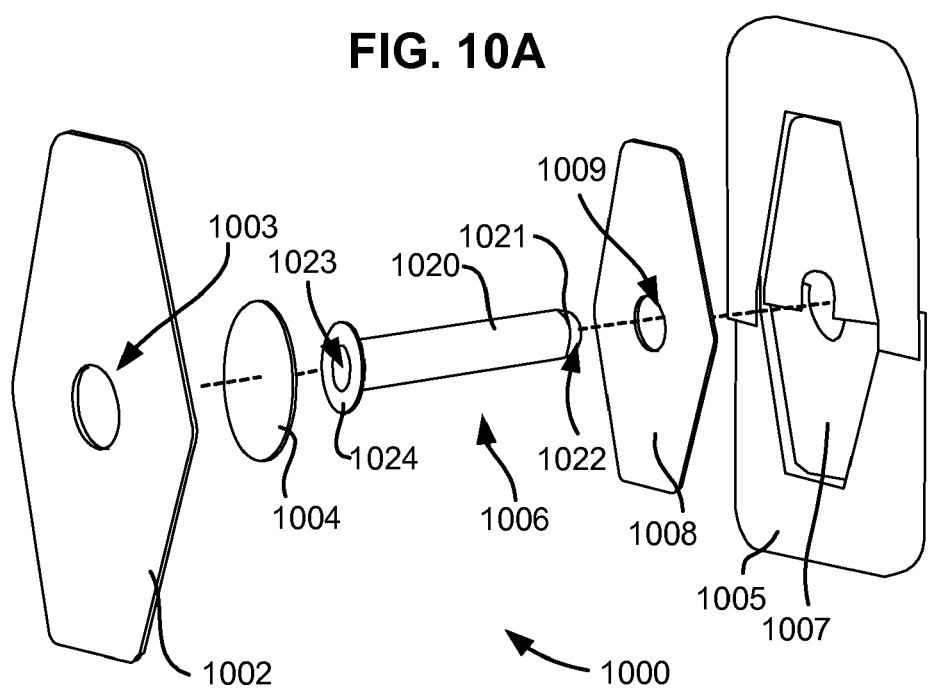
FIG. 10A shows an exploded view of a pneumostoma management device having a sensor for monitoring the patency of the pneumostoma.
Figure 10B:
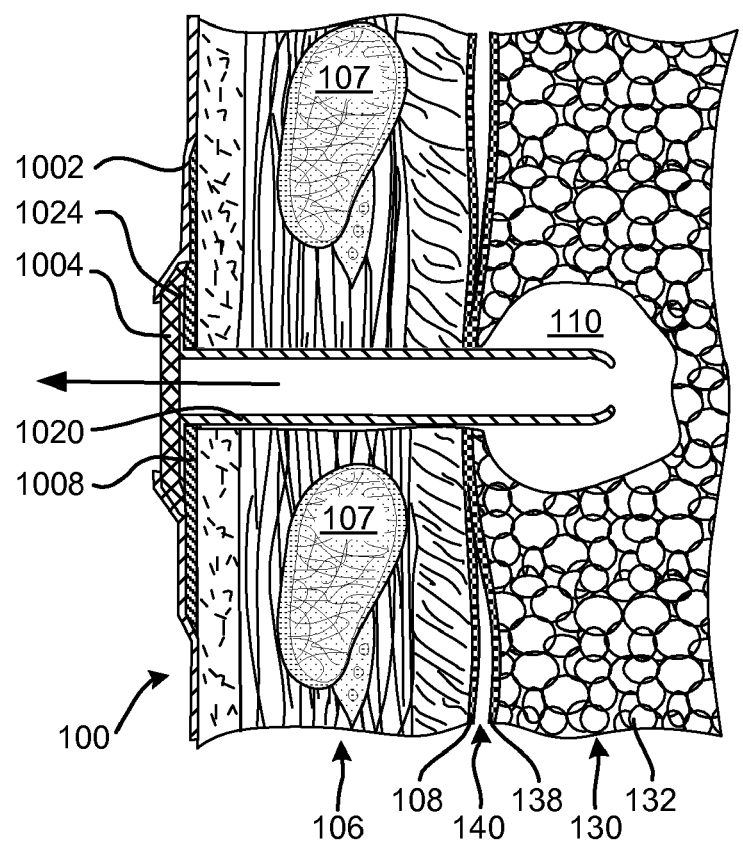
FIG. 10B shows a sectional view of the pneumostoma management device of FIG. 10A positioned in a pneumostoma.

FIGS. 10A-B show exploded and sectional views of a pneumostoma management device comprising pneumostoma vent system 1000. Pneumostoma vent system 1000 is designed to be secured directly to the chest of the patient. FIG. 10A shows an exploded view of the main components of pneumostoma vent system. From left to right these components are adhesive cover 1002, filter 1004, vent 1006, and adhesive patch 1008. A paper cover 1005 protects the adhesive cover and a paper cover 1007 protects the adhesive patch before use.

Adhesive cover 1002 is a thin porous biocompatible membrane which is adhesive on the surface facing the pneumostoma (the inner surface see 1026 in FIG. 6B) and non-adhesive on the outer surface 1020. A suitable material for adhesive cover 1002 is a thin polyurethane film bearing an acrylic adhesive—such materials are available from 3M of St. Paul, Minn. The film is biocompatible as well as thin, strong, and breathable. In a preferred embodiment the film is flesh colored. Adhesive cover 1002 has an aperture 1003 large enough to allow air to exit through filter 1004. Aperture 1003 is preferably slightly smaller than filter 1004 so that annular cover can be used to secure filter 1004 to vent 1006. Exposed adhesive portions of adhesive cover 1002 are provided with a paper cover 1005 to protect the adhesive prior to use. Paper cover 1005 is provided in two pieces to facilitate removal.

Adhesive patch 1008 is a preferably a hydrocolloid gel adhesive. In preferred embodiments, the proximal surface of the hydrocolloid gel is bonded with a flexible but inelastic polymer layer (e.g. a polyester film) to strengthen and maintain the dimensions of the adhesive patch 1008. A transition adhesive is in some embodiments provided between the proximal side of the adhesive patch and the adhesive cover to bond them together. Exposed adhesive portions of adhesive patch 1008 are provided with a paper cover 1007 to protect the adhesive prior to use. Paper cover 1007 is provided in two pieces to facilitate removal.

Filter 1004 is a circular disc of filter material. Filter 1004 is preferably a hydrophobic filter material. In a preferred embodiment, filter 1004 is a reticulated open cell polyurethane foam or an open cell polyurethane or polyester foam or melt blown polyethylene. Exemplary filter materials include Delpore® DP2001-10P, Delpore® DP2001-20P, and Delpore® DP2001-30P available from Delstar Technologies, Inc. (Middletown, Del.). Filter 1004 is larger than the proximal aperture 1023 in vent 1006 and is positioned over the proximal aperture 1023 to filter gases moving in and out of the vent 1006. Filter 1004 may be secured to vent 1006 by an adhesive, welding, or other bonding technology. In a preferred embodiment, filter 1004 is secured to vent 1004 with a ring of pressure sensitive adhesive. Filter 1004 is also secured to vent 1006 by adhesive cover 1002 instead of or in addition to other bonding techniques.

Vent 1006 comprises a tube 1020 for entering the pneumostoma. As previously discussed, tube 1020 has an atraumatic tip 1021 and one or more apertures 1022 in the distal end to allows gases and discharge to enter tube 1020 from a pneumostoma. Tube 1020 has a flange 1024 at the proximal end. Flange 1024 is formed in one piece with tube 1020. Filter 1004 is secured over proximal opening 1023 of vent 1006 as described in the previous paragraph. Vent 1006 may be made of a suitable plastic/thermoplastic polymer/thermoplastic elastomer. For example in one preferred embodiment vent 1006 is made of Pebax® a block copolymer with suitable mechanical and chemical properties available from Arkema (Colombes, France).

FIG. 10B shows a sectional view of the pneumostoma vent system 1000 in place in a pneumostoma 110. As shown in FIG. 10B, Flange 1024 and filter 1004 are both trapped between adhesive patch 1008 and adhesive cover 1002. Adhesive patch 1008 and adhesive cover 1002 also serve to secure pneumostoma vent system 1000 to the chest 100 of the patient and thereby secure tube 1020 within pneumostoma 110 such that gases can escape from the parenchymal tissue 132 of the lung 130 through the tube 1020, passing to ambient atmosphere through filter 1004.

The pneumostoma management device is, in some embodiments, provided with a patency indicator. The patency indicator is adapted to indicate whether the pneumostoma is still patent and/or efficacious. The pneumostoma is still patent when it the pneumostoma forms and open tube connecting the parenchymal tissue within the lung. The pneumostoma is efficacious when gases can escape from the parenchymal tissue of the lung through the pneumostoma. As previously stated, tissue overgrowth, will in some cases gradually reduce the patency and efficacy of the pneumostoma. A range of options is available to maintain the patency of the pneumostoma as discussed above. However, these interventions are most effective when carried out early. The patency indicator of the pneumostoma management device provides an early indication to the patient that the efficacy of the pneumostoma has been reduced thereby allowing the patient to consult a physician. The patency indicator aids the physician in making a determination whether to conduct further assessment and/or treatment of the pneumostoma (for example as discussed above)

In one embodiment of a patency indicator, filter 1004 comprises a colorimetric indicator responsive to gases exhaled through the pneumostoma. In order to provide a suitable indicator of patency, the colorimetric indicator is sensitive to a biomarker present in higher concentrations in exhaled gases than in the ambient atmosphere for example, carbon dioxide, carbon monoxide and/or nitric oxide. The colorimetric indicator is, in some embodiments, a colorant bond to the filter so that gases exiting the lung through the pneumostoma vent system 1000 pass through the filter. The colorimetric indicator is, in one embodiment, a pH sensitive colorant which changes color from a first color to a second color in the presence of a gas and changes back from the second color to the first color in the absence of the gas (reversible color change). The colorimetric indicator is, in another embodiment, a pH sensitive colorant which changes from a first color to a second color after exposure to a gas (irreversible color change).

Colorimetric indicators and filter materials incorporating colorimetric indicators are commercially available and are disclosed for example in: U.S. Pat. No. 5,005,572 entitled "$CO_2$ Indicator An The Use Thereof To Evaluate Placement Of Tracheal Tubes" to Raemer et al.; U.S. Pat. No. 5,834,626 entitled "Colorimetric Indicators For Breath, Air, Gas And Vapor Analyses And Method Of Manufacture" to De Castro et al.; U.S. Pat. No. 5,846,836 entitled "Reversible Detector For Gaseous Carbon Dioxide" to Mallow; and U.S. Pat. No. 6,502,573 entitled "Portable Single Patient Use Carbon Dioxide Detector" to Ratner. In one application such colorimetric indicators are used to evaluate the positioning of an endotracheal tube. During intubation the physician needs to know quickly whether the device has been places in the lung or the esophagus.

However, in the present application a much reduced rate of gas escape from the pneumostoma is expected, even when the pneumostoma is patent, than the rate of gas flow through the natural airways. Thus, the colorimetric sensor is sensitive to lower amounts of exhaled gas and responds over a significant period of time. In a preferred embodiment, for example, the colorimetric is responsive to a total volume of a biomarker passing through the filter rather than the instantaneous concentration of the biomarker. In a preferred embodiment, for example the colorimetric indicator changes irreversibly from a first color (e.g. white) to a second color (e.g. black) over a period of 12 to 24 hours in a pneumostoma. The time taken for the color change to occur provides an indication to the patient of the patency of the pneumostoma. The patient will change the pneumostoma management device daily. The patient can then observe the approximate time taken for the color change or absence of color change and provide that information to the physician.

Figure 10C:
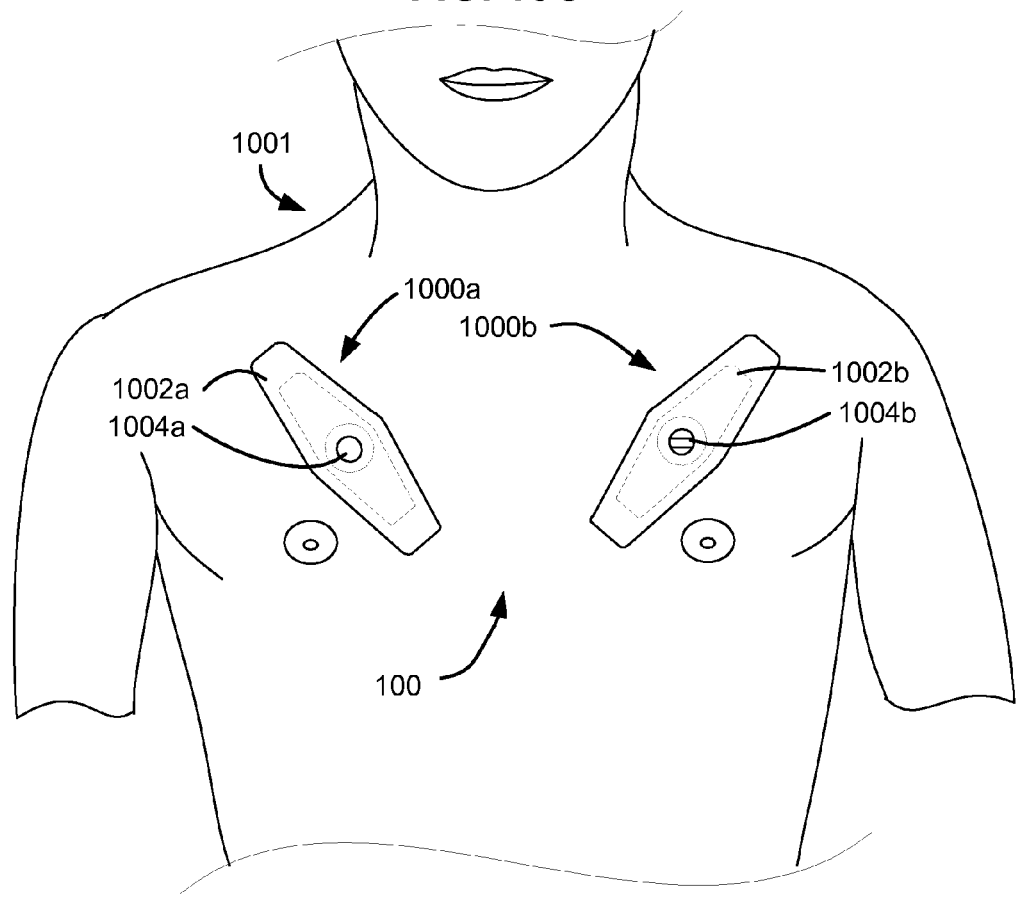
FIG. 10C shows a view of the pneumostoma management device of FIG. 10A on the chest of a patient.

FIG. 10C shows application of the pneumostoma vent system 1000a, 1000b to a patient. 1001. Patient 1001 has bilateral pneumostoma (not shown)—one pneumostoma for each lung. A pneumostoma vent system 1000a, 1000b has been inserted in each pneumostoma and secured to the chest 100 of patient 1001. As shown in FIG. 10C, the only visible portion of each pneumostoma vent system 1000a, 1000b is the proximal side if the adhesive patch 1002a, 1002b and filter 1004a, 1004b. Filter 1004b is a different color than filter 1004a as shown by shading. Thus, for example, if pneumostoma vent systems 1000a, 1000b were implanted in the pneumostoma at the same time and filter 1004a has remained the original color and filter 10004b has changed to a second color thus can be indicative of the absence of the biomarker (for example carbon dioxide) from filter 1004a. Thus, the patency indicator is clearly visible on the chest of the patient to the patient and/or care giver.

Figure 10D:
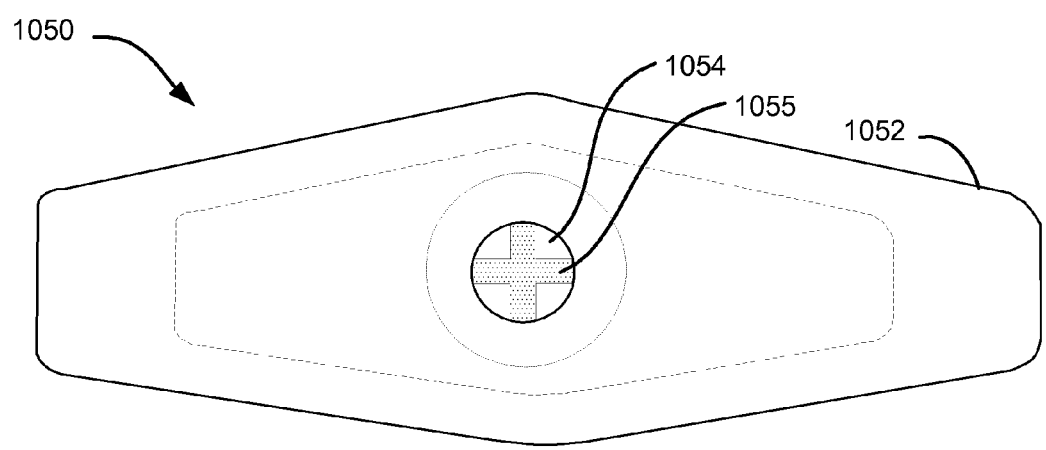
FIG. 10D shows an alternative pneumostoma management device.

FIG. 10D shows an alternative embodiment of a pneumostoma vent system 1050. Only adhesive cover 1052 and filter 1054 of pneumostoma vent system 1050 are shown in FIG. 10D as would be visible on the chest of a patient when implanted in a pneumostoma. Pneumostoma vent system is distinguished from pneumostoma vent system 1000 in that a colorimetric colorant has been bonded to the filter 1054 in a geometric pattern 1055 in this shape a cross or plus-sign. Thus, exposure of the colorimetric colorant to the biomarker only changes the color of the portion 1055 of filter 1054. The arrangement of the colorimetric colorant may, in some embodiments, allow the patient to better distinguish the indication of patency.

Figure 10E:
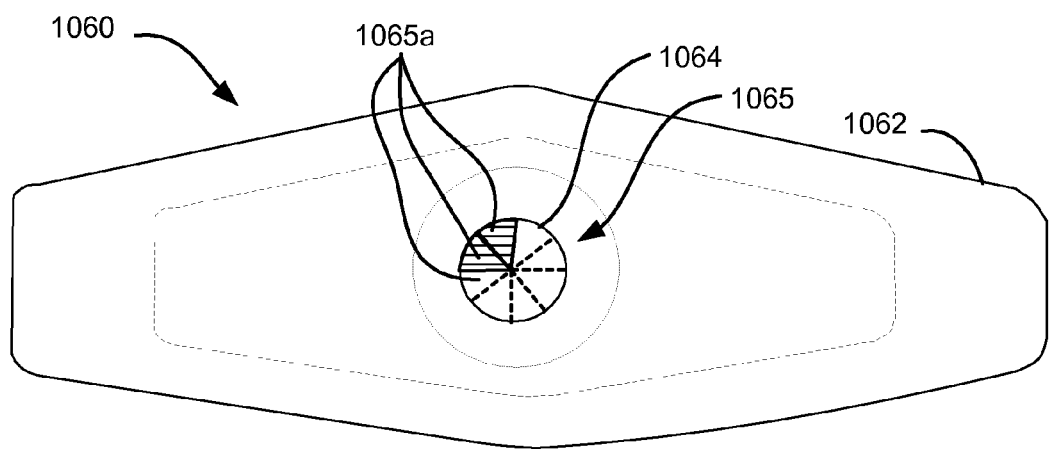
FIG. 10E shows an alternative pneumostoma management device.

FIG. 10E shows an alternative embodiment of a pneumostoma vent system 1060. Only adhesive cover 1062 and filter 1064 of pneumostoma vent system 1060 are shown in FIG. 10E as would be visible on the chest of a patient when implanted in a pneumostoma. Pneumostoma vent system is distinguished from pneumostoma vent system 1050 in that a colorimetric colorant has been bonded to the filter 1064 in a geometric pattern 1065 in a plurality of sectors 1065a. In each sector, a colorimetric colorant has been bonded that is sensitive to a different total amount of gas. Thus, for example a first sector can change color after a first total volume of gas, a second sector changes color after double the first amount of gas, the third sector after four times the amount of gas. Thus, the number of sectors of colorant that have changed color when the patient changes the pneumostoma management device provides an indication of the amount of the biomarker gas passing through the pneumostoma vent system 1060 and thus the patency of the pneumostoma.

Figure 10F:
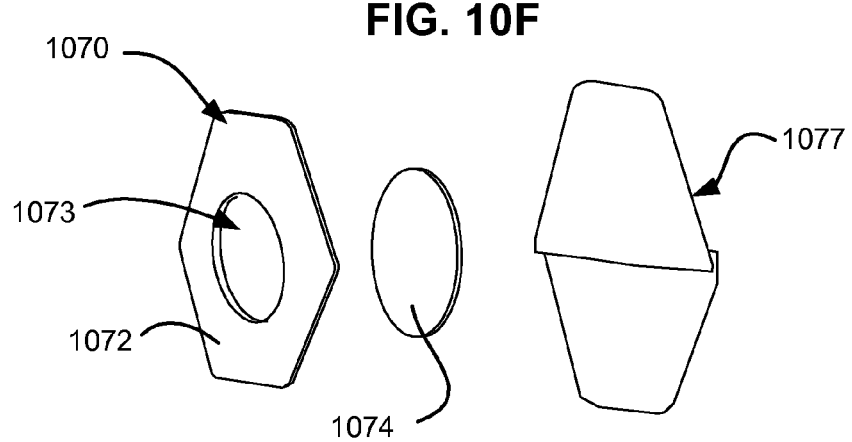
FIG. 10F shows a pneumostoma patency indicator according to an embodiment of the invention.

FIG. 10F shows an embodiment of a separate patency indicator 1070. Patency indicator 1070 includes an adhesive cover 1072 and a filter 1054, a biomarker-sensitive colorant being bound to the filter 1074. Adhesive cover 1072 is secured to filter 1074 with filter 1074 covering aperture 1073. A paper cover 1077 is provided to protect the distal (adhesive) surface of adhesive cover 1072 prior to use. Patency indicator 1070 is provided to a patient for use with a pneumostoma vent system 1000 not having a patency indictor. Periodically, or as directed by the physician, the patient secures separate patency indicator 1070 to the proximal surface of a pneumostoma vent system with the aperture 1073 and filter 1074 aligned with the aperture/filter of the pneumostoma vent system. Gases escaping through the pneumostoma vent system thus pass through both filters and the patency indicator 1070 can sample gases/biomarkers leaving the lung via the pneumostoma vent system. In some embodiments, a kit of biomarker sensors is provide to the patient having colorants sensitive to differing biomarkers and/or differing amounts of biomarkers. For example carbon dioxide might be utilized as a biomarker of patency and nitric oxide as a biomarker of inflammation.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. Embodiments of the present invention may use some or all of the features shown in the various disclosed embodiments where such features are not structurally or functionally incompatible. It is intended that the scope of the invention be defined by the claims and their equivalents.

What is claimed is:

1. A pneumostoma vent to allow gases to exit a lung through a pneumostoma in a chest of a patient, wherein the pneumostoma vent comprises;
   a tube adapted to be inserted into the chest through the pneumostoma,
   the tube having a lumen, a proximal end and a distal end
   the distal end of the tube having at least one opening adapted to admit gases from the lung;
   the proximal end of the tube having a feature projecting a sufficient distance from the tube to preclude passage of proximal end of the tube into the pneumostoma,
   an adhesive patch surrounding the tube; the adhesive patch having an aperture through which the tube passes, the aperture being too small to allow passage of the feature projecting from the tube;
   a hydrophobic filter disposed over the proximal end of the tube such that gases passing into and out of the lumen of the tube pass through the filter;
   an adhesive cover having an aperture smaller than the filter and positioned such that the adhesive cover contacts the perimeter of the filter, the feature projecting from the tube and at least a portion of the adhesive patch, such that the feature projecting from the tube is disposed between the adhesive patch and the adhesive cover, and the filter is disposed between the adhesive cover and the proximal end of the tube; and
   an indicator adapted to provide a visible indicia of patency of the pneumostoma.

2. The pneumostoma vent of claim 1, wherein the indicator is adapted to change color in response to a gas exiting the lung through the pneumostoma vent to provide a visible indicia of efficacy of the pneumostoma.

3. The pneumostoma vent of claim 1, wherein the indicator is a colorimetric reagent integrated with the filter.

4. The pneumostoma vent of claim 1, wherein:
   the indicator is a colorimetric reagent integrated with the filter; and
   wherein the colorimetric reagent is adapted to change color in response to a gas exiting the lung through the pneumostoma vent.

5. The pneumostoma vent of claim 1, wherein the indicator is integrated into the filter and the filter is adapted to change color in response to a gas exiting the lung through the pneumostoma vent.

6. The pneumostoma vent of claim 1, wherein the indicator is integrated into the filter and a geometrically-shaped portion of the filter is adapted to change color compared to other portions of the filter in response to gases exiting the lung through the pneumostoma.

7. The pneumostoma vent of claim 1, wherein the indicator is adapted to reversibly change color in response to gases exiting the lung through the pneumostoma.

8. The pneumostoma vent of claim 1, wherein the indicator is adapted to irreversibly change color in response to gases exiting the lung through the pneumostoma.

9. The pneumostoma vent of claim 1, wherein the feature, filter, adhesive coating and adhesive patch is less than 5 mm in thickness in combination.

10. A pneumostoma vent to allow gases to exit a lung through a pneumostoma in a chest of a patient, wherein the pneumostoma vent comprises;
   a tube adapted to be inserted into the chest through the pneumostoma,
   the tube having a lumen, a proximal end and a distal end
   the distal end of the tube having at least one opening adapted to admit gases from the lung;
   the proximal end of the tube having a feature prolectinq a sufficient distance from the tube to preclude passage of proximal end of the tube into the pneumostoma,
   an adhesive patch surrounding the tube; the adhesive patch having an aperture through which the tube passes, the aperture being too small to allow passage of the feature prolectinq from the tube;

a filter disposed over the proximal end of the tube such that gases passing into and out of the lumen of the tube pass through the filter;

an adhesive cover having an aperture smaller than the filter and positioned such that the adhesive cover contacts the perimeter of the filter, the feature projecting from the tube and at least a portion of the adhesive patch, such that the feature projecting from the tube is disposed between the adhesive patch and the adhesive cover, and the filter is disposed between the adhesive cover and the proximal end of the tube;

the filter is a hydrophobic filter adapted to allow gases to escape from the tube but retain liquids or solids; and the indicator is a colorant bound to the filter and adapted to change color in response to a gas exiting the lung through the pneumostoma vent.

11. A medical device adapted to allow gases to exit a lung through a pneumostoma in a chest of a patient, wherein the medical device comprises;

a tube adapted to be inserted into the chest through the pneumostoma,
the tube having a lumen, a proximal end and a distal end;
the distal end of the tube having at least one opening adapted to admit gases from the lung;
the proximal end of the tube having a flange projecting a sufficient distance from the tube to preclude passage of proximal end of the tube into the pneumostoma, a hydrocolloid patch surrounding the tube;

a hydrophobic filter disposed over the proximal end of the tube adapted to allow gases to escape the tube;

an adhesive cover having an aperture smaller than the filter; and an indicator adapted to provide a visible indicia of patency of the pneumostoma;

wherein the adhesive cover secures the filter over the proximal end of the tube, and the adhesive cover is secured to a portion of the hydrocolloid patch; with the flange positioned between the adhesive cover and the hydrocolloid patch.

12. The medical device of claim 11, wherein the indicator is a colorimetric indicator.

13. The medical device of claim 12, wherein the colorimetric indicator is adapted to change color in response to a gas exiting the lung through the pneumostoma.

14. The medical device of claim 13, wherein the colorimetric indicator is adapted to irreversibly change color in response to a gas exiting the lung through the pneumostoma.

15. The medical device of claim 14, wherein the colorimetric indicator is a colorant bound to the filter.

16. The medical device of claim 15, wherein the colorant is adapted to change color in response to carbon dioxide exiting the lung through the pneumostoma.

17. The medical device of claim 16, wherein the adhesive cover is a breathable polymer film having one adhesive surface adapted to be releasably secure the medical device to the chest of the patient.

18. A medical device adapted to allow gases to exit a lung through a pneumostoma in a chest of a patient, wherein the medical device comprises;

a tube adapted to be inserted into the chest through the pneumostoma,
the tube having a lumen, a proximal end and a distal end;
the distal end of the tube having at least one opening adapted to admit gases from the lung;
the proximal end of the tube having a flange projecting a sufficient distance from the tube to preclude passage of proximal end of the tube into the pneumostoma, a hydrocolloid patch surrounding the tube;

a hydrophobic filter disposed over the proximal end of the tube adapted to allow gases to escape the tube;

an adhesive cover having an aperture smaller than the filter and positioned such that the adhesive cover secures the filter over the proximal end of the tube, and the adhesive cover is secured at least a portion of the hydrocolloid patch; and a colorant bound to the filter and adapted to change color in response to a gas exiting the lung through the pneumostoma and thereby provide a visible indicia of patency of the pneumostoma.

19. The medical device of claim 18, wherein the colorant is adapted to undergo an irreversible color change in response to a gas dioxide exiting the lung through the pneumostoma.

20. The medical device of claim 18, wherein the colorant is adapted to undergo an irreversible color change in response to carbon dioxide exiting the lung through the pneumostoma.

* * * * *